(12) United States Patent
Park et al.

(10) Patent No.: US 7,932,213 B2
(45) Date of Patent: Apr. 26, 2011

(54) SMALL MOLECULE PRINTING

(75) Inventors: Seung Bum Park, Arlington, MA (US);
David Barnes-Seeman, Cambridge, MA (US); Angela N. Koehler, Cambridge, MA (US); Stuart L. Schreiber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1137 days.

(21) Appl. No.: 10/370,885

(22) Filed: Feb. 20, 2003

(65) Prior Publication Data

US 2003/0215876 A1    Nov. 20, 2003

Related U.S. Application Data

(63) Continuation-in-part of application No. 09/567,910, filed on May 10, 2000, now Pat. No. 6,824,987.

(60) Provisional application No. 60/133,595, filed on May 11, 1999.

(51) Int. Cl.
*C40B 40/04* (2006.01)
*C40B 30/04* (2006.01)
*C40B 50/08* (2006.01)
*C40B 60/04* (2006.01)
*G01N 33/566* (2006.01)
*G01N 33/543* (2006.01)
*G01N 33/53* (2006.01)

(52) U.S. Cl. .......... 506/15; 506/9; 506/27; 506/35; 436/287.1; 436/501; 436/518; 436/809

(58) Field of Classification Search .......... 435/4, 6, 435/7.1, 283.1, 287.1, 287.2, DIG. 29, DIG. 34, 435/DIG. 40, DIG. 42, DIG. 43, DIG. 44, 435/DIG. 46, DIG. 49; 436/518, 524, 528, 436/530, 287.1, 501, 809; 564/244, 247, 564/272; 506/9, 15, 27, 35

See application file for complete search history.

(56) References Cited

U.S. PATENT DOCUMENTS

| | | |
|---|---|---|
| 4,618,509 A | 10/1986 | Bulkowski |
| 4,670,224 A | 6/1987 | Stehning et al. |
| 4,698,009 A | 10/1987 | Marin et al. |
| 4,937,188 A | 6/1990 | Giese et al. ............ 435/41 |
| 4,964,972 A | 10/1990 | Sagiv et al. |
| 5,011,770 A | 4/1991 | Kung et al. ............ 435/6 |
| 5,228,804 A | 7/1993 | Balch |
| 5,395,783 A | 3/1995 | Baumann et al. |
| 5,412,087 A | 5/1995 | McGall et al. ............ 536/24.3 |
| 5,523,597 A | 6/1996 | Baumann et al. |
| 5,534,259 A | 7/1996 | Zalipsky et al. |
| 5,565,324 A | 10/1996 | Still et al. ............ 435/6 |
| 5,599,695 A | 2/1997 | Pease et al. ............ 435/91.1 |
| 5,620,850 A | 4/1997 | Bamdad et al. ............ 530/300 |
| 5,622,826 A | 4/1997 | Varma ............ 435/6 |
| 5,631,469 A | 5/1997 | Carrieri et al. |
| 5,639,603 A | 6/1997 | Dower et al. |
| 5,679,773 A | 10/1997 | Holmes |
| 5,681,484 A | 10/1997 | Zanzucchi et al. |
| 5,686,548 A | 11/1997 | Grainger et al. |
| 5,686,549 A | 11/1997 | Grainger et al. |
| 5,712,171 A | 1/1998 | Zambias et al. |
| 5,738,990 A | 4/1998 | Edwards et al. ............ 435/6 |
| 5,759,779 A | 6/1998 | Dehlinger |
| 5,763,263 A | 6/1998 | Dehlinger et al. ............ 435/287 |
| 5,770,455 A | 6/1998 | Cargill et al. ............ 436/518 |
| 5,773,308 A | 6/1998 | Conrad et al. |
| 5,807,522 A | 9/1998 | Brown et al. ............ 422/50 |
| 5,831,070 A | 11/1998 | Pease et al. ............ 536/25.3 |
| 5,832,411 A | 11/1998 | Schatzmann et al. |
| 5,846,722 A | 12/1998 | Kauvar et al. ............ 435/6 |
| 5,847,150 A | 12/1998 | Dorwald |
| 5,858,804 A | 1/1999 | Zanzucchi et al. ............ 436/536 |
| 5,876,946 A | 3/1999 | Burbaum et al. ............ 435/7.1 |
| 5,908,926 A | 6/1999 | Pirrung et al. |
| 5,912,342 A | 6/1999 | Heinonen et al. ............ 540/139 |
| 5,919,626 A | 7/1999 | Shi et al. ............ 435/6 |
| 5,958,430 A | 9/1999 | Campbell et al. ............ 424/400 |
| 5,959,297 A | 9/1999 | Weinberg et al. |
| 5,962,736 A | 10/1999 | Zambias et al. ............ 564/152 |
| 5,985,551 A | 11/1999 | Brennan ............ 435/6 |
| 6,020,047 A | 2/2000 | Everhart ............ 428/209 |
| 6,022,963 A | 2/2000 | McGall et al. |

(Continued)

FOREIGN PATENT DOCUMENTS

EP    0 967 217 A2    12/1999

(Continued)

OTHER PUBLICATIONS

MacBeath et al., 1999, Printing Small Molecules as Microarrays and Detecting Protien-Ligand Interactions en Masse, J. Am. Chem. Soc., 121: 7967-7968.*

Holmes, 1997, Model Studies for new o-Nitrobenzyl Photolabile Linkers: Substituent Effects on the Rates of Photochemical Cleavage, J. Org. Chem., 62: 2370-2380.*

Barnes-Seeman et al., 2003, Expanding the Functiona Group Compatibility of Small-Molecule Microarrays: Discovery of Novel Calmodulin Ligands, Angew. Chem. Int. Ed., 42: 2376-2379.*

Brown et al., 1995, A single-bead decode strategy using electrospray ionization mass spectrometry and a new photolabile linker: 3-Amino-3-(2-nitrophenyl)propionic acid, Molecular Diversity, 1: 4-12.*

(Continued)

*Primary Examiner* — Amber D. Steele
(74) *Attorney, Agent, or Firm* — Wolf, Greenfield & Sacks, P.C.; C. Hunter Baker

(57) ABSTRACT

The present invention provides compositions and methods to facilitate the identification of compounds that are capable of interacting with a biological macromolecule of interest. A composition is provided that comprises an array of chemical compounds attached to a solid support, wherein the density of the array of compounds is at least 1000 spots per cm$^2$. The inventive arrays are generated by: providing a solid support functionalized with a selected chemical moiety capable of interacting with a chemical compound to form an attachment and delivering compounds to the solid support having a density of at least 1000 spots per cm$^2$. The present invention also provides methods for utilizing these arrays to identify small molecule partners for biological macromolecules of interest.

17 Claims, 21 Drawing Sheets

U.S. PATENT DOCUMENTS

| | | | |
|---|---|---|---|
| 6,027,890 A | 2/2000 | Van Ness et al. ............... 435/6 |
| 6,034,775 A | 3/2000 | McFarland et al. |
| 6,037,186 A | 3/2000 | Stimpson |
| 6,048,623 A | 4/2000 | Everhart et al. ............... 428/464 |
| 6,083,763 A | 7/2000 | Balch |
| 6,168,914 B1 | 1/2001 | Campbell et al. |
| 6,251,689 B1* | 6/2001 | Laborde et al. ............... 436/518 |
| 6,329,209 B1* | 12/2001 | Wagner et al. ............... 436/518 |
| 6,331,441 B1 | 12/2001 | Balch et al. |
| 6,579,725 B1* | 6/2003 | Seeberger et al. ........... 436/518 |
| 6,818,394 B1 | 11/2004 | O'Donnell-Maloney et al. |
| 6,824,987 B1 | 11/2004 | Schreiber et al. |
| 6,951,682 B1 | 10/2005 | Zebala |
| 2001/0024833 A1* | 9/2001 | Laborde et al. ............... 436/518 |
| 2004/0248287 A1 | 12/2004 | Hu et al. |
| 2005/0095639 A1 | 5/2005 | Schreiber et al. |
| 2005/0255491 A1* | 11/2005 | Lee et al. ........................ 435/6 |
| 2009/0221433 A1 | 9/2009 | Barnes et al. |

FOREIGN PATENT DOCUMENTS

| | | | |
|---|---|---|---|
| JP | 57-98501 | * | 6/1982 |
| JP | 2001-178472 A | | 7/2001 |
| WO | WO-93/22680 A1 | | 11/1993 |
| WO | WO-94/17083 A1 | | 8/1994 |
| WO | WO-95/02566 A1 | | 1/1995 |
| WO | WO 95/35505 | | 12/1995 |
| WO | WO-96/28457 A1 | | 9/1996 |
| WO | WO-96/30393 A1 | | 10/1996 |
| WO | WO-96/30761 A1 | | 10/1996 |
| WO | WO-96/36627 A1 | | 11/1996 |
| WO | WO 97/19749 | | 6/1997 |
| WO | WO-97/40025 A1 | | 10/1997 |
| WO | WO-97/40030 A1 | | 10/1997 |
| WO | WO-97/40034 A1 | | 10/1997 |
| WO | WO-97/45730 A1 | | 12/1997 |
| WO | WO-98/04902 A1 | | 2/1998 |
| WO | WO-98/04908 A1 | | 2/1998 |
| WO | WO-98/12559 A1 | | 3/1998 |
| WO | WO-98/15805 A1 | | 4/1998 |
| WO | WO-98/15813 A1 | | 4/1998 |
| WO | WO-98/15969 A2 | | 4/1998 |
| WO | WO-98/33586 A1 | | 8/1998 |
| WO | WO-98/34913 A1 | | 8/1998 |
| WO | WO-98/37078 A1 | | 8/1998 |
| WO | WO 98/46551 | | 10/1998 |
| WO | WO-98/46559 A1 | | 10/1998 |
| WO | WO 98/55866 | | 12/1998 |
| WO | WO-99/03341 A1 | | 1/1999 |
| WO | WO-99/03832 A1 | | 1/1999 |
| WO | WO-99/09073 A1 | | 2/1999 |
| WO | WO-99/20395 A1 | | 4/1999 |
| WO | WO-99/22016 A1 | | 5/1999 |
| WO | WO-99/25470 A1 | | 5/1999 |
| WO | WO-99/31506 A1 | | 6/1999 |
| WO | WO-99/31507 A1 | | 6/1999 |
| WO | WO-99/34018 A1 | | 7/1999 |
| WO | WO-99/35289 A1 | | 7/1999 |
| WO | WO-99/42605 A1 | | 8/1999 |
| WO | WO-99/45149 A1 | | 9/1999 |
| WO | WO-99/46587 A1 | | 9/1999 |
| WO | WO-99/60170 A1 | | 11/1999 |
| WO | WO-99/61461 A1 | | 12/1999 |
| WO | WO-99/67019 A1 | | 12/1999 |
| WO | WO-00/21967 A1 | | 4/2000 |
| WO | WO 2004/050830 | * | 6/2004 |

OTHER PUBLICATIONS

Amara, et al., "A Versatible Synthetic Dimerizer for the Regulation of Protein-Protein Interactions", *Proc. Natl. Acad. Sci. USA*, 94(20):10618-10623, 1997.

Brown, http://cmgm.stanford.edu/pbrown/mguide/index.html.

Chaiet, et al., *Arch. Biochem. Biophys.* 106: 1-5, 1964.

Clive, et al., *Tetrahedron Lett.* 32(49):7159-7160, 1991.

Czarnik, "Encoding Methods for Combinatorial Chemistry", *Curr. Opin. Chem. Bio.* 1: 60-66, 1997.

Dobbs, et al., *Chem. Eng. News.* 68(17): 2, 1990.

Erickson, *Chem. Eng. News*, 68(33): 2, 1990.

Furka, et al., *Abstract 14$^{th}$ Int. Congr. Biochem.* Prague, Czechoslovakia, 5: 47, 1988.

Furka, et al., "General Method for Rapid Synthesis of Multicomponent Peptide Mixtures", *Int. J. Pept. Protein Res.* 37: 487-493, 1991.

Harding, et al., *Nature*, 341: 758-760, 1989.

Hergenrother, et al., "Small-Molecule Microarrays: Covalent Attachment and Screening of Alcohol-Containing Small Molecules on Glass Slides", *J. Am. Chem. Soc.* XX:XX-XX, submitted.

Holt, et al., *J. Am. Chem. Soc.* 115: 9925-9938, 1993.

Islam, et al., *J. Med. Chem.* 37: 293-304, 1994.

Janolino, et al., "Immobilization of Proteins on Thionyl Chloride-Activated Controlled-Pore Glass" *Methods in Biotechnology*, vol. 1: *Immobilization of Enzymes and Cells* (Bickerstaff, ed.), Humana Press Inc., Totowa, NJ, vol. 1, pp. 21-26.

Kapoor, et al., *J. Am. Chem. Soc.* 120: 23-29, 1998.

Keenan, et al., "Synthesis and Activity of Bivalent FKBP12 Ligands for the Regulated Dimerization of Proteins", *Bioorg. Med. Chem.* 6(8): 1309-1335, 1998.

Lam, et al., "A New Type of Synthetic Peptide Library for Identifying Ligand-Binding Activity", *Nature*, 354: 82-84, 1991.

U.S. Appl. No. 08/951,930, filed Oct. 15, 1997, Schreiber et al.

Lam, et al., "The One-Bead-One-Compound" Combinatorial Library Method, *Chem Rev.*, 97: 411-448, 1997.

Licitra, et al., *Proc. Natl. Acad. Sci. USA*, 93: 12817-12821, 1996.

MacBeath, et al., "Printing Small Molecules as Microarrays and Detecting Protein-Ligand Interactions en Masse", *J. Am. Chem. Soc.* 121(34): 7967-7968, 1999.

March, *Advanced Organic Chemistry* (4$^{th}$ Ed.), New York: John Wiley & Sons, 795-797, 1992.

Morken, et al., *J. Am. Chem. Soc.* 120: 30-36, 1998.

Nestler, et al., "A General Method for Molecular Tagging of Encoded Combinatorial Chemistry Libraries", *J. Org. Chem.* 59: 4723-4724, 1994.

Okamoto, et al., "Microarray Fabrication with Covalent Attachment of DNA Using Bubble Jet Technology", *Nature Biotechnology*, 18: 438-441, 2000.

Panghorn, et al., "Safe and Convenient Procedure for Solvent Purification" *Organometallics*, 15(5): 1518-1520, 1996.

Schena, et al., *Science*, 270: 467-470, 1995.

Sebestyen, et al., *Bioorg. Med. Chem. Lett*. 3: 413-418, 1993.

Shalon, et al., *Genome Research*, 6: 639-645, 1996.

Siekierka, et al., *Nature*, 341: 755-757, 1989.

Strother, et al., *J. Am. Chem. Soc.* 122: 1205-1209, 2000.

Tan, et al., "Stereoselective Synthesis of Over Two Million Compounds Having Structural Features Both Reminiscent of Natural Products and Compatible with Miniaturized Cell-Based Assays", *J. Am. Chem. Soc.* 120: 8565-8566, 1998.

Tan, et al., *J. Am. Chem. Soc.* 121: 9073-9087, 1999.

Woolard, et al., *J. Org. Chem.* 62: 6102-6103, 1997.

Wnuk, *Chem. Eng. News*, 68(26): 2, 1990.

International Search Report and Written Opinion for PCT/US2007/000003 mailed Feb. 28, 2008.

International Preliminary Report on Patentability for PCT/US2007/000003 mailed Jul. 17, 2008.

Office Communication mailed Jul. 2, 2003 for U.S. Appl. No. 09/567,910.

Office Communication mailed Mar. 25, 2004 for U.S. Appl. No. 09/567,910.

Notice of Allowance mailed Jul. 21, 2004 for U.S. Appl. No. 09/567,910.

Office Communication mailed Apr. 13, 2007 for U.S. Appl. No. 10/998,867.

Office Communication mailed Oct. 29, 2007 for U.S. Appl. No. 10/998,867.

Office Communication mailed Jul. 24, 2008 for U.S. Appl. No. 10/998,867.

Office Communication mailed Mar. 13, 2009 for U.S. Appl. No. 10/998,867.

Office Communication mailed Oct. 28, 2009 for U.S. Appl. No. 10/998,867.

"Oligomer." Merriam-Webster Online Dictionary. 2007.

"Peptide." Merriam-Webster Online Dictionary. 2007.

Ameringer et al., Ultrathin functional star PEG coatings for DNA microarrays. Biomacromolecules. Jul.-Aug. 2005;6(4):1819-23.

Barnes-Seeman et al., Expanding the functional group compatibility of small-molecule microarrays: discovery of novel calmodulin ligands. Angew Chem Int Ed Engl. May 30, 2003;42(21):2376-9.

Bradner et al., A robust small-molecule microarray platform for screening cell lysates. Chem Biol. May 2006;13(5):493-504.

Burke et al., A synthesis strategy yielding skeletally diverse small molecules combinatorially. J Am Chem Soc. Nov. 3, 2004;126(43):14095-104.

Burke et al., Generating diverse skeletons of small molecules combinatorially. Science. Oct. 24, 2003;302(5645):613-8.

Chen et al., Convergent diversity-oriented synthesis of small-molecule hybrids. Angew Chem Int Ed Engl. Apr. 8, 2005;44(15):2249-52.

Cheng et al., Studies on repository compound stability in DMSO under various conditions. J Biomol Screen. Jun. 2003;8(3):292-304.

Chun et al., Diisocyanates as novel molecular binders for monolayer assembly of zeolite crystals on glass. Chem Commun (Camb). Sep. 7, 2002;(17):1846-7.

Duffner et al., A pipeline for ligand discovery using small-molecule microarrays. Curr Opin Chem Biol. Feb. 2007;11(1):74-82. Epub Dec. 13, 2006.

Fazio et al., Synthesis of sugar arrays in microtiter plate. J Am Chem Soc. Dec. 4, 2002;124(48):14397-402.

Gaur et al., A spectrophotometric method for the estimation of amino groups on polymer supports. Anal Biochem. Aug. 1, 1989;180(2):253-8.

Guo et al., Direct fluorescence analysis of genetic polymorphisms by hybridization with oligonucleotide arrays on glass supports. Nucleic Acids Res. Dec. 11, 1994;22(24):5456-65.

Houseman et al., Carbohydrate arrays for the evaluation of protein binding and enzymatic modification. Chem Biol. Apr. 2002;9(4):443-54.

Kanoh et al., Immobilization of natural products on glass slides by using a photoaffinity reaction and the detection of protein-small-molecule interactions. Angew Chem Int Ed Engl. Nov. 24, 2003;42(45):5584-7.

Koehler et al., Discovery of an inhibitor of a transcription factor using small molecule microarrays and diversity-oriented synthesis. J Am Chem Soc. Jul. 16, 2003;125(28):8420-1.

Köhn et al., Staudinger ligation: a new immobilization strategy for the preparation of small-molecule arrays. Angew Chem Int Ed Engl. 2003;42(47):5830-4.

Kumar et al., Small-molecule diversity using a skeletal transformation strategy. Org Lett. Jun. 23, 2005;7(13):2535-8.

Kuruvilla et al., Dissecting glucose signalling with diversity-oriented synthesis and small-molecule microarrays. Nature. Apr. 11, 2002;416(6881):653-7.

Lee et al., Fabrication of chemical microarrays by efficient immobilization of hydrazide-linked substances on epoxide-coated glass surfaces. Angew Chem Int Ed Engl. May 6, 2005;44(19):2881-4.

Lee et al., Facile preparation of carbohydrate microarrays by site-specific, covalent immobilization of unmodified carbohydrates on hydrazide-coated glass slides. Org Lett. Sep. 15, 2005;7(19):4269-72.

Lo et al., A library of spirooxindoles based on a stereoselective three-component coupling reaction. J Am Chem Soc. Dec. 15, 2004;126(49):16077-86.

Martzen et al., A Biochemical Genomics Approach for Identifying Genes by the Activity of Their Products. Science. 1999;286:1153-55.

Pintochovski et al., Thermal Characteristics of the H2SO4-H2O2 Silicon Wafer Cleaning System. Electrochem Soc. 1979;126:1428-30.

Reddy et al., Protein "fingerprinting" in complex mixtures with peptoid microarrays. Proc Natl Acad Sci U S A. Sep. 6, 2005;102(36):12672-7. Epub Aug. 25, 2005.

Schreiber, Small molecules: the missing link in the central dogma. Nat Chem Biol. Jul. 2005;1(2):64-6.

Sompuram et al., A water-stable protected isocyanate glass array substrate. Anal Biochem. Mar. 1, 2004;326(1):55-68.

St. Hilare et al., Oligosaccharide Mimetics Obtained by Novel, Rapid Screening of Carboxylic Acid Encoded Glycopeptide Libraries. J Am Chem Soc. 1998;120:13312-20.

Stavenger et al., Asymmetric Catalysis in Diversity-Oriented Organic Synthesis: Enantioselective Synthesis of 4320 Encoded and Spatially Segregated Dihydropyrancarboxamides. Angew Chem Int Ed Engl. Sep. 17, 2001;40(18):3417-3421.

Sternson et al., An Acid- and Base-Stable o-Nitrobenzyl Photolabile Linker for Solid Phase Organic Synthesis. Tetrahedron Lett. 1998;39(41):7451-7454.

Tallarico et al., An alkylsilyl-tethered, high-capacity solid support amenable to diversity-oriented synthesis for one-bead, one-stock solution chemical genetics. J Comb Chem. May-Jun. 2001;3(3):312-8.

Uttamchandani et al., Microarrays of tagged combinatorial triazine libraries in the discovery of small-molecule ligands of human IgG. J Comb Chem. Nov.-Dec. 2004;6(6):862-8.

Vandenabeele-Trambouze et al., Reactivity of Organic Isocyanates with Nucleophilic Compounds: Amines, Alcohols, Thiols, Oximes, and Phenols in Dilute Organic Solutions. Adv Environ Res. 2001;6:45-55.

Wang et al., Carbohydrate microarrays for the recognition of cross-reactive molecular markers of microbes and host cells. Nat Biotechnol. Mar. 2002;20(3):275-81.

Winssinger et al, PNA-encoded protease substrate microarrays. Chem Biol. Oct. 11, 2004;10(10):1351-60.

Winssinger et al., Profiling protein function with small molecule microarrays. Proc Natl Acad Sci U S A. Aug. 20, 2002;99(17):11139-44. Epub Aug. 7, 2002.

Wong et al., Modular synthesis and preliminary biological evaluation of stereochemically diverse 1,3-dioxanes. Chem Biol. Sep. 2004;11(9):1279-91.

Hergenrother et al., Small-Molecule Microarrays: Covalent Attachment and Screening of Alcohol-Containing Small Molecules on Glass Slides. J Am Chem Soc. 2000;122:7849-50.

Janolino et al., Immobilization of Proteins on Thionyl Chloride-Activated Controlled-Pore Glass. In: Methods in Biotechnology, vol. 1: Immobilization of Enzymes and Cells. Bickerstaff, ed. Humana Press, Inc., Totowa, NJ. 1996:21-26.

MacBeath et al., Printing proteins as microarrays for high-throughput function determination. Science. Sep. 8, 2000;289(5485):1760-3.

Shalon et al., A DNA microarray system for analyzing complex DNA samples using two-color fluorescent probe hybridization. Genome Res. Jul. 1996;6(7):639-45.

* cited by examiner

R=

To use the vessels, slides were placed face-down as illustrated below and reagent was injected under the slides with a P1000 Pipetman.

Photocapture precursors

SMALL MOLECULE PRINTING

RELATED APPLICATIONS

The present application claims priority under 35 U.S.C. §120 and is a continuation-in-part of application U.S. Ser. No. 09/567,910, filed May 10, 2000, now U.S. Pat. No. 6,824,987 entitled "Small Molecule Printing", which claims priority to provisional application U.S. Ser. No. 60/133,595, filed May 11, 1999, entitled "Small Molecule Printing", the entire contents of each of which is incorporated herein by reference.

GOVERNMENT SUPPORT

The work described herein was supported, in part, by grants from the National Institute of General Medical Sciences, and the National Cancer Institute. The United States government may have certain rights, in the invention.

BACKGROUND OF THE INVENTION

The ability to identify small molecule ligands for any protein of interest has far-reaching implications, both for the elucidation of protein function and for the development of novel pharmaceuticals. With the introduction of split-pool strategies for synthesis (Furka et al., *Int. J. Pept. Protein Res.* 1991, 37, 487; Lam et al., *Nature* 1991, 354, 82; each of which is incorporated herein by reference) and the development of appropriate tagging technologies (Nestler et al., *J. Org. Chem.* 1994, 59, 4723; incorporated herein by reference), chemists are now able to prepare large collections of natural product-like compounds immobilized on polymeric synthesis beads (Tan et al., *J. Am. Chem. Soc.* 1998, 120, 8565; incorporated herein by reference). These libraries provide a rich source of molecules for the discovery of new protein ligands.

With such libraries in hand, the availability of efficient methods for screening these compounds becomes imperative. One method that has been used extensively is the on-bead binding assay (Lam et al., *Chem. Rev.* 1997, 97, 411; incorporated herein by reference). An appropriately tagged protein of interest is mixed with the library and beads displaying cognate ligands are subsequently identified by a chromagenic or fluorescence-linked assay (Kapoor et al., *J. Am. Chem. Soc.* 1998, 120, 23; Morken et al., *J. Am. Chem. Soc.* 1998, 120, 30; St. Hilare et al., *J. Am. Chem. Soc.* 1998, 120, 13312; each of which is incorporated herein by reference). Despite the proven utility of this approach, it is limited by the small number of proteins that can be screened efficiently. In principle, the beads can be stripped of one protein and reprobed with another; however, this serial process is slow and limited to only a few iterations. In order to identify a specific small molecule ligand for every protein in a cell, tissue, or organism, high-throughput assays that enable each compound to be screened against many different proteins in a parallel fashion are required. Although Brown et al. (U.S. Pat. No. 5,807,522; incorporated herein by reference) have developed an apparatus and a method for forming high density arrays of biological macromolecules for large scale hybridization assays in numerous genetic applications, including genetic and physical mapping of genomes, monitoring of gene expression, DNA sequencing, genetic diagnosis, genotyping of organisms, and distribution of DNA reagents to researchers, the development of a high density array of natural product-like compounds for high-throughput screening has not been achieved.

Clearly, it would be desirable to develop methods for generating high density arrays that would enable the screening of compounds present in increasingly complex natural product-like combinatorial libraries in a high-throughput fashion to identify small molecule partners for biological macromolecules of interest.

SUMMARY OF THE INVENTION

The present invention provides compositions and methods to facilitate the high-throughput screening of compounds for the identification of desirable properties or interactions. In a preferred embodiment, the present invention provides compositions and methods to facilitate the identification of compounds that are capable of interacting with a biological macromolecule of interest. In one aspect, a composition is provided that comprises an array of more than one type of chemical compounds attached to a solid support, wherein the density of the array of compounds comprises at least 500 spots per $cm^2$, at least 1000 spots per $cm^2$, more preferably at least 5000 spots per $cm^2$, and most preferably at least 10,000 spots per $cm^2$. In another aspect, a composition is provided that comprises a plurality of one or more types of non-oligomeric chemical compounds attached to a glass or polymer support, wherein the density of the array of compounds comprises at least 1000 spots per $cm^2$. In a particularly preferred embodiment, the chemical compounds are non-peptidic and non-oligomeric. In particularly preferred embodiments, these compounds are attached to the solid support through a covalent interaction. In another particularly preferred embodiment, small molecules are attached to the solid support through a covalent interaction. In a particularly preferred embodiment, the compounds are attached to the solid support using a Michael addition reaction. In another preferred embodiment, the compounds are attached to the solid support through a silyl linker resulting from a silylation reaction. In yet another preferred embodiment, the compounds are attached to the solid support through a diazobenzylidene moiety by initial proton transfer from a heteroatom of the compound that bears an acidic proton to the methine carbon of the diazobenzylidene followed by nucleophilic displacement of $N_2$ by the heteroatom. In another embodiment, the compounds are attached to the solid support using photocapture chemistry. In general, these inventive arrays are generated by: (1) providing a solid support, wherein said solid support is functionalized with a selected chemical moiety capable of interacting with a desired chemical compound to form an attachment; (2) providing one or more solutions of one or more types of compounds to be attached to the solid support; and (3) delivering said one or more types of compounds to the solid support, whereby an array of compounds is generated and the array comprises a density of at least 1000 spots per $cm^2$ (FIG. 1). In other embodiments, the array comprises a density of at least 5000 spots per $cm^2$, and more preferably at least 10,000 spots per $cm^2$.

In another aspect, the present invention provides methods for utilizing these arrays to identify small molecule partners for biological macromolecules (e.g., proteins, peptides, polynucleotides) of interest comprising: (1) providing an array of one or more types of compounds (e.g., more preferably, small molecules), wherein the array has a density comprising at least 1000 spots per $cm^2$; (2) contacting the array with one or more types of biological macromolecules of interest; and (3) determining the interaction of specific small molecule-biological macromolecule partners (FIG. 1). In particularly preferred embodiments, the biological macromolecules of interest comprise a collection of one or more recombinant proteins. In another preferred embodiment, the biological macromolecules of interest comprise a collection of macromolecules from a cell lysate. In another preferred embodiment, the biological macromolecules of interest comprise a polynucleotide.

Definitions

Unless indicated otherwise, the terms defined below have the following meanings:

"Antiligand": As used herein, the term "antiligand" refers to the opposite member of a ligand/anti-ligand binding pair. The anti-ligand may be, for example, a protein or other macromolecule receptor in an effector/receptor binding pair.

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Ligand": As used herein, the term "ligand" refers to one member of a ligand/anti-ligand binding pair, and is referred to herein also as "small molecule". The ligand or small molecule may be, for example, an effector molecule in an effector/receptor binding pair.

"Michael Addition": The term "Michael addition" refers to the reaction in which compounds containing electron-rich groups (e.g., groups containing sulfur, nitrogen, oxygen, or a carbanion) add, in the presence of base, to olefins of the from C=C—Z (including quinones), where Z is an electron-withdrawing group, such as aldehydes, ketones, esters, amides, nitrites, $NO_2$, SOR, $SO_2R$, etc.

"Microarray": As used herein, the term "microarray" is a regular array of regions, preferably spots of small molecule compounds, having a density of discrete regions of at least about $1000/cm^2$.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Peptide": According to the present invention, a "peptide" comprises a string of at least three amino acids linked together by peptide bonds. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polynucleotide" or "oligonucleotide": Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 1998, 120, 8565; incorporated herein by reference) and pending application number 08/951,930, "Synthesis of Combinatorial Libraries of Compounds Reminiscent of Natural Products", the entire contents of which are incorporated herein by reference. In certain other preferred embodiments, natural-product-like small molecules are utilized.

DESCRIPTION OF CERTAIN PREFERRED EMBODIMENTS

Figure 1:
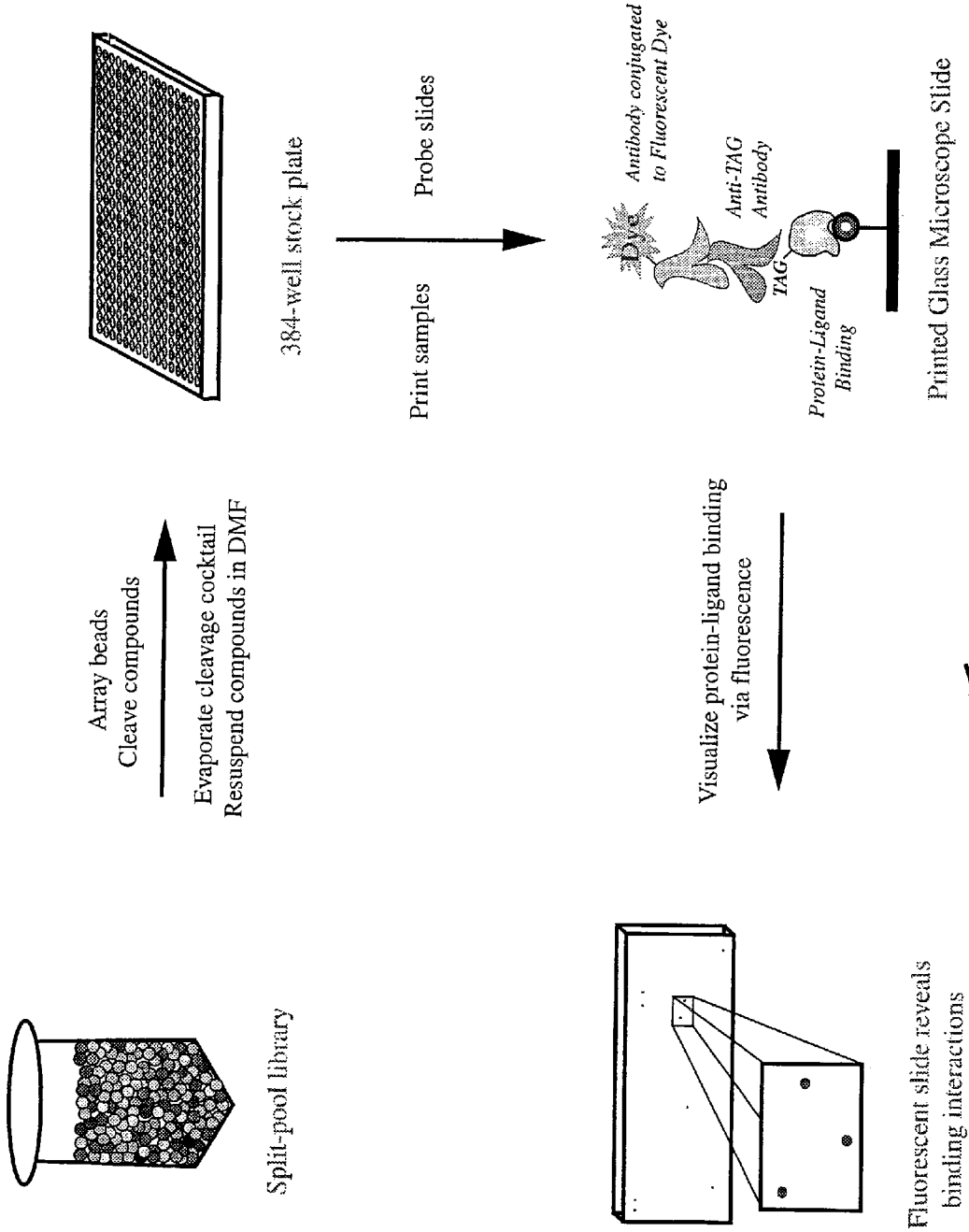
FIG. 1 depicts one preferred embodiment of the complete process of small printing and assaying for chemical compounds with desired properties. The process begins with the combinatorial library. The library is transferred to stock plates which are used to print the compounds onto glass slides. The slide is then used to assay for chemical compounds with the desired property.

As discussed above, the recent advances in the generation of complex chemical libraries of natural product-like compounds having as many as, or more than, one million members, has led to the subsequent need to facilitate the efficient screening of these compounds for biological activity. Towards this end, the present invention provides methods and compositions to enable the high-throughput screening of very large numbers of chemical compounds to identify those with desirable properties of interest. In preferred embodiments, methods and compositions are provided to enable the high-throughput screen of very large numbers of chemical compounds to identify those compounds capable of interacting with biological macromolecules.

In one aspect, the present invention provides compositions comprising arrays of chemical compounds, attached to a solid support having a density of at least 1000 spots per cm$^2$, and methods for generating these arrays. In particularly preferred embodiments, the present invention provides arrays of small molecules, more preferably natural product-like compounds, that are generated from split-and-pool synthesis techniques, parallel synthesis techniques, and traditional one-at-a time synthesis techniques. Additionally, existing collections of compounds may also be utilized in the present invention, to provide high density arrays that can be screened for desirable characteristics. In another aspect, the present invention provides methods for the identification of ligand (small molecule)-antiligand (biological macromolecule) binding pairs using the chemical compound arrays. It is particularly preferred that the antiligands comprise recombinant protein, and it is more particularly preferred that a library of recombinant proteins is utilized in the detection method. In another preferred embodiment, the antiligands comprise macromolecules from cell lysates.

Small Molecule Printing

As discussed above, in one aspect, the present invention provides methods, referred to herein as "small molecule printing", for the generation of high density arrays and the resulting compositions. According to the method of the present invention, a collection of chemical compounds, or one type of compound, can be "printed" onto a support to generate extremely high density arrays. In general, this method comprises (1) providing a solid support, wherein the solid support is functionalized with a selected chemical moiety capable of interacting with a desired chemical compound or collection of chemical compounds, to form an attachment(s); (2) providing one or more solutions of the same or different chemical compounds to be attached to the solid support; and (3) delivering the one or more solutions of the same or different chemical compounds to the solid support, whereby an array of compounds is generated and the array has a density of at least 1000 spots per cm$^2$.

As one of ordinary skill in the art will realize, although any desired chemical compound capable of forming an attachment with the solid support may be utilized, it is particularly preferred that natural product-like compounds, preferably small molecules, particularly those generated from split-andpool library or parallel syntheses are utilized. Examples of libraries of natural product-like compounds that can be utilized in the present invention include, but are not limited to shikimic acid-based libraries, as described in Tan et al. ("Stereoselective Synthesis of over Two Million Compounds Having Structural Features Both Reminiscent of Natural Products and Compatible with Miniaturized Cell-Based Assays", *J. Am. Chem. Soc.*, 1998, 120, 8565) and incorporated herein by reference. As will be appreciated by one of ordinary skill in the art, the use of split-and-pool libraries enables the more efficient generation and screening of compounds. However, small molecules synthesized by parallel synthesis methods and by traditional methods (one-at-a-time synthesis and modifications of these structures) can also be utilized in the compositions and methods of the present invention, as can naturally occurring compounds, or other collections of compounds, preferably non-oligomeric compounds, that are capable of attaching to a solid support without further synthetic modification.

As will be realized by one of ordinary skill in the art, in split-and-pool techniques (see, for example, Furka et al., *Abstr.* 14*th Int. Congr. Biochem.*, Prague, Czechoslovakia, 1988, 5, 47; Furka et al., *Int. J. Pept. Protein Res.* 1991, 37, 487; Sebestyen et al., *Bioorg. Med. Chem. Lett.* 1993, 3, 413; each of which is incorporated herein by reference), a mixture of related compounds can be made in the same reaction vessel, thus substantially reducing the number of containers required for the synthesis of very large libraries, such as those containing as many as or more than one million library members. As an example, a solid support bound scaffold can be divided into n vessels, where n represents the number of species of reagent A to be reacted with the support bound scaffold. After reaction, the contents from n vessels are combined and then split into m vessels, where m represents the number of species of reagent B to be reacted with the support bound scaffold. This procedure is repeated until the desired number of reagents are reacted with the scaffold structures to yield a desired library of compounds.

As mentioned above, the use of parallel synthesis methods are also applicable. Parallel synthesis techniques traditionally involve the separate assembly of products in their own reaction vessels. For example, a microtiter plate containing n rows and m columns of tiny wells which are capable of holding a small volume of solvent in which the reaction can occur, can be utilized. Thus, n variants of reactant type A can be reacted with m variants of reactant type B to obtain a library of n×m compounds.

Subsequently, once the desired compounds have been provided using an appropriate method, solutions of the desired compounds are prepared. In a preferred embodiment, compounds are synthesized on a solid support and the resulting synthesis beads are subsequently distributed into polypropylene microtiter plates at a density of one bead per well. In but one example, as discussed below in the Examples, the attached compounds are then released from their beads and dissolved in a small volume of suitable solvent. Due to the minute quantities of compound present on each bead, extreme miniaturization of the subsequent assay is required. Thus, in a particularly preferred embodiment, a high-precision transcription array robot (Schena et al., *Science* 1995, 270, 467; Shalon et al., *Genome Research* 1996, 6, 639; each of which is incorporated herein by reference) can be used to pick up a small volume of dissolved compound from each well and repetitively deliver approximately 1 nL of solution to defined locations on a series of chemically-derivatized glass microscope slides. These chemically-derivatized glass microscope slides are preferably prepared using custom slide-sized reaction vessels that enable the uniform application of solution to one face of the slide as shown and discussed in the Examples. This results in the formation of microscopic spots of compounds on the slides and in preferred embodiments these spots are 200-250 μm in diameter. It will be appreciated by one of ordinary skill in the art, however, that the current invention is not limited to the delivery of 1 nL volumes of solution and that alternative means of delivery can be used that are capable of delivering picoliter or smaller volumes. Hence, in addition to a high precision transcription array robot, other means for delivering the compounds can be used, including, but not limited to, ink jet printers, piezoelectric printers, and small volume pipetting robots.

As discussed, each compound contains a common functional group that mediates attachment to a support surface. It is preferred that the attachment formed is robust and therefore the formation of covalent attachments are particularly preferred. A variety of chemical linkages can be employed to generate the high density arrays of chemical compounds. In addition to the robustness of the linkage, other considerations include the solid support to be utilized and the specific class of compounds to be attached to the support. Particularly preferred supports include, but are not limited to glass slides, polymer supports or other solid-material supports, and flexible membrane supports.

Figure 2:
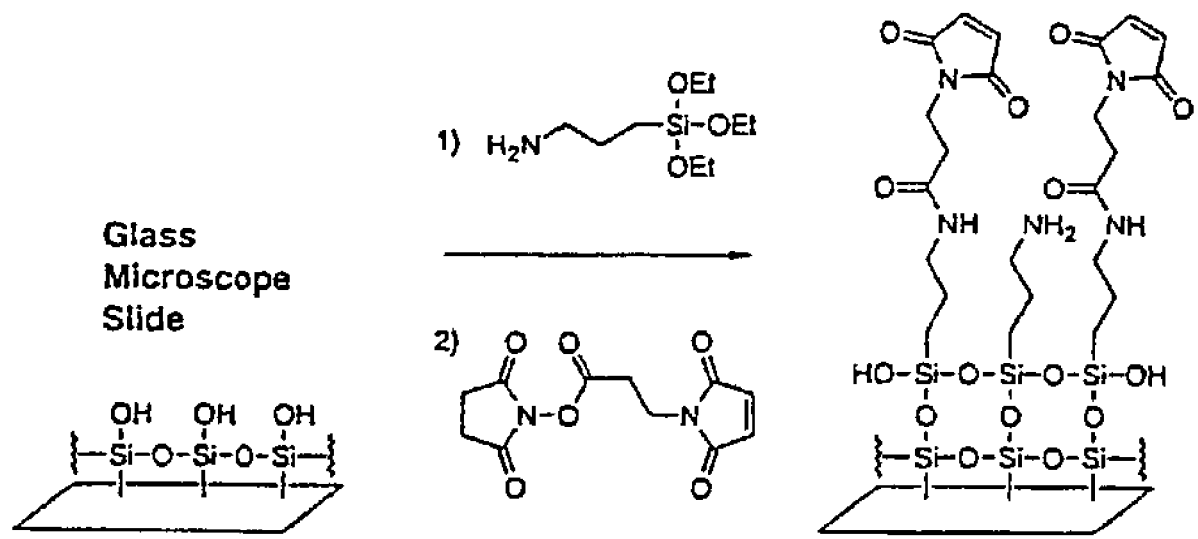
FIG. 2 depicts the preparation of maleimide-derivatized glass slides.

In but one example, and as discussed in Example 1, a Michael addition (March, *Advanced Organic Chemistry* (4th ed.), New York: John Wiley & Sons, 1992, 795-797; incorporated herein by reference) can be employed to attach compounds to glass slides. In one embodiment, as shown in FIG. 2, plain glass slides are derivatized to give surfaces that are densely functionalized with maleimide groups. Compounds containing thiol groups can then be provided. These thiol-containing compounds readily attach to the surface upon printing via the expected thioether linkage. As one of ordinary skill in the art will realize, other nucleophilic S—, N—, and O— containing compounds can be generated to facilitate attachment of the chemical compound to the solid support via Michael addition, as described above. Other electrophilic Michael acceptors can also be utilized; however, maleimides and vinyl sulfones are particularly preferred because the hydrophilicity of these groups is believed to play a role in the observed lack of nonspecific protein binding to the slide surface in aqueous buffer.

In another example, and as discussed in Example 2, a silylation reaction can be employed to attach compounds to a glass slide. Plain glass slides are derivatized to yield surfaces that are densely functionalized with silyl halides. Compounds containing hydroxyl groups can then be provided and contacted with the functionalized glass surface. The hydroxyl containing compounds readily attach to the surface through the silicon-oxygen bond formed by nucleophilic substitution on the silyl halide. In a preferred embodiment, the silyl halide is silyl chloride, bromide, or iodide. In other preferred embodiments, leaving groups on the silicon such as mesylate and tosylate are used rather than halides. Preferably, the hydroxyl groups of the compounds to be attached are unhindered (e.g., primary alcohols).

Figure 3:
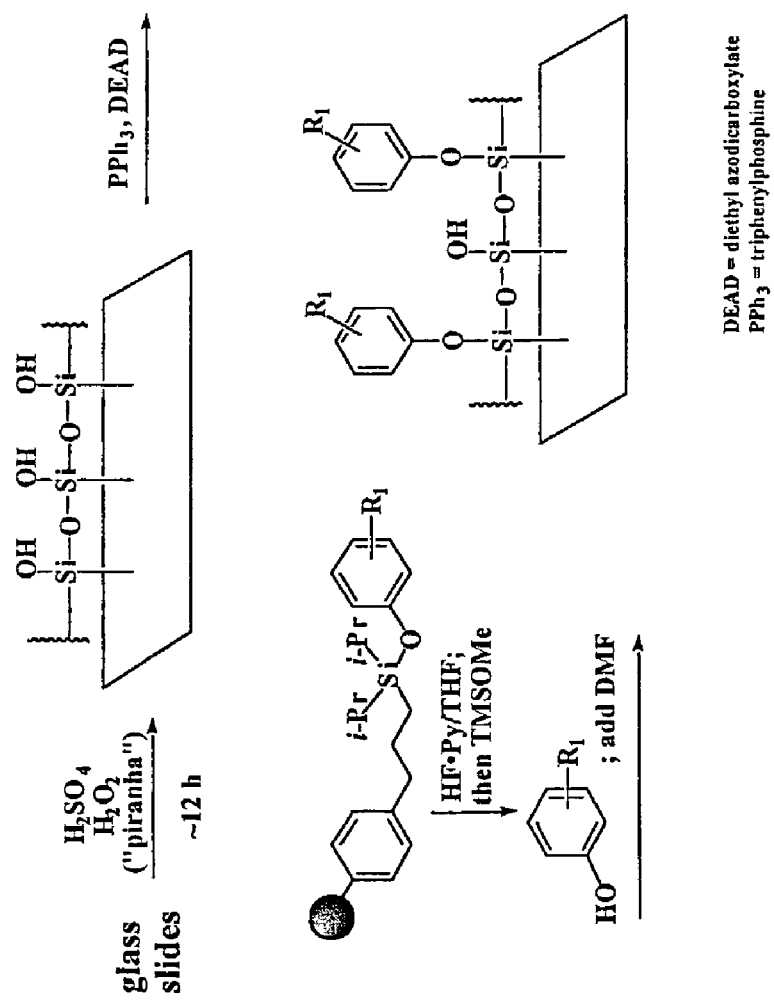
FIG. 3 shows the attachment of phenolic hydroxyl groups using a Mitsunobu activation of the glass surface.
Figure 4:
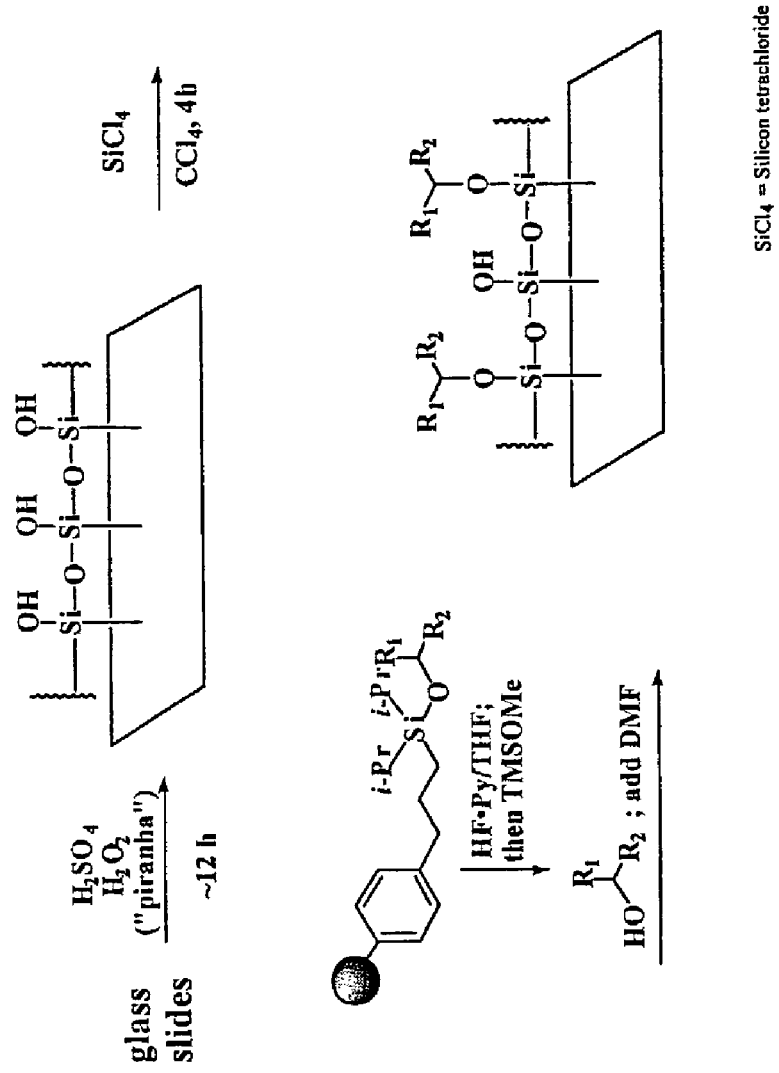
FIG. 4 shows the attachment of compounds having a secondary alcohol to a silicon tetrachloride-activated glass surface.

In another preferred embodiment, compounds with phenolic hydroxyl groups are attached to a glass surface using Mitsunobu activation of the surface as shown in FIG. 3 (Derrick et al., *Tetrahedron Lett.* 1991, 32, 7159; incorporated herein by reference). In yet another preferred embodiment, compounds with secondary alcohols are attached a glass surface activated with silicon tetrachloride (FIG. 4).

Figure 19:
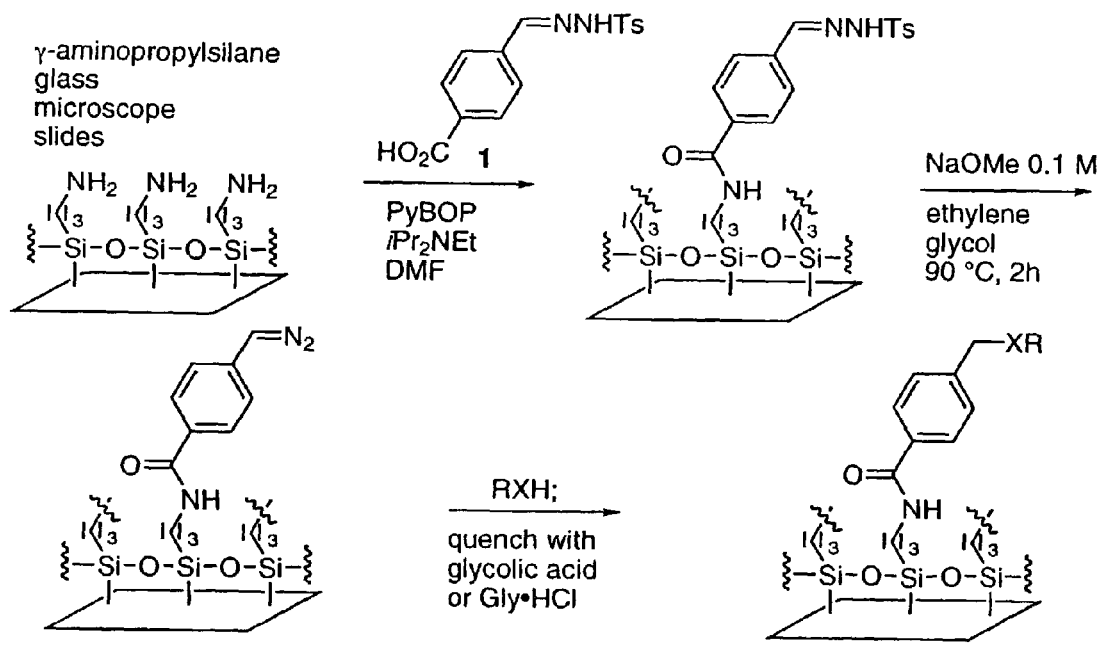
FIG. 19 shows the preparation of diazobenzylidene-derivatized glass slides and covalent attachment of functional groups that bear an acidic proton.

In yet another embodiment, compounds with functional groups that bear an acidic proton (e.g., thiols, phenols, carboxylic acids, sulfonamides, etc.) are attached to a surface using a diazobenzylidene-activated surface as shown in FIG. 19. Diazobenzylidene is known to react selectively with heteroatoms that bear an acidic proton. Covalent attachment is facilitated by an initial proton transfer from the heteroatom of the compound of interest to the methine carbon of the diazobenzylidene moiety. The proton transfer is followed by nucleophilic displacement of $N_2$ by the heteroatom. To give but one example of a method of preparing a surface such as a glass slide derivatized with a diazobenxylidene moiety, the toluenesulfonylhydrazone derived from 4-carboxybenzaldehyde is coupled to aminopropylsilane slides as shown in FIG. 19. Base-induced elimination yields the activated diazobenzylidene-derived surface. The benzylidene-derivatized surfaces are particularly useful in attaching compound with phenolic functional groups such as those that may be found in a combinatorial library. Other compounds that bear functional groups with a proton having a pKa <11 (pKa in DMSO <19) are also readily attached to these diazobenzylidene-activated surfaces. Compounds bearing a functional group with a proton having a pKa <16 (pKa in DMSO <28) may also be attached to these slides. One of the advantages of the diazobenzylidene-activated slides is that they don't react with water; therefore, the first spotted sample is almost identical to the last spotted sample. In addition, these slides have a longer shelf-life.

Figure 5:
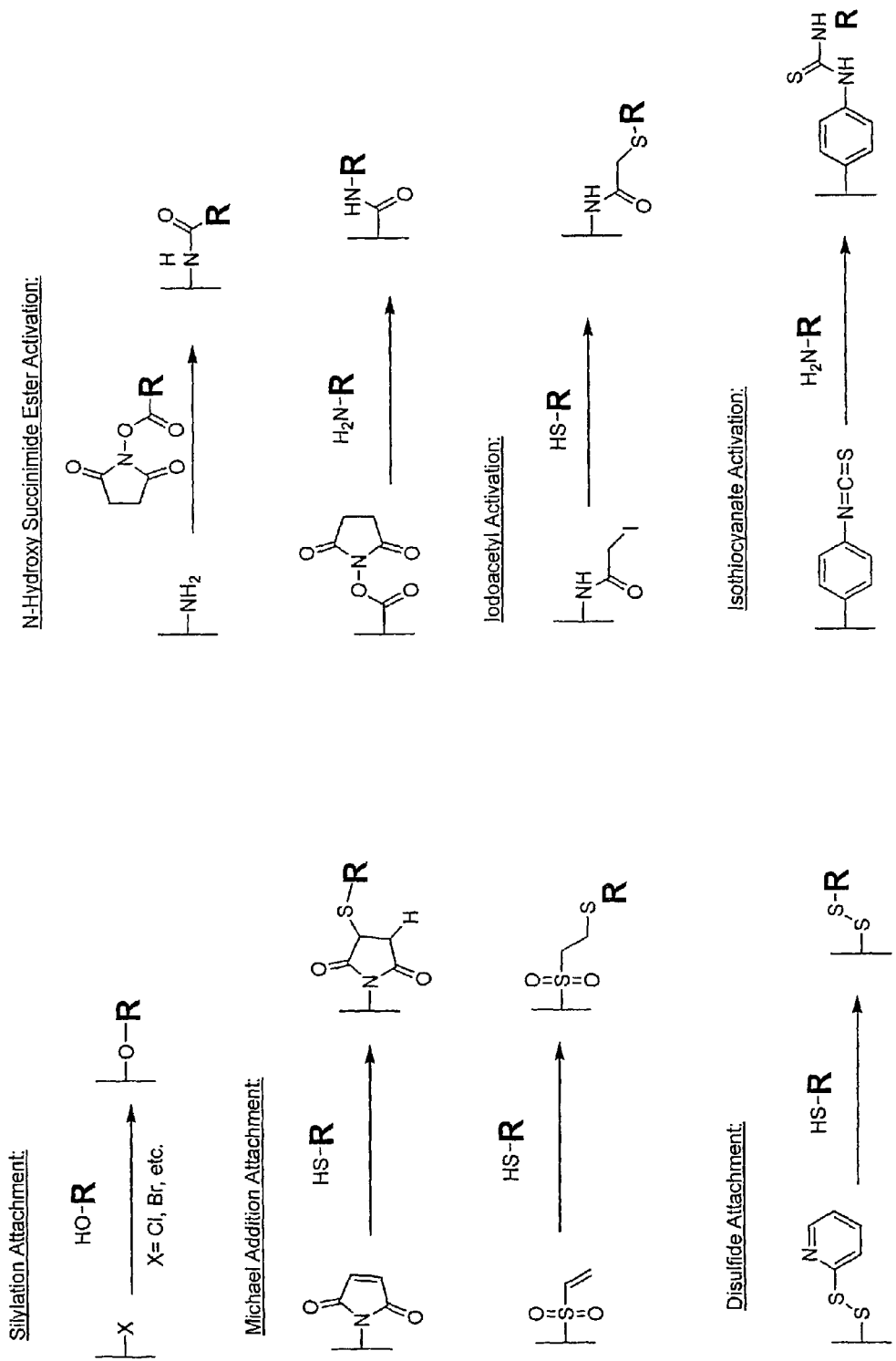
FIG. 5 shows other attachment chemistries which may be used in small molecule printing.

Other linkages (FIG. 5) that can be employed in the preparation of the inventive arrays include, but are not limited to disulfide bonds, amide bonds, ester bonds, ether bonds, hydrazone linkages, carbon-carbon bonds, metal ion complexes, and noncovalent linkages mediated by, for example, hydrophobic interactions or hydrogen bonding. In certain preferred embodiments, coupling of acids and amines, coupling of aldehydes and hydrazide, coupling of trichlorocyanuric acid and amines, addition of amines to quinones, attachment of thiols to mercury, addition of sulfhydryls, amines, and hydroxyls to open bis-epoxides, photoreactions of azido compounds to give insertions via a nitrene intermediate, or coupling of diols to boronate is used in the preparation of the inventive arrays. It will be appreciated by one of skill in this art that the specific linkages to be utilized should be selected to be (1) robust enough so that the small molecules are not inadvertently cleaved during subsequent assaying steps, and (2) inert so that the functionalities employed do not interfere with the subsequent assaying steps.

Figure 23:
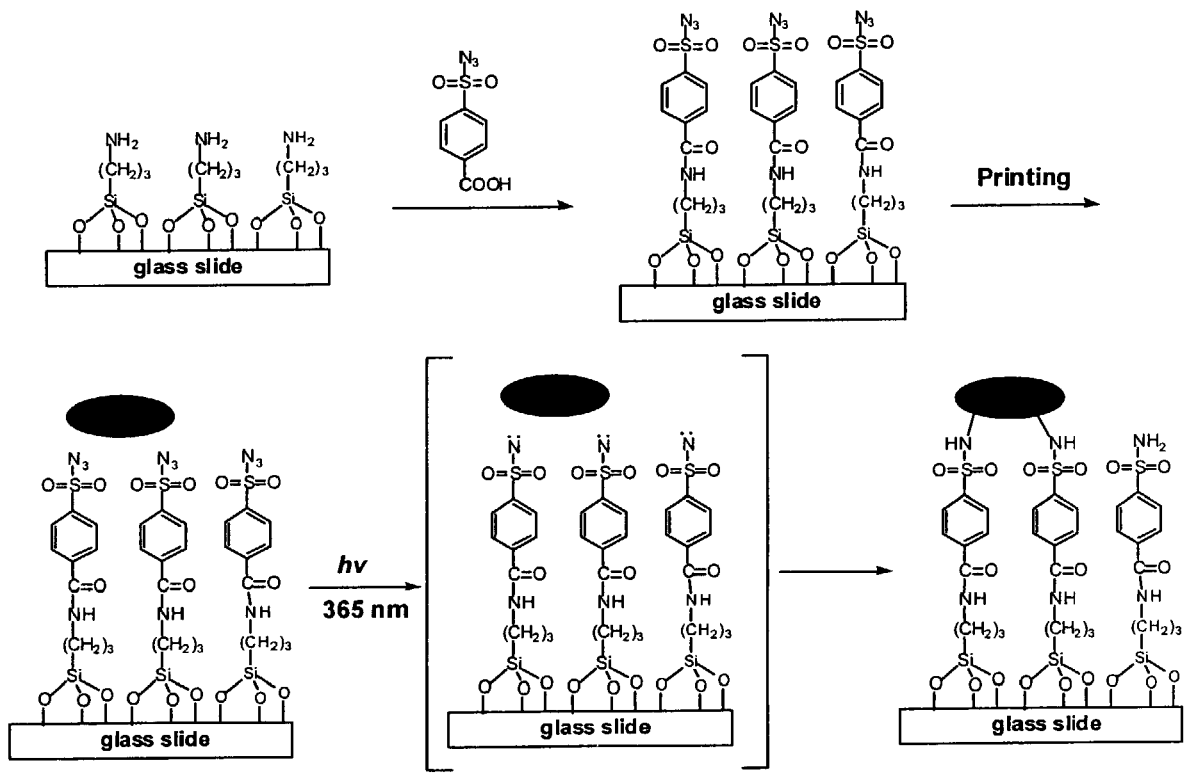
FIG. 23 shows the use of photocapture chemistry to immobilize compounds onto a solid support.
Figure 24:
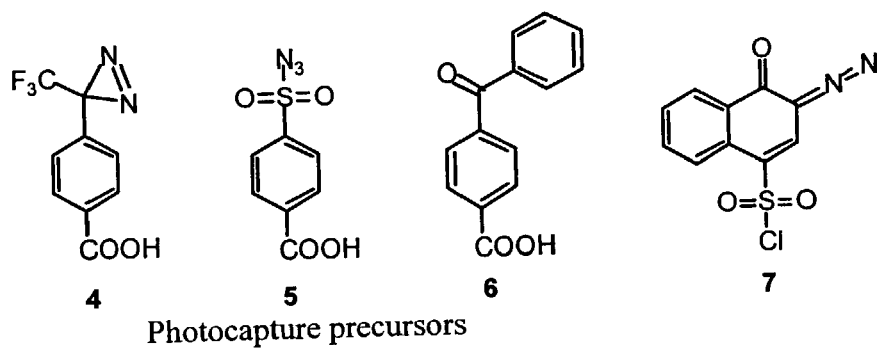
FIG. 24 depicts various exemplary photocapture precursors.

In another aspect, compounds are attached to the solid support using photocapture chemistry. The surface of the support is first modified with a photoactivatable precursor as shown in FIG. 23. An active species is then generated from these attached precursors by irradiation (e.g., UV light). In certain embodiments, long wavelength UV light at 365 nm is used to generate the active species. The active species may be carbene generated in situ from a diazirine (4 in FIG. 24); a stabilized nitrene from a suflonazide (5 in FIG. 24); or an activated carbonyl carbon from a benzophenone (6 in FIG. 24). These reactive species can randomly insert into the C—H, N—H, O—H, or other bonds of the compounds to be attached to the support. The insertion reaction allows for the immobilization of compounds printed on the surface of a support. This immobilization technique has the advantage of not requiring any common functional handle for covalent attachment. In another embodiment, a ketene from an α-diazoketone may be used to provide a more specific linkage to phenolic compounds or compounds with nucleophilic functional groups (7 in FIG. 24). In general photocapture chemistry provides more universal immobilization of compounds without the need for a common functional handle.

Methods for Detecting Biological Activity

It will be appreciated by one of ordinary skill in the art that the generation of arrays of compounds having extremely high spatial densities facilitates the detection of binding and/or activation events occurring between compounds in a specific chemical library and biological macromolecules. Thus, the present invention provides, in yet another aspect, a method for identifying small molecule partners for biological macromolecules of interest. The partners may be compounds that bind to particular macromolecules of interest and are capable of activating or inhibiting the biological macromolecules of interest. In general, this method involves (1) providing an array of one or more types of compounds, as described above, wherein the array of small molecules has a density of at least 1000 spots per $cm^2$; (2) contacting the array with one or more types of biological macromolecules of interest; and (3) determining the interaction of specific small molecule-biological macromolecule partners.

It will also be appreciated that the arrays of the present invention may be utilized in a variety of ways to enable detection of interactions between small molecules and biological macromolecules. In one particularly preferred embodiment, an array of different types of chemical compounds attached to the surface is utilized and is contacted by one or a few types of biological macromolecules to determine which compounds are capable of interacting with the specific biological macromolecule(s). As one of ordinary skill in the art will realize, if more than one type of compound is utilized, it is desirable to utilize a method for encoding each of the specific compounds so that a compound having a specific interaction can be identified. Specific encoding techniques have been recently reviewed and these techniques, as well as other equivalent or improved techniques, can be utilized in the present invention (see, Czarnik, A. W. *Current Opinion in Chemical Biology* 1997, 1, 60; incorporated herein by reference). Alternatively the arrays of the present invention may comprise one type of chemical compound and a library of biological macromolecules may be contacted with this array to determine the ability of this one type of chemical compound to interact with a variety of biological macromolecules. As will be appreciated by one of ordinary skill in the art, this embodiment requires the ability to separate regions of the support, utilizing paraffin or other suitable materials, so that the assays are localized.

As one of ordinary skill in the art will realize, the biological macromolecule of interest may comprise any biomolecule. In preferred embodiments, the biological macromolecule of interest comprises a protein, and more preferably the array is contacted with a library of recombinant proteins of interest. In yet another preferred embodiment, the biological molecules of interest are provided in the form of cell lysates such as those of tumor-associated cells. As will be appreciated by one of ordinary skill in the art, these proteins may comprise purified proteins, pools of purified proteins, and complex mixtures such as cell lysates, and fractions thereof, to name a few. Examples of particularly preferred biological macromolecules to study include, but are not limited to those involved in signal transduction, dimerization, gene regulation, cell cycle and cell cycle checkpoints, and DNA damage checkpoints. Furthermore, the ability to construct libraries of expressed proteins from any organism or tissue of interest will lead to large arrays of recombinant proteins. The compounds of interest may be capable of either inactivating or activating the function of the particular biomolecule of interest.

Each of the biological macromolecules may be modified to enable the facile detection of these macromolecules and the immobilized compounds. This may be achieved by tagging the macromolecules with epitopes that are subsequently recognized, either directly or indirectly, by a different receptor (e.g., an antibody) that has been labeled for subsequent detection (e.g., with radioactive atoms, fluorescent molecules, colored compounds, or enzymes that enable color formation, or light production, to name a few). Alternatively, the macromolecules themselves may be labeled directly using any one or other of these methods or not labeled at all if an appropriate detection method is used to detect the bound protein (e.g., mass spectrometry, surface plasmon resonance, and optical spectroscopy, to name a few).

In a particularly preferred embodiment, the inventive arrays are utilized to identify compounds for chemical genetic research. In classical genetics, either inactivating (e.g., deletion or "knock-out") or activating (e.g., oncogenic) mutations in DNA sequences are used to study the function of the proteins that are encoded by these genes. Chemical genetics instead involves the use of small molecules that alter the function of proteins to which they bind, thus either inactivating or activating protein function. This, of course, is the basis of action of most currently approved small molecule drugs. The present invention involves the development of "chip-like" technology to enable the rapid detection of interactions between small molecules and specific proteins of interest. The examples presented below demonstrate how the methods and compositions of the present invention can be used to identify new small molecule ligands for use in chemical genetic research. One of ordinary skill in the art will realize that the inventive compositions and methods can be utilized for other purposes that require a high density chemical compound format.

As will also be appreciated by one of ordinary skill in the art, arrays of chemical compounds may also be useful in detecting interactions between the compounds and alternate classes of molecules other than biological macromolecules. For example, the arrays of the present invention may also be useful in the fields of catalysis and materials research to name a few.

These and other aspects of the present invention will be further appreciated upon consideration of the following Examples, which are intended to illustrate certain particular embodiments of the invention but are not intended to limit its scope, as defined by the claims.

EXAMPLES

Example 1

Small Molecule Printing Using Michael Addition

Figure 6:
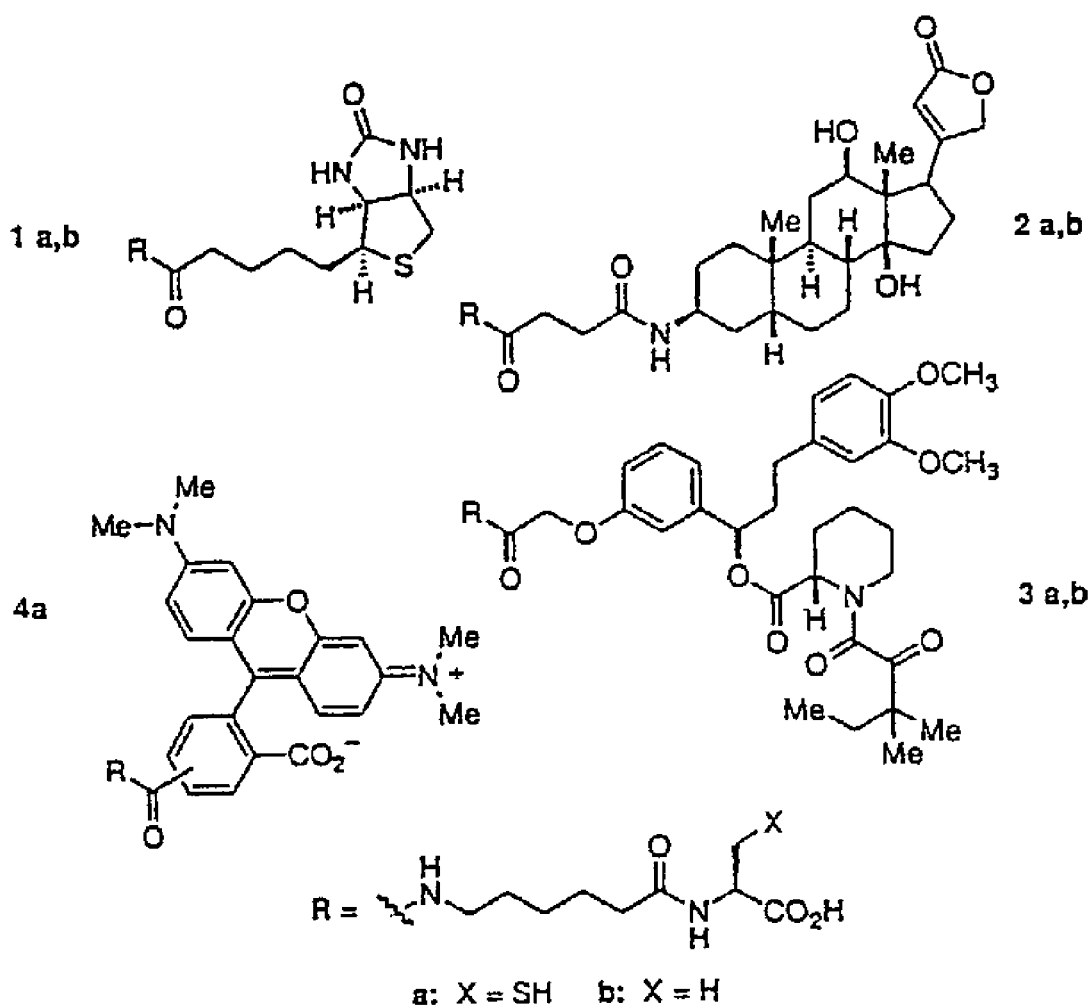
FIG. 6 depicts test compounds used to demonstrate the concept of small molecule printing.

In order to demonstrate the utility of small molecule printing as a technique identifying small molecule-protein interactions, three unrelated molecules were chosen for which specific protein receptors are available. Compound 1 (FIG. 6, R=OH) is the vitamin biotin, which is recognized by the bacterial protein streptavidin (Chaiet et al., *Arch. Biochem. Biophys.* 1964, 106, 1; incorporated herein by reference). Compound 2 (R=OH) is a derivative of the steroid digoxigenin and is recognized by the mouse monoclonal antibody DI-22 (Sigma). Finally, compound 3 (R=OH) is a synthetic pipecolyl α-ketoamide, which was designed to be recognized by the human immunophilin FKBP12 (Holt et al., *J. Am. Chem. Soc.* 1993, 115, 9925; incorporated herein by reference). Each of these compounds was attached to 400-450 μm diameter polystyrene beads (estimated capacity of 20 nmol per bead) via a 6-aminocaproic acid linker and either 4-methoxytrityl-protected cysteine (FIG. 6, X=S(Mmt)) or alanine (FIG. 6, X=H; negative control). To create reference points on the slides, beads were also prepared with a thiol-labeled derivative of the fluorescent dye tetramethylrhodamine (4a). Individual beads were placed in 28 separate wells of a 96-well plate and the compounds were deprotected, cleaved, and subsequently dissolved in 5 μL of DMF. The released compounds were then arrayed robotically onto a series of maleimide-derivatized glass slides with a distance of 300 μm between the centers of adjacent spots. Each slide was printed according to the pattern illustrated in FIG. 7D. Following a 12 hour room temperature incubation, the slides were washed extensively and probed with different proteins.

The slide in FIG. 7A was probed with Cy5-conjugated streptavidin, washed, and subsequently scanned using an ArrayWoRx fluorescence slide scanner. The slide was scanned for both tetramethylrhodamine fluorescence (false-colored green) and Cy5 fluorescence (false-colored red). As anticipated, only the spots containing 1a were visible when scanned for Cy5 fluorescence, indicating that localization of streptavidin on these spots was both specific for biotin and dependent on the thiol functionality (compound 1b, which lacks a thiol, does not attach to the slide). Using a two-step detection method, the slide in FIG. 7B was probed first with DI-22 and then with a Cy5-conjugated goat-anti-mouse antibody (which recognizes DI-22). As anticipated, the Cy5 fluorescence localized to the 2a-containing spots. Finally, the slide in FIG. 7C was probed using a three-step method: $(His)_6$-FKBP12 followed by mouse-anti-RGS$(His)_6$ antibody followed by Cy5-conjugated goat-anti-mouse antibody. As before, the fluorescence localized to the appropriate spots.

Figure 7:
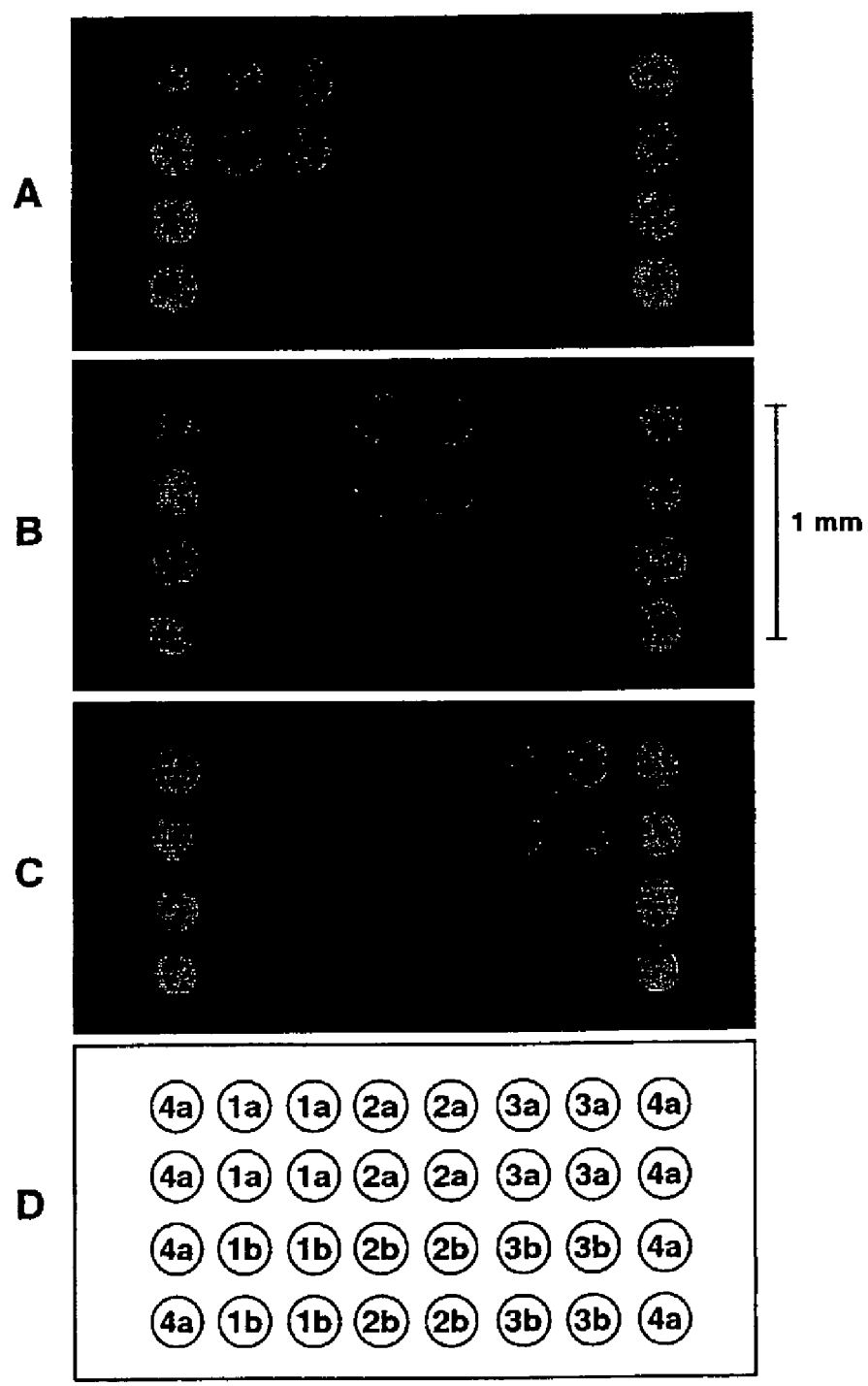
FIG. 7 depicts small molecules printed on maleimide-derivatized glass slides and detected with fluorophore-conjugated proteins. Compounds were printed according to the pattern illustrated in panel (D). Yellow circles indicate thiol-derivatized small molecule. (A) indicates a slide detected with Cy5-streptavidin. (B) indicates a slide detected with DI-22 followed by Cy5-goat-anti-mouse antibody. (C) indicates a slide detected with RGS (His)$_6$-FKBP12 followed by mouse-anti-RGS (His)$_6$ antibody followed by Cy5-goat-anti-mouse antibody.
Figure 8:
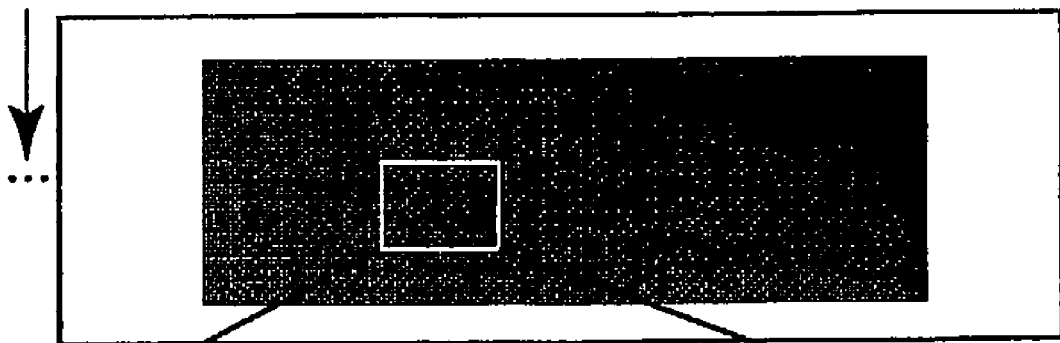
FIG. 8 depicts small molecules printed on a maleimide-derivatized glass slide and detected with FITC-streptavidin (blue), Cy3-DI-22 (green), and Cy5-FKBP12 (red). The full slide contains 10,800 distinct spots and was prepared using only one bead for each of the three small molecules printed (1a, 2a, and 3a as shown in FIG. 6).
Figure 8:
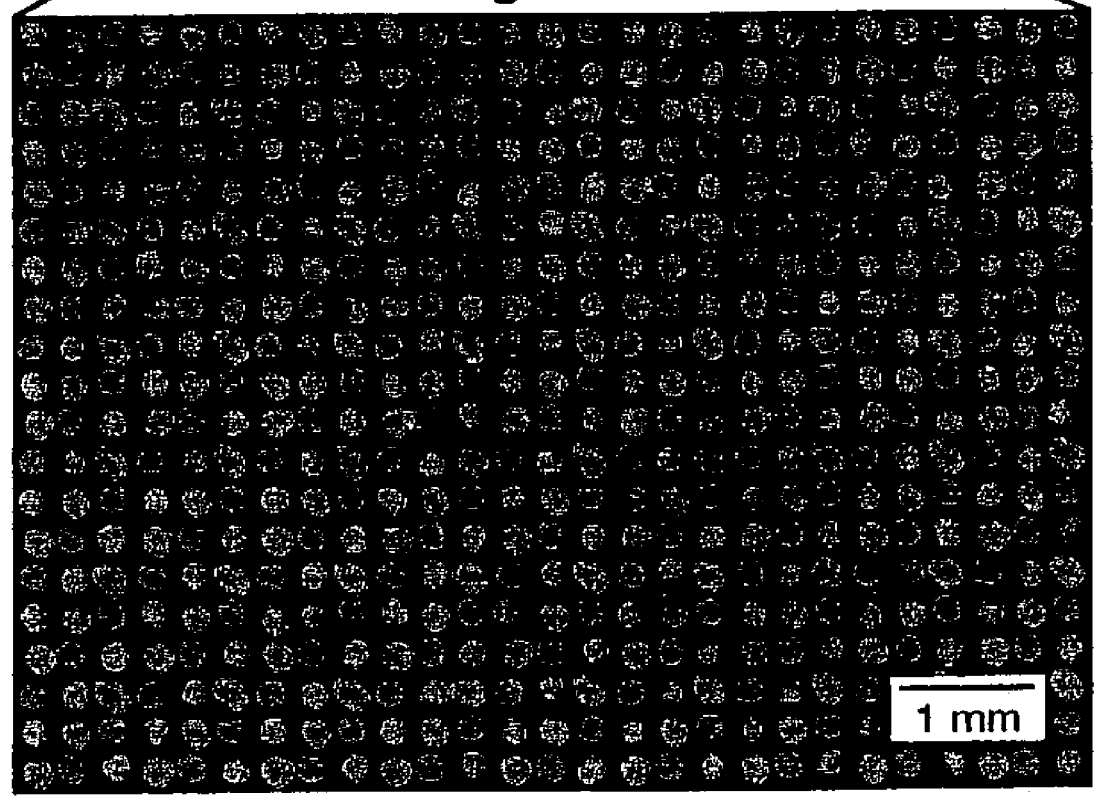

These results clearly illustrate both the high selectivity and remarkable sensitivity of this slide-based assay. To illustrate the highly parallel nature of small molecule printing, compound 1a was released from a single 400-450 μm diameter polystyrene bead and the released compound was dissolved in 10 μL of DMF. We repeated this procedure for compounds 2a and 3a. Using the microarraying robot, these three compounds were repetitively spotted in an alternating pattern on a single maleimide-derivatized slide, using the same spatial density as in FIG. 7. Each compound was spotted 3600 times, using less than half of the compound from each bead (~1 nL per spot) and yielding 10,800 distinct spots. The slide was then probed in a single step with a solution containing FITC-conjugated streptavidin, Cy3-conjugated DI-22, and Cy5-conjugated FKBP12. Following a brief washing step, the slide was scanned for FITC fluorescence (false colored blue), Cy3 fluorescence (false-colored green), and Cy5 fluorescence (false-colored red). As shown in FIG. 8, the three differently labeled proteins localized to the spots containing their cognate ligands.

Experimental details for the above described example can be found in below. One of ordinary skill in the art will realize that the inventive compositions and methods are not limited to the examples described above; rather the present invention is intended to include all equivalents thereof.

Example 2

Small Molecule Printing Using Silylation Reaction

Figure 9:
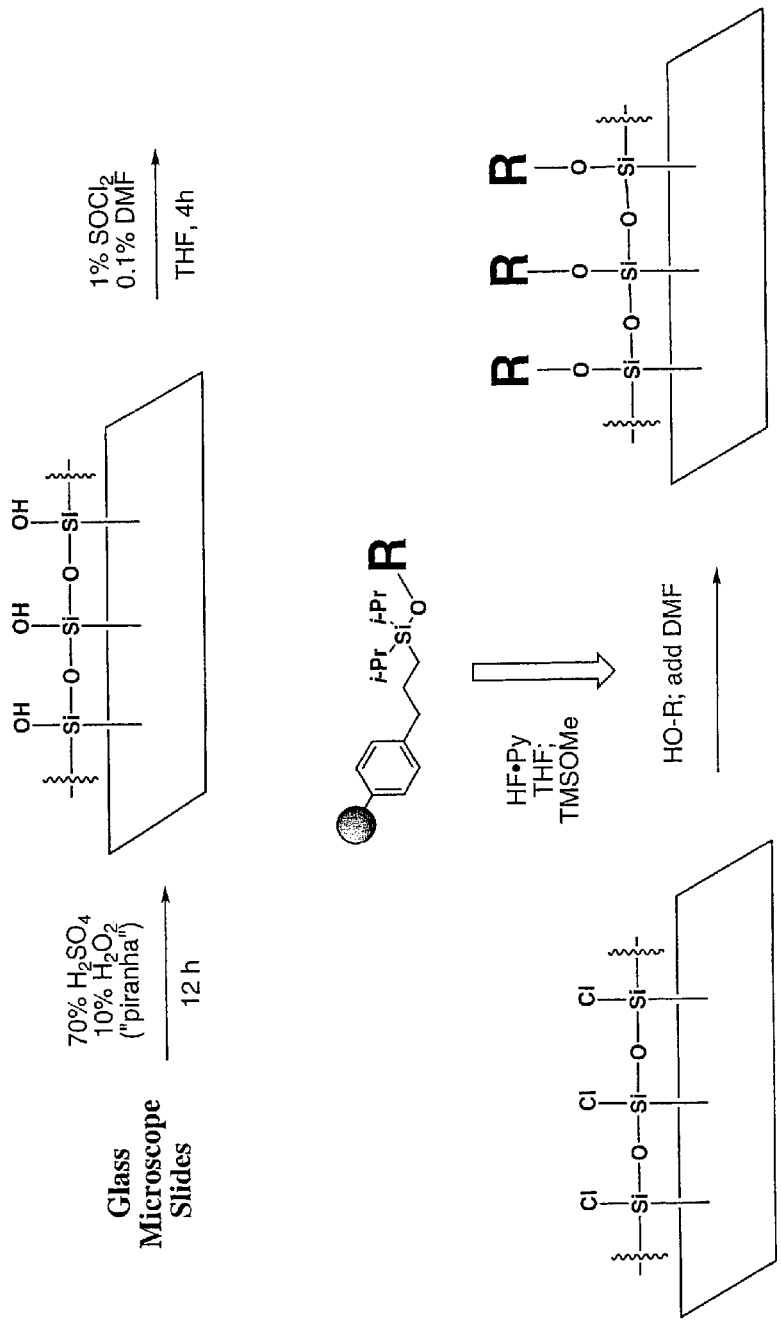
FIG. 9 shows the activation of glass slides for the covalent attachment of alcohols.

Standard glass slides were activated for selective reaction with alcohols (FIG. 9). Microscopic slides were first treated with a $H_2SO_4/H_2O_2$ solution ("piranha") for 16 hours at room temperature. After extensive washing with water, the slides were treated with thionyl chloride and a catalytic amount of DMF in THF for 4 hours at room temperature. Surface characterization by x-ray photoelectron spectroscopy (XPS) confirmed the presence of chlorine on the slide (Strother et al., *J. Am. Chem. Soc.*, 2000, 122, 1205-1209; incorporated herein by reference). To test the ability of these chlorinated slides to capture alcohols released from synthesis beads, we initially used three alcohol-containing small molecules and a bead linker reagent developed for chemical genetic applications of diversity-oriented synthesis.

Figure 10:
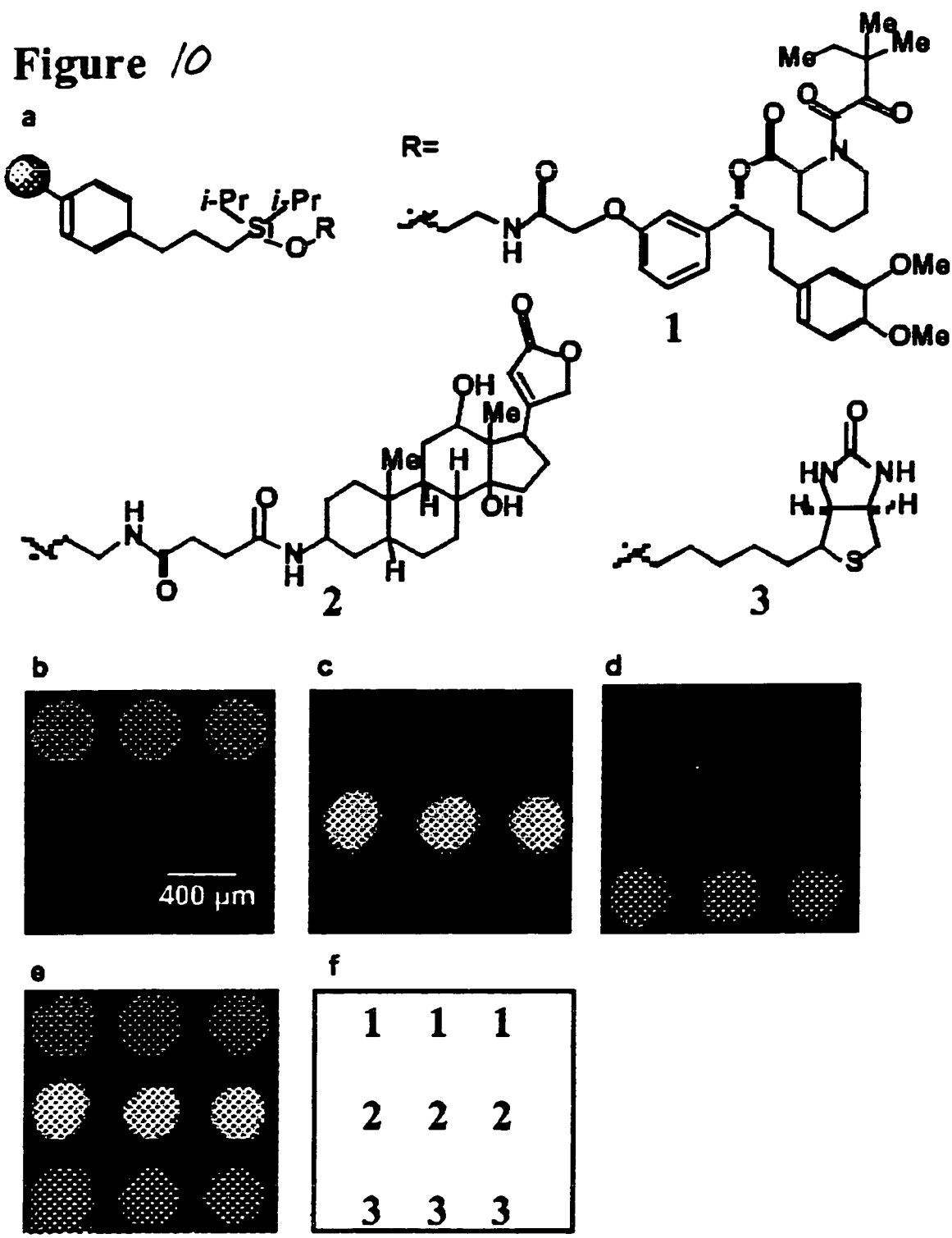
FIG. 10 shows a) alcohols attached to 500-560 μm polystyrene resin through a silyl-containing linker; b-e) a nine spot microarray printed according to the pattern in 6f and visualized in the following channels: b) Cy5 (false-colored red), c) Cy3 (false-colored green), d) FITC (false-colored purple), e) Cy5, Cy3, and FITC. Average distance between spots=400 μm; average spot diameter=300 μm.

Primary alcohol derivatives of a synthetic α-ketoamide (Holt et al., *J. Am. Chem. Soc.* 1993, 115, 9925-9938; incorporated herein by reference), digoxigenin, and biotin were attached to silicon linker-modified beads (FIG. 10). These beads are high capacity 500-560 µm polystyrene beads equipped with an all hydrocarbon and silicon linker for the temporary attachment and eventual fluoride-mediated release of synthetic, alcohol-containing compounds. The three primary alcohol derivatives have known protein partners, namely FKBP12 (Harding et al., *Nature*, 1989, 341, 758-760; Siekierkea et al., *Nature*, 1989, 341, 755-757; each of which is incorporated herein by reference), the DI-22 antibody (Sigma), and streptavidin (Chaiet et al., *Arch. Biochem. Biophys.*, 1964, 106, 1-5; incorporated herein by reference), respectively. After HF-pyridine-mediated release from the beads and subsequent solvent removal, the compounds were dissolved in 5 µL of DMF in individual wells of 96-well plates to give ~5 mM solutions. A microarrayer was used to spot the compounds (in triplicate) 400 µm apart (average spot diameter of 300 µm) onto the thionyl chloride-activated slides (FIG. 10b-e) and the slides were then washed extensively with DMF, THF, isopropanol, and an aqueous buffer. As shown, when binding was detected separately (FIG. 10b-d) or simultaneously (FIG. 10e), the recognition of the protein for its ligand was efficient and selective. When the same compounds were printed onto control slides (i.e., not activated with thionyl chloride) no protein-ligand interactions were detected.

Figure 11:
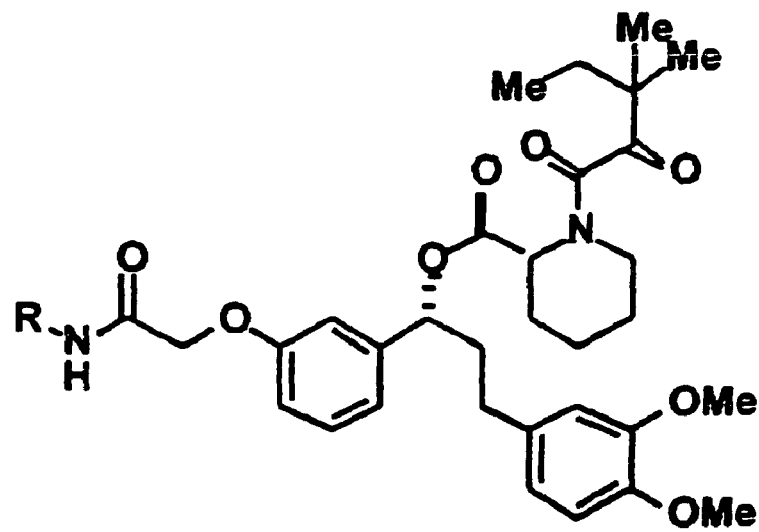
FIG. 11 shows a microarray of primary, secondary, phenolic, and methyl ester derivatives of an FKBP ligand. Slides were probed with Cy5-labeled FKBP (false-colored red).
Figure 11:
Figure 11:
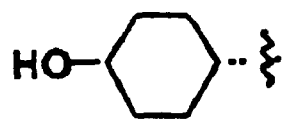
Figure 11:
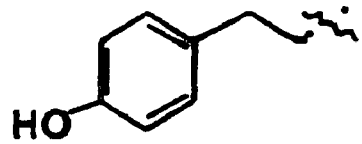
Figure 11:
Figure 11:
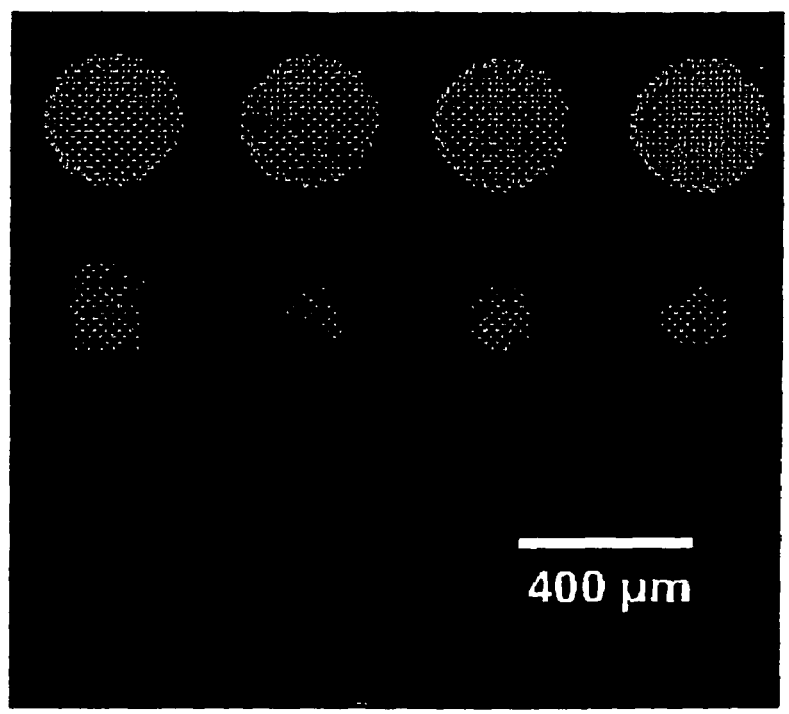

Small molecules resulting from diversity-oriented syntheses can contain a wide array of functional groups, including secondary and phenolic hydroxyls. To test the ability of such functionalities to react with the thionyl chloride activated slides, the synthetic α-ketoamide derivatives shown in FIG. 11 were synthesized. An array was then printed (in quadruplicate) containing the primary, secondary, phenolic, and methyl ether derivatives at ~5 mM, and probed with Cy5-FKBP. As shown in FIG. 11, the reaction of the primary alcohol is favored, and this bias holds even when the secondary, phenolic, and methyl ether derivatives are arrayed at a concentration ten times greater than the primary.

Figure 12:
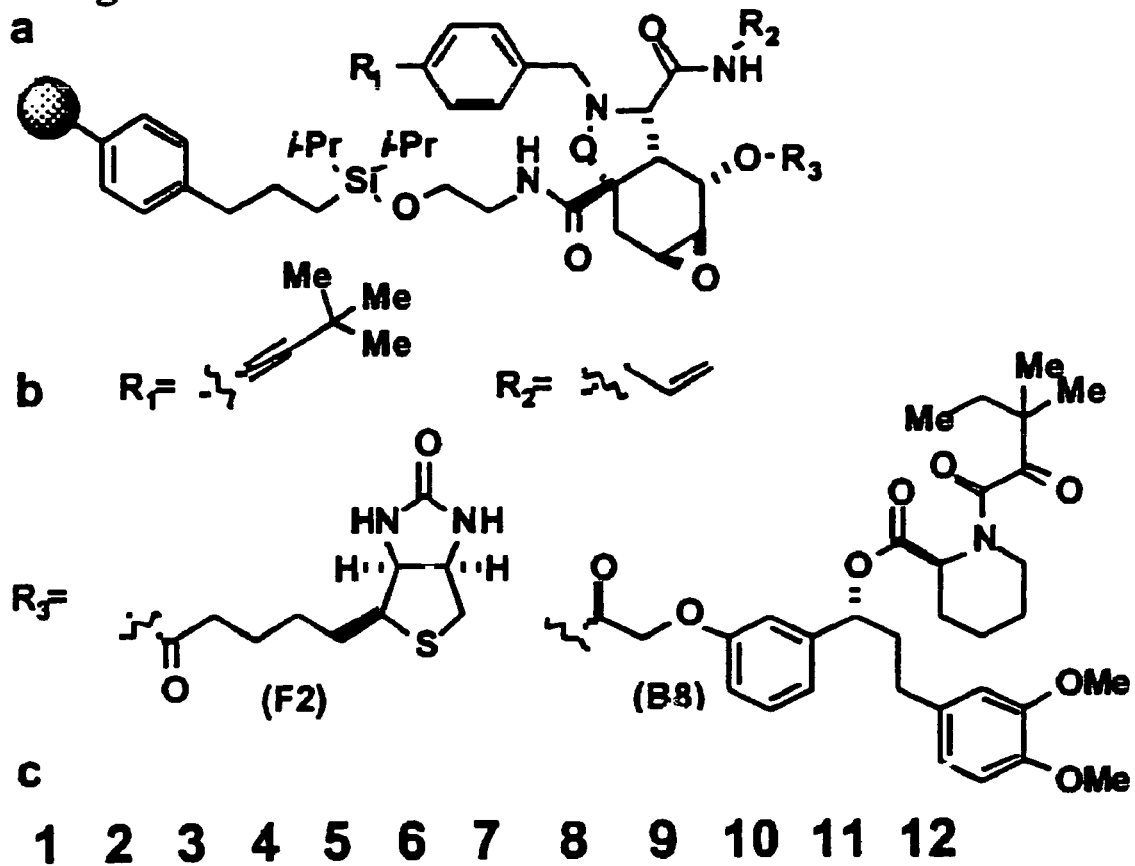
FIG. 12 shows a) the general structure of a small-molecule library, 78 members of which were placed in the wells of a 96-well plate; b) the structure of two additional 'tagged' library members; c) alcohol microarray onto which 78 members of the small molecule library and two tagged members were printed. Protein binding detected with Cy5-FKBP (false-colored red) and FITC-streptavidin (false-colored green).
Figure 12:
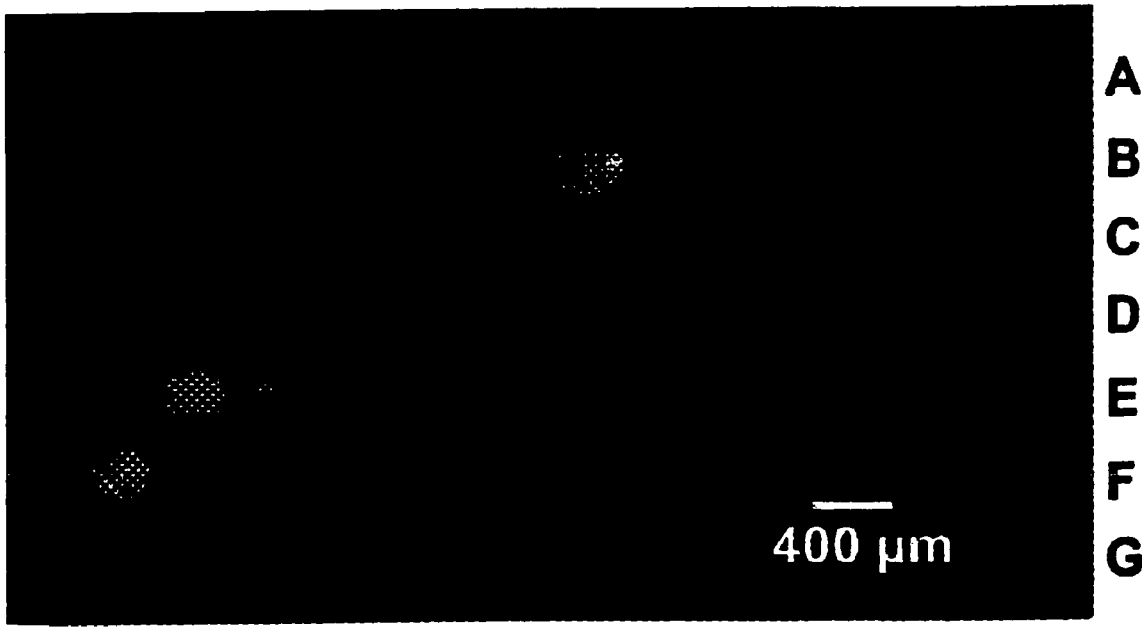

As a demonstration of the compatibility of this alcohol arraying technique with split-pool synthesis, a collection of 78 small molecules derived from such synthesis having the general structure shown in FIG. 12a was printed onto glass slides (Tan et al., *J. Am. Chem. Soc.* 1998, 120, 8565-8566; incorporated herein by reference). To this collection were added two members that had been acylated with the synthetic α-ketoamide derivative or biotin (FIG. 12b). These 'tagged' members were then released from their beads, dissolved in 5 µL of DMF, and placed in known wells of a 96-well plate. After placing the 80 compounds into discrete wells, the entire plate was arrayed onto thionyl chloride/DMF activated slides, which were then probed with fluorescently-labeled proteins, Cy5-FKBP12 and FITC-streptavidin. The results (FIG. 12c) show that two spots in the array fluoresce in the Cy5 channel (false-colored red), and another fluoresces in the FITC channel (false-colored green). The positional encoding confirms the result that the compound acylated with the α-ketoamide was spotted in B8, and the compound acylated with biotin was spotted in F2. The spot visible in E3 is an apparent serendipitous and reproducible 'hit', and awaits further analysis. Thus, this experiment demonstrates the process of split-pool synthesis, release from the solid support, arraying onto glass slides, and detection/visualization of protein-small molecule binding events.

Example 3

Fabrication of Custom Slide Reaction Vessels

Figure 13:
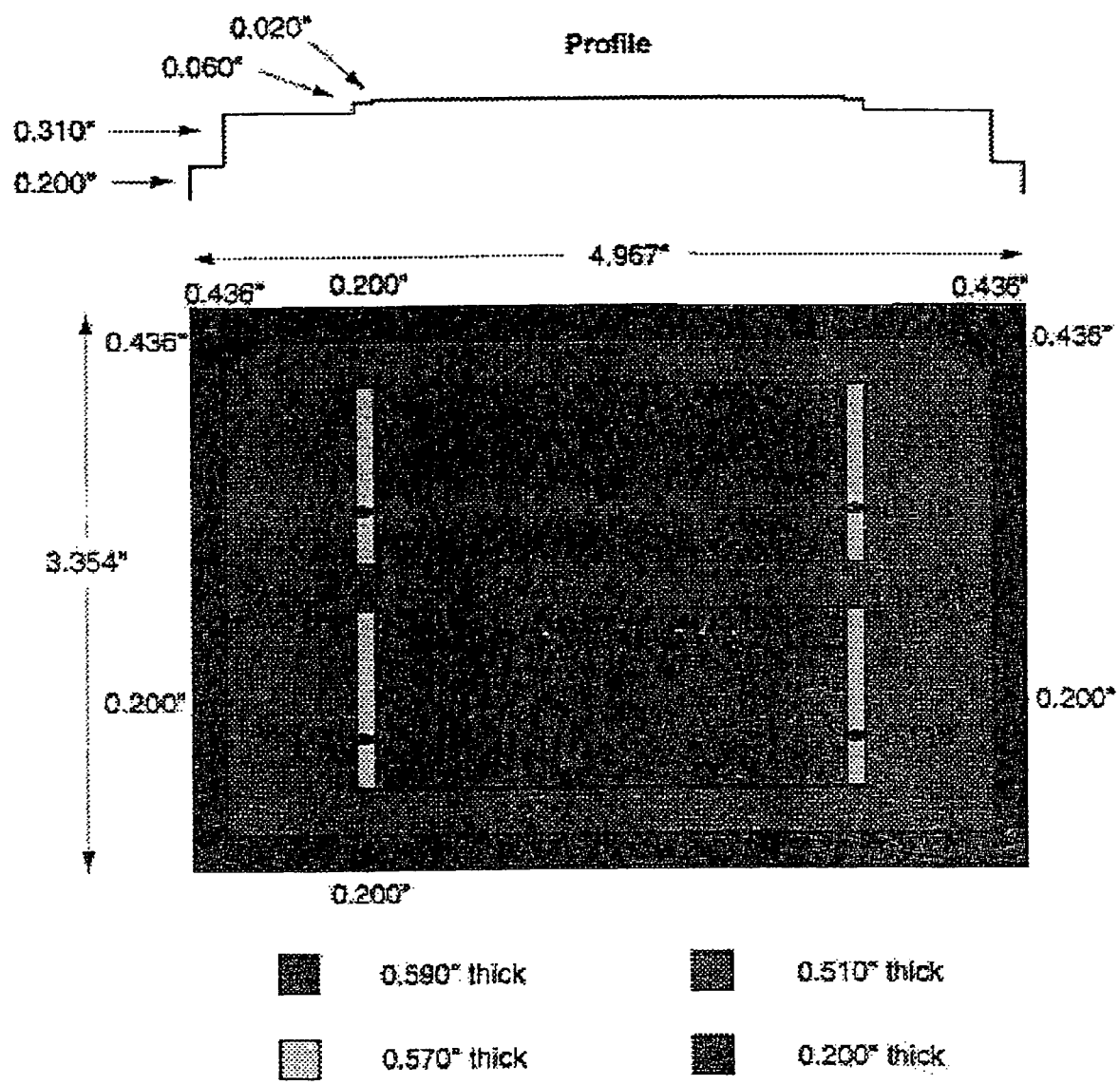
FIG. 13 shows the master template used to fabricate custom slide-sized reaction vessels that enable the uniform application of ~1.4 mL solution to one face of a 2.5 cm×7.5 cm slide.
Figure 14:
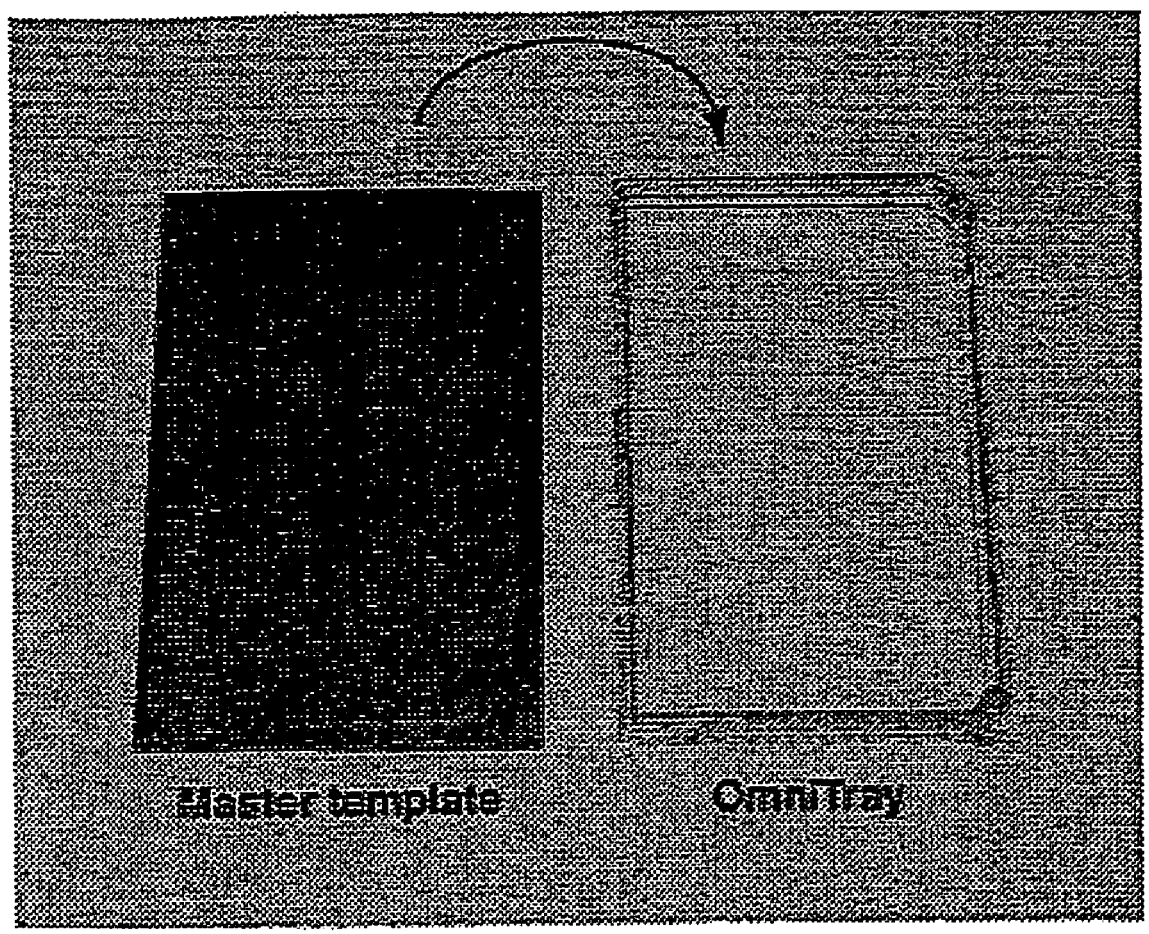
FIG. 14 shows the method of making the slide-sized reaction vessels by the following steps: 1) add PDMS prepolymer to OmniTray (~50 g); 2) insert master template face down into OmniTray; 3) cure polymer at 65° C. for 4 h; and 4) peel PDMS polymer away from the master template.

In an effort to minimize reagent volume during the chemical treatment of glass microscope slides, we designed and fabricated custom slide-sized reaction vessels that enable the uniform application of ~1.4 mL solution to one face of a 2.5 cm×7.5 cm slide. First, a master template mold was cut from a block of Delhran plastic according to the blueprint shown in FIG. 13. The slide-sized reaction vessels were prepared by casting degassed polydimethysiloxane (PDMS, Sylgard Kit 184, Dow corning, Midland, Mich.) prepolymer around the master template in a polystyrene OmniTray (Nalge Nunc International, Naperville, Ill.). After curing for four hours at 65° C., the polymer was peeled away from the master to give the finished product (FIG. 14).

Figure 15:
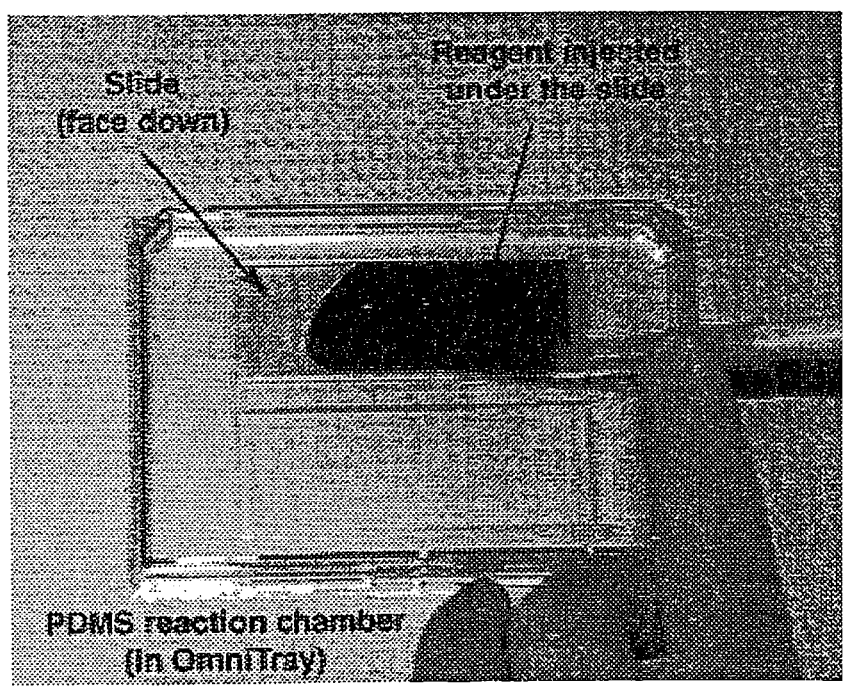
FIG. 15 shows the application of reagent to one surface of a slide.

To use the vessels, slides were placed face-down as illustrated below and reagent was injected under the slides with a P1000 Pipetman (FIG. 15).

Example 4

Chemical Derivatization of Glass Microscope Slides

Plain glass slides (VWR Scientific Products, USA) were cleaned in a "piranha" solution (70:30 v/v mixture of concentrated $H_2SO_4$ and 30% $H_2O_2$) for 12 hours at room temperature. (Caution: "piranha" solution reacts violently with several organic materials and should be handled with extreme care (Pintochovski et al., *Electrochem. Soc.* 1979, 126, 1428; Dobbs et al., *Chem. Eng. News* 1990, 68(17), 2; Wnuk, *Chem. Eng. News* 1990, 68(26), 2; Erickson, *Chem. Eng. News* 1990, 68(33), 2; each of which is incorporated herein by reference)). After thorough rinsing with distilled water, the slides were treated with a 3% solution of 3-aminopropyltriethoxysilane (United Chemical Technologies, Bristol, Pa.) in 95% ethanol for 1 hour. (Before treating the slides, the 3% silane solution was stirred for at least 10 minutes to allow for hydrolysis and silanol formation). The slides were then briefly dipped in 100% ethanol and centrifuged to remove excess silanol. The adsorbed silane layer was cured at 115° C. for one hour. After cooling to room temperature, the slides were washed several times in 95% ethanol to remove uncoupled reagent.

A simple, semi-quantitative method was used to verify the presence of amino groups on the slide surface (Licitra et al., Proc. Natl. Acad. Sci. USA 1996, 93, 12817-12821; incorporated herein by reference). One glass slide from each batch of amino-functionalized slides was washed briefly with 5 mL of 50 mM sodium bicarbonate, pH 8.5. The slide was then dipped in 5 mL of 50 mM sodium bicarbonate, pH 8.5 containing 0.1 mM sulfo-succinimidyl-4-O-(4,4'-dimethoxytrityl)-butyrate (s-SDTB; Pierce, Rockford, Ill.) and shaken vigorously for 30 minutes. (The s-SDTB solution was prepared by dissolving 3.03 mg of s-SDTB in 1 mL of DMF and diluting to 50 mL with 50 mM sodium bicarbonate, pH 8.5). After a 30 minute incubation, the slide was washed three times with 20 mL of distilled water and subsequently treated with 5 mL of 30% perchloric acid. The development of an orange-colored solution indicated that the slide had been successfully derivatized with amines; no color change was seen for untreated glass slides. Quantitation of the 4,4'-dimethoxytrityl cation $\epsilon_{498nm}=70,000$ $M^{-1}$ $cm^{-1}$) released by the acid treatment indicated an approximate density of two amino groups per $nm^2$.

The resulting amino-functionalized slides were transferred to custom slide-sized polydimethylsiloxane (PDMS) reaction vessels (as described in Example 3). One face of each slide was treated with 20 mM N-succinimidyl 3-maleimido propionate (Aldrich Chemical Co., Milwaukee, Wis.) in 50 mM sodium bicarbonate buffer, pH 8.5, for three hours. (This solution was prepared by dissolving the N-succinimidyl 3-maleimido propionate in DMF and then diluting 10-fold with buffer). After incubation, the plates were washed several times with distilled water, dried by centrifugation, and stored at room temperature under vacuum until further use.

Example 5

Attachment of Small Molecules to Polystyrene Beads

Materials. Fmoc-eAhx-OH and PyBOP® were from Novabiochem (San Diego, Calif.). Biotin and diisopropylethylamine (DIPEA) were from Aldrich Chemical Co. (Milwaukee, Wis.). 3-Amino-3-deoxydigoxigenin hemisuccinamide, succinimidyl ester and 5(6)-TAMRA, SE were from Molecular Probes (Eugene, Oreg.). Wash solvents were obtained from Mallinckrodt or E. Merck and used as received. Anhydrous dimethylformamide (DMF) was obtained from Aldrich Chemical Co. in SureSeal™ bottles.

The "FKBP Ligand" is shown below and was synthesized as published (Keenan et al., Bioorg. Med. Chem. 1998, 6, 1309; Amara et al., Proc. Natl. Acad. Sci. USA 1997, 94, 10618-10623; each of which is incorporated herein by reference).

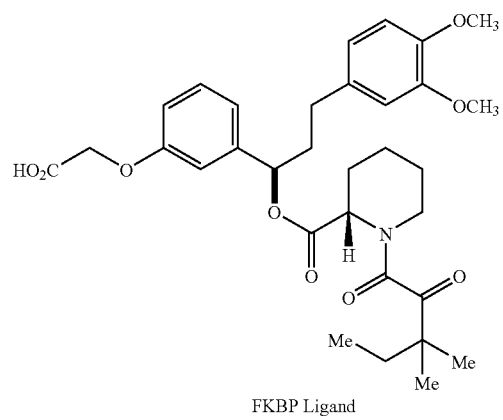

FKBP Ligand

Polystyrene synthesis beads were obtained by custom synthesis from Rapp Polymere (Tübingen, Germany). They ranged from 400 μm to 450 μm in diameter, had an estimated capacity of about 0.4 mmol/g (17 nmol/bead), and came functionalized as indicated below.

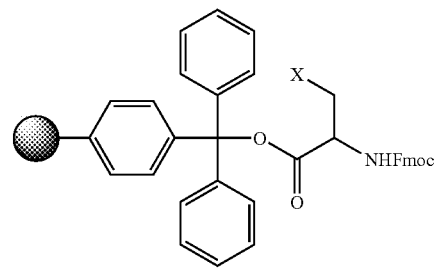

Polystyrene A Trt-Cys(Mmt) Fmoc: X = S(Mmt)
Polystyrene A Trt-Ala Fmoc: X = H

Solid Phase Reactions. Solid phase reactions were performed in either 2 mL fritted polypropylene Biospin® chromatography columns (Pharmacia Biotech, Uppsala, Sweden) or 10 mL fritted polypropylene PD-10 columns (Pharmacia Biotech). Resin samples were washed on a Val-Man® Laboratory Vacuum Manifold (Promega, Madison, Wis.) using the following procedure: 3×DMF, 3×THF, 3×DMF, 3×THF, 3×DMF, 3×THF, 3×DMF, 6×$CH_2Cl_2$, 3×THF.

Polystyrene Beads with Attached Linker (5c, 5d)

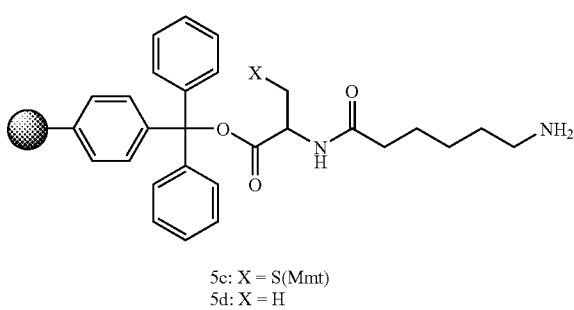

5c: X = S(Mmt)
5d: X = H

Either Polystyrene A Trt-Cyc(Mmt) Fmoc or Polystyrene A Trt-Ala Fmoc (400 mg, 0.4 mmol/g, 0.16 mmol) was placed in a 10 mL column and swollen with 6 mL DMF for 2 min. The column was drained and the Fmoc group removed by two 15 min treatments with 6 mL of 20% piperidine in DMF. The resin was washed (as described above), dried under vacuum, and swollen with 6 mL anhydrous DMF for 2 min. The column was drained and the resin swollen with 6 mL distilled CH₂Cl₂ for another 2 min. The column was drained and a mixture containing anhydrous DMF (5.2 mL), Fmoc-eAhx-OH (283 mg, 0.80 mmol, 5 eq), PyBOP® (416 mg, 0.80 mmol, 5 eq), and DIPEA (279 µL, 160 mmol, 10 eq) was added. After 12 h, the resin was washed and found to be negative to Kaiser ninhydrin test. The Fmoc group was then removed (as above) and the resin washed to give 5c and 5d.

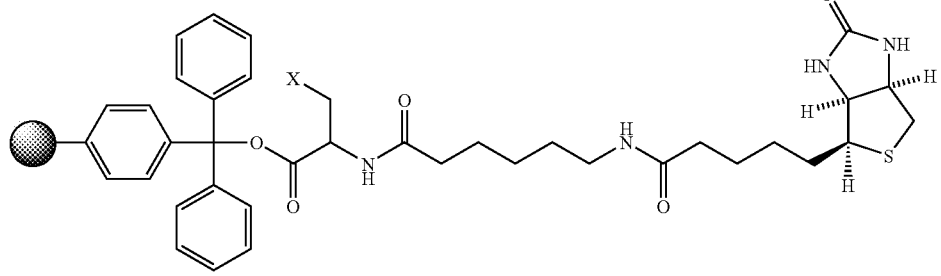

1c: X = S(Mmt)
1d: X = H

Either resin 5c or resin 5d (100 mg, 0.040 mmol, 1 eq) was placed in a 2 mL column and swollen with 1.5 mL anhydrous DMF for 2 min. The column was drained and the resin swollen with 1.5 mL distilled CH₂Cl₂ for another 2 min. The column was drained and a mixture containing anhydrous DMF (1.3 mL), biotin (39.1 mg. 0.16 mmol, 4 eq), PyBOP® (83.3 mg, 0.16 mmol, 4 eq), and DIPEA (55.7 µL, 0.32 mmol, 8 eq) was added. After 12 h, the resin was washed and subsequently found to be negative to Kaiser ninhydrin test.

Polystyrene Beads with Attached Linker and Digoxigenin Derivative (2c, 2d)

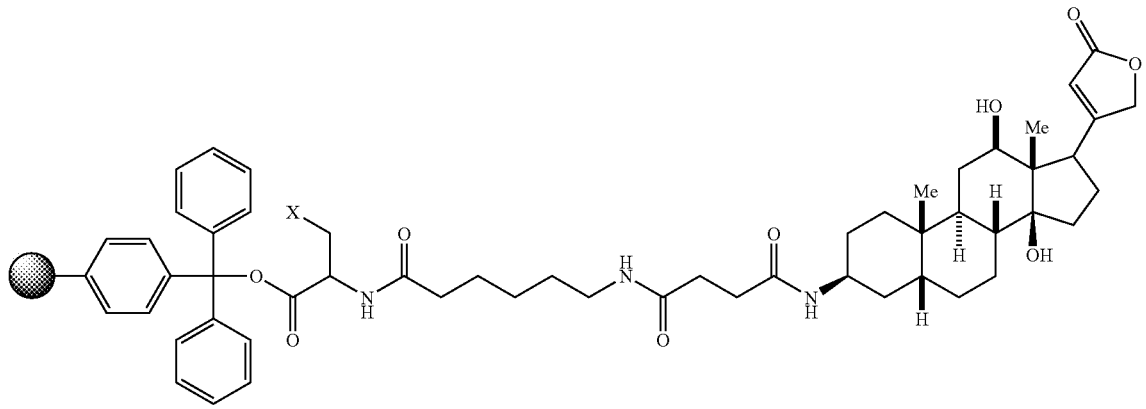

2c: X = S(Mmt)
2d: X = H

Either resin 5c or resin 5d (10 mg, 0.004 mmol, 1 eq) was placed in a 2 mL column and swollen with 1.5 mL anhydrous DMF for 2 min. The column was drained and the resin swollen with 1.5 mL distilled CH₂Cl₂ for another 2 min. The column was drained and a mixture containing anhydrous DMF (1.0 mL), 3-amino-3-deoxydigoxigenin hemisuccinamide, succinimidyl ester (5.0 mg, 0.0085 mmol, 2.1 eq), and DIPEA (20 µL, 0.115 mmol, 29 eq) was added. After 12 h, the resin was washed and treated for an additional 12 h with a fresh preparation of the mixture described above. The resin was washed again and subsequently found to be negative to Kaiser ninhydrin test.

Polystyrene Beads with Attached Linker and FKBP Ligand (3c, 3d)

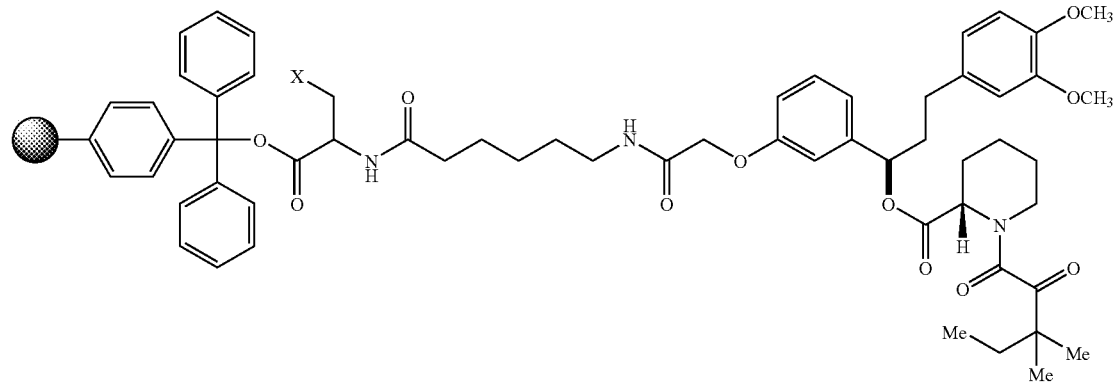

3c: X = S(Mmt)
3d: X = H

Either resin 5c or resin 5d (100 mg, 0.04 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.3 mL), FKBP ligand (67.5 mg, 0.116 mmol, 2.9 eq), PyBOP® (83.3 mg, 0.16 mmol, 4 eq), and DIPEA (55.7 μL, 0.32 mmol, 8 eq) was added. After 12 h, the resin was washed and subsequently found to be negative to Kaiser ninhydrin test.

Polystyrene Beads with Attached Linker and Tetramethylrhodamine Derivative (4c)

Mass Spectrometry. As confirmation of this standard coupling chemistry, about 10 beads each of 1c, 1d, 2c, 2d, 3c and 3d were exposed to 100 μL of trifluoroacetic acid/triisopropylsilane/chloroform (2:1:17) for 2 h at room temperature. The deprotection/cleavage solution was then removed in vacuo and the liberated compounds dissolved in 20 μL DMF. $FAB^+MS$ gave molecular weights that exactly matched those predicted for compounds 1a, 1b, 2a, 2b, 3a and 3b, respectively.

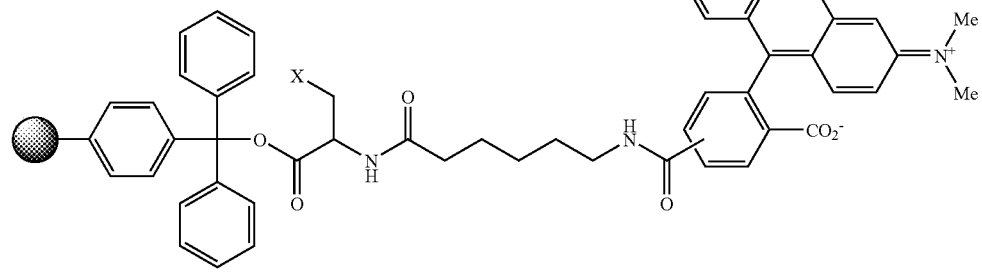

4c: X = S(Mmt)

Either resin 5c or resin 5d (40 mg. 0.016 mmol, 1 eq) was placed in a 2 mL column and swollen with 1.5 mL anhydrous DMF for 2 min. The column was drained and the resin swollen with 1.5 mL distilled $CH_2Cl_2$ for another 2 min. The column was drained and a mixture containing anhydrous DMF (1.0 mL), 5(6)-TAMRA, SE (25 mg, 0.047 mmol, 3.0 eq), and DIPEA (20 μL, 0.115 mmol, 7.2 eq) was added. After 12 h, the resin was washed and treated for an additional 12 h with a fresh preparation of the mixture described above. The resin was washed again to yield resin 4c.

Example 6

Small Molecule Printing

Deprotection and Release of Small Molecules. Individual beads (1c, 1d, 2c, 2d, 3c, 3d, 4c) were placed in separate wells of a polypropylene V-bottom 96-well plate (Costar, Corning, N.Y.) using an 18-gauge needle and a low power dissecting microscope. To each well was added 20 μL of trifluoroacetic acid/triethylsilane/chloroform (2:1:17) and the wells were immediately sealed with polyethylene strip caps (Nalge Nunc International, Naperville, Ill.). After 2 h at room temperature, the caps were discarded and the cleavage solution removed in vacuo. The released compounds were then dissolved in 5-10 µL of DMF and printed onto maleimide-derivatized glass slides.

Figure 16:
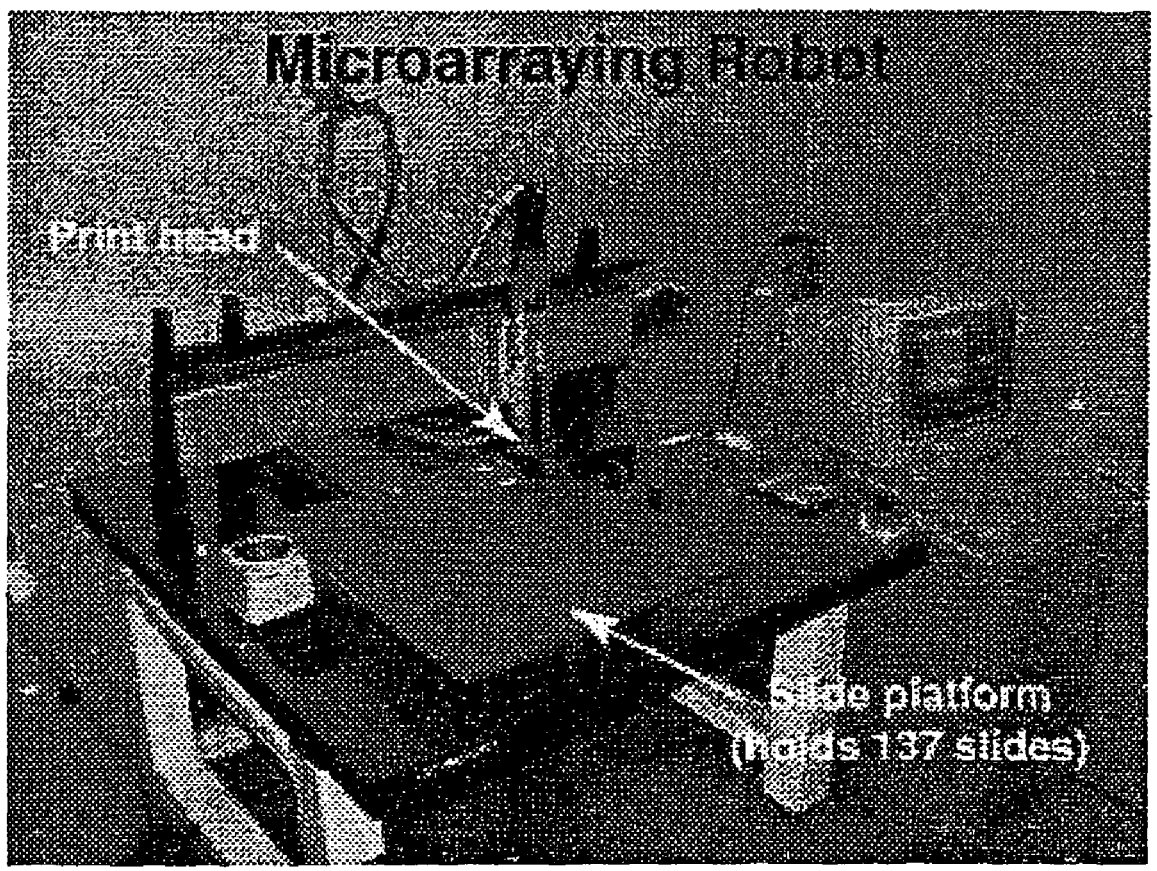
FIG. 16 shows the microarraying robot used to create the small molecule arrays.
Figure 17:
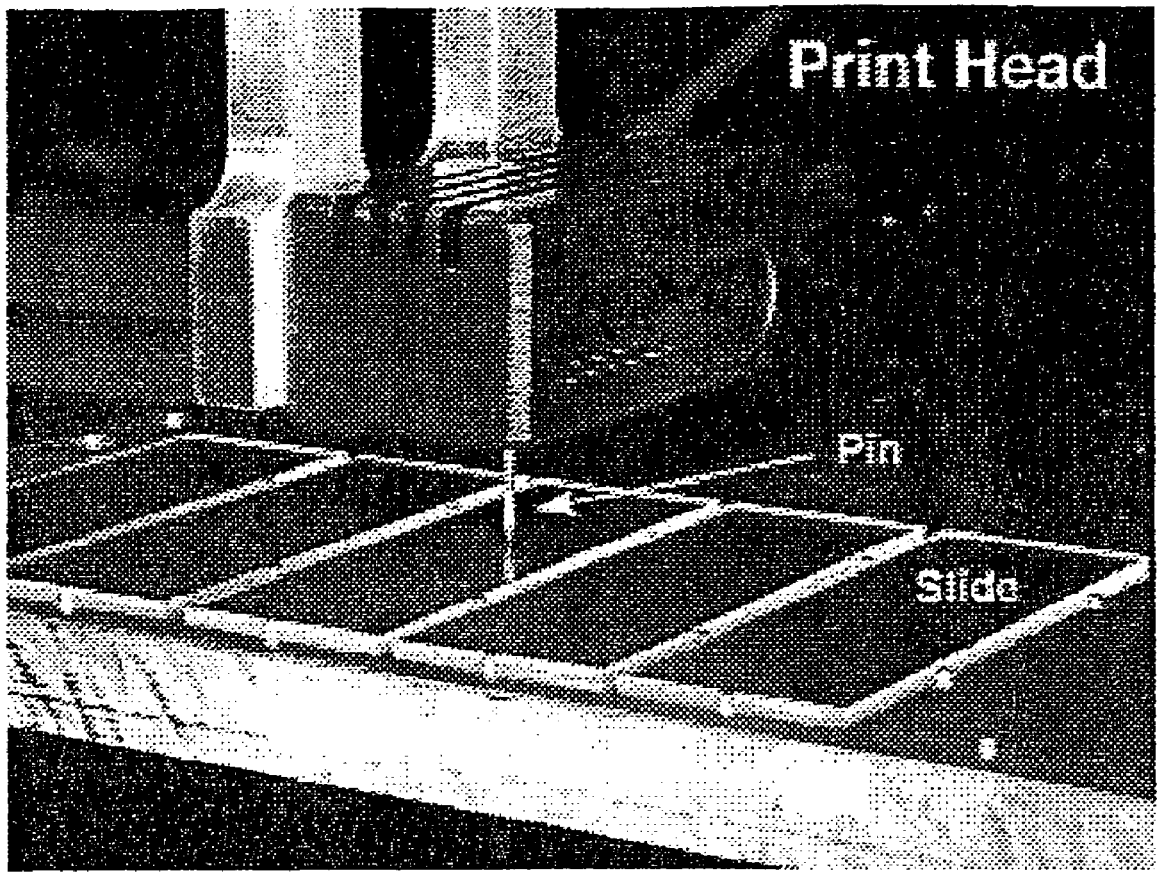
FIG. 17 shows the print head of the robot.
Figure 18:
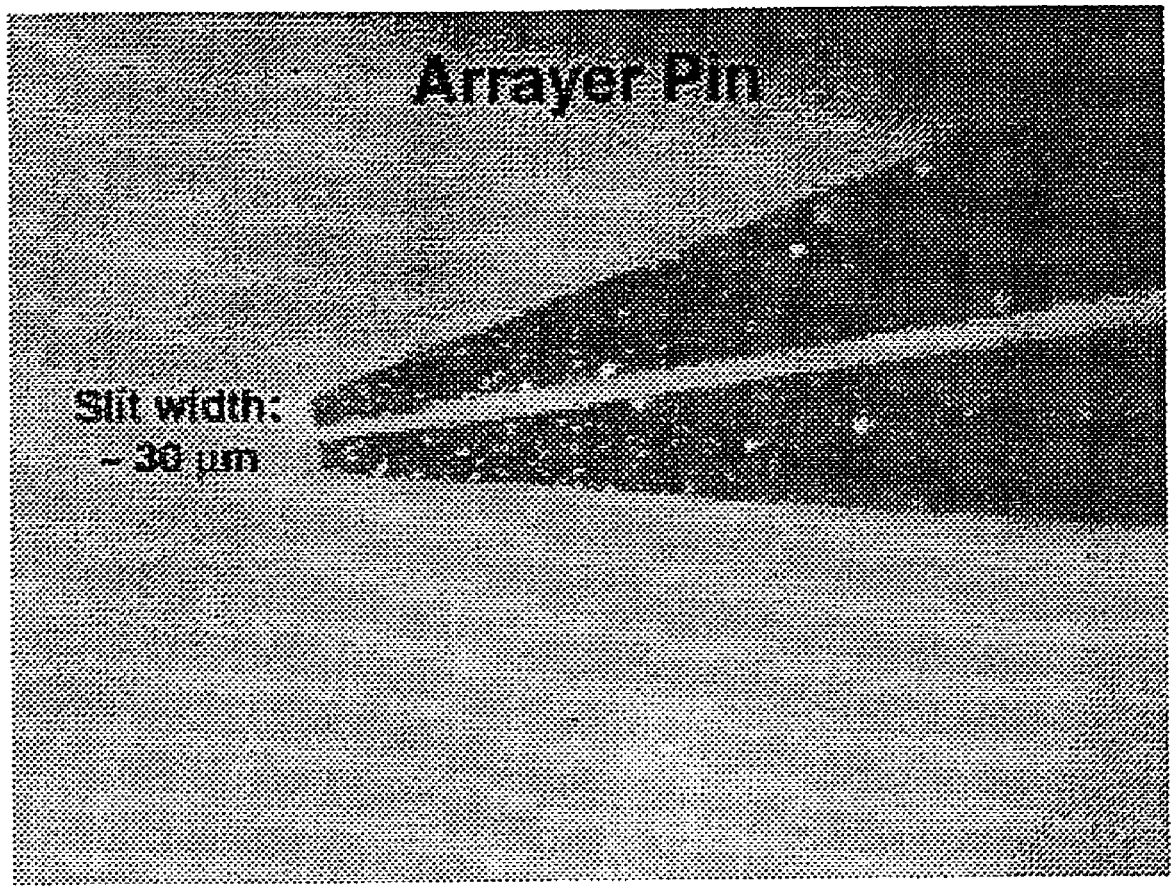
FIG. 18 shows the array pin of the robot.

Robotic Arraying of Small Molecules. Small molecules were printed using a microarraying robot (FIGS. 16, 17, and 18), constructed in this laboratory by Dr. James S. Hardwick and Jeffrey K. Tong according to directions provided by Dr. Patrick O. Brown (http://cmgm.stanford.edu/pbrown/mguide/index.html).

The robot was instructed to pick up a small amount of solution (~250 nL) from consecutive wells of a 96-well plate and repetitively deliver approximately 1 nL to defined locations on a series of maleimide-derivatized glass microscope slides. The pin used to deliver the compounds was washed with double distilled water for 8 s and dried under a stream of air for 8 s before loading each sample (6 s). Following printing, the slides were incubated at room temperature for 12 h and then immersed in a solution of 2-mercaptoethanol/DMF (1:99) to block remaining maleimide functionalities. The slides were subsequently washed for 1 h each with DMF, THF, and iPrOH, followed by a 1 h aqueous wash with MBST (50 mM MES, 100 mM NaCl, 0.1% Tween® 20, pH 6.0). Slides were rinsed with double-distilled water, dried by centrifugation, and either used immediately or stored at room temperature for several days without any observed deterioration.

Example 7

Detection of Protein-Small Molecule Interactions

Materials. Cy5-streptavidin, Cy5-goat-anti-mouse IgG, and, FITC-streptavidin were from Kirkegaard & Perry Laboratories (Gaithersburg, Md.). Mouse-anti-digoxin IgG (DI-22) was from Sigma-Aldrich Co. (St. Louis, Mo.). Mouse-anti-(His)$_6$ IgG (RGS•His antibody) was from Qiagen (Hilden, Germany).

Production of (His)$_6$-FKBP12. Construction of T5 Expression Plasmid. A 355-bp PCR product containing the coding sequence for human FKBP12 was obtained using primers FKBP-1S (ACGTACGT GGATCCATGGGAGTGCAGGTGGAAACCA) and FKBP-1N (ACGTACGT GTCGACTTATTCCAGTTTTAGAAGCTCCACATCGA) on template pJG-FKBP 12 (Licitra et al., *Proc. Natl. Acad. Sci. USA* 1996, 93, 12817-12821; incorporated herein by reference). The 333-bp Bam HI-Sal I fragment of this product was then ligated with the 3434-bp Bam HI-Sal I fragment of pQE-30 (Qiagen) to yield the T5 expression plasmid pQE-30-FKBP12 (3757 bp).

Production and Purification of (His)$_6$ FKBP 12. The host strain for protein production was M15[pREP4] (Qiagen). Cells from a single colony were grown in 500 mL of LB medium supplemented with 100 µg/mL sodium ampicillin and 25 µg/mL kanamycin at 37° C. up to an OD$_{600}$ of 0.8. The culture was cooled to room temperature and isopropyl 1-thio-β-D-galactopyranoside (IPTG) was added to a final concentration of 1 mM. After 16 h induction at room temperature, the cells were harvested and resuspended in 20 mL of PBS (10 mM phosphate, 160 mM NaCl, pH 7.5) supplemented with 100 µM phenylmethanesulfonyl fluoride (PMSF). Following cell lysis by passage through a French press, insoluble material was removed by centrifugation (28000 g, 20 min, 4° C.) and the supernatant loaded onto a column packed with 5 mL of Ni-NTA agarose (Qiagen) that had been preequilibrated with PBS. The column was thoroughly washed with PBS containing 10 mM imidazole, and bound protein was subsequently eluted with PBS containing 250 mM imidazole. The sample was dialyzed extensively against PBS and stored at 4° C.

Labeling of Proteins with Fluorophores. Cy3-labeled DI-22 was prepared from DI-22 mouse ascites fluid (Sigma-Aldrich Co.) using FluoroLink™ Cy3™ bisfunctional reactive dye (Amersham Pharmacia Biotech, Piscataway, N.J.) according to the recommended protocol. Similarly, Cy5-labeled (His)$_6$-FKBP12 was prepared from purified (His)$_6$-FKBP12 using FluoroLink™ Cy5™ monofunctional reactive dye (Amersham Pharmacia Biotech) according to the recommended protocol.

Probing Slides with Proteins. Reagents were applied to the printed face of the slides using PDMS slide reaction chambers. Rinsing and washing steps were performed with the slides face up in the lids of pipet tip boxes.

In each experiment, the slides were blocked for 1 h with MBST supplemented with 3% bovine serum albumin (BSA). Following each step in the procedure, the slides were rinsed briefly with MBST before applying the next solution. With the exception of the blocking step, the slides were exposed to protein solutions for 30 min at room temperature. These solutions were prepared by diluting stock solutions of the appropriate protein(s) with MBST supplemented with 1% BSA. After the final incubation, the slides were rinsed once with MBST and then gently agitated with 4 changes of MBST over the course of 12 min. The slides were dried by centrifugation and stored in the dark at room temperature.

The protein concentrations used in the preparation of FIGS. 7 and 8 were as follows:

FIG. 7A: •1 µg/mL Cy5-streptavidin
FIG. 7B: •2 µg/mL DI-22 (IgG1)
 •1 µg/mL Cy5-goat-anti-mouse IgG
FIG. 7C: •40 µg/mL (His)$_6$-FKBP12
 2 µg/mL mouse RGS-His IgG
 •1 µg/mL Cy5-goat-anti-mouse IgG
FIG. 8: •2 µg/mL FITC-streptavidin,
 +0.2 µg/mL Cy3-DI-22 (IgG1)
 +4 µg/mL Cy5-(His)$_6$-FKBP12

Scanning Slides for Fluorescence. Slides were scanned using an ArrayWoRx™ slide scanner (AppliedPrecision, Issaquah, Wash.). Slides were scanned at a resolution of 5 µm per pixel. Double filters were employed for both the incident and emitted light. For the images in FIG. 7, tetramethylrhodamine fluorescence was observed using a Cy3/Cy3 excitation/emission filter set (1 s exposure) and Cy5 fluorescence was observed using a Cy5/Cy5 excitation/emission filter set (2 s exposure). For the image in FIG. 8, fluorescein fluorescence was observed using a FITC/FITC excitation/emission filter set (10 s exposure), Cy3 fluorescence was observed using a Cy3/Cy3 excitation/emission filter set (2 s exposure), and Cy5 fluorescence was observed using a Cy5/Cy5 excitation/emission filter set (5 s exposure). The full slide image (top) was stitched with 4-fold pixel reduction and the magnified image (bottom) was stitched with 2-fold pixel reduction.

Example 8

Covalent Attachment and Screening of Alcohol-Containing Small Molecules on Glass Slides General procedures for synthetic transformations: Methylene chloride, diisopropylethylamine and dimethylformamide were distilled under nitrogen from calcium hydride. Tetrahydrofuran (HPLC grade, Fisher, solvent keg) was dried by passing the solvent through two columns of activated alumina (A-2) (Panghorn et al., *Organometallics* 1996, 15, 1518; incorporated herein by reference). All other reagents were obtained from commercial suppliers. Solution phase reactions were carried out in 2 dram vials with Teflon® screw caps. Reactions were monitored by thin layer chromatography using 0.25 mm silica gel 60 $F_{254}$ plates from EM Science and visualized with ceric ammonium molybdate (CAM) stain. All compounds were purified using 230-400 mesh silica gel 60 from EM Science. Biotinol was prepared as previously described (Islam et al., *J. Med. Chem.* 1994, 37, 293-304; incorporated herein by reference). The digoxigenin derivative as its N-hydroxysuccinimide ester was obtained from Molecular Probes Inc. The FKBP ligand (AP1497, an acid) was obtained from Dr. Kazunori Koide of Harvard University and from Ariad Pharmaceuticals (Keenan et al., *Bioorg. Med. Chem. Lett.* 1998, 6, 1309; incorporated herein by reference).

The solid support, 500-560 μm polystyrene 1% divinylbenzene (Rapp Polymere) was derivatized with a 3-(p-anisolyl-diisopropylsilyl)-propyl linker (Woolard et al., *J. Org. Chem.* 1997, 62, 6102; incorporated herein by reference). The library members were obtained from Dr. Kouji Hattori (Harvard). The secondary alcohol of this scaffold was derivatized following the method of Tan et al. (*J. Am. Chem. Soc.* 1999, 121, 9073-9087; incorporated herein by reference). Solid phase loading reactions were run under an inert atmosphere in 2.0 mL polypropylene Bio-Spin® chromatography columns (Bio-Rad Laboratories, Hercules, Calif.; 732-6008) bearing a 3-way nylon stopcock (Bio-Rad; 732-8107) and mixed by 360° rotation on a Barnstead-Thermolyne Labquake Shaker™ (VWR 56264-306).

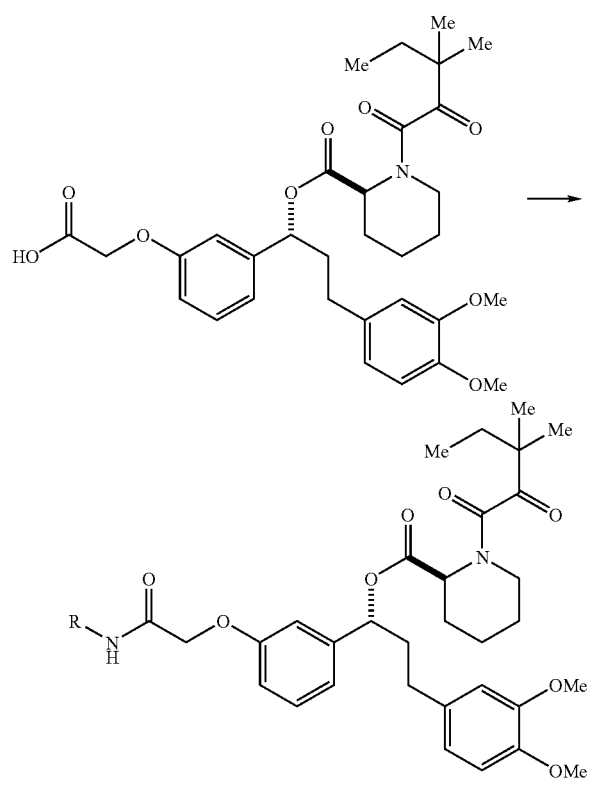

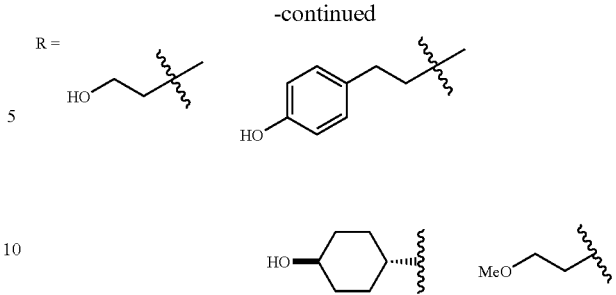

Representative procedure for the synthesis of the FKBP ligands. To the above mentioned acid (17 mg, 0.029 mmol), in a solution of DMF (0.30 mL) was added the respective amine or amine hydrochloride (0.038 mmol), PyBOP (24.4 mg, 0.047 mmol), and i-$Pr_2$NEt (0.015 mL, 0.088 mmol, amines; 0.020 mL, 0.12 mmol, amine hydrochlorides). The solution was stirred at ambient temperature for 15 h, dissolved in a dilute brine solution and was extracted with EtOAc (3 times). The organic layers were combined, washed with a 1/1 water/saturated brine solution, dried over $Na_2SO_4$, filtered, concentrated, and chromatographed on silica gel (0 to 10% in $CHCl_3$) to give a colorless film.

primary OH (1) (reaction with ethanolamine); $^1$H NMR (500 MHz, $CDCl_3$) δ 7.28 (m, 1H), 7.18 (m, 1H NH), 6.98-6.66 (m, 6H), 5.75 (dd, J=7.8, 5.4 Hz, 1H), 5.29 (d, J=4.9 Hz, 1H), 4.51 (m, 2H), 3.85 (s, 3H), 384 (s, 3H), 3.72 (m, 2H), 3.51 (m, 2H), 3.35 (b d, J=13.2 Hz 1 H), 3.16 (td, J=12.3, 2.7 Hz, 1H), 2.56 (m, 2H), 2.36 (b d, J=13.7 Hz, 1H), 2.23 (m, 1H), 2.05 (m, 1H), 1.77-1.62 (m, 6H), 1.48 (m, 1H), 1.34 (m, 1H), 1.21 (s, 3H), 1.19 (s. 3H), 0.87 (t, J=7.6 Hz, 3H); HRMS (TOF-ES$^+$) cal. for $C_{34}H_{47}N_2O_9$(M+H)$^+$, 627.3282, obs. 627.3306.

primary OMe (reaction with 2-methoxyethylamine); $^1$H NMR (500 MHz, $CDCl_3$) δ 7.30 (m, 1 H), 7.00-6.67 (m, 7H), 5.76 (m, 1H), 5.32 (d, J=4.9 Hz, 1H), 4.51 (m, 2H), 3.86 (s, 3H), 3.85 (s, 3H), 3.55 (m, 2H), 3.49 (m, 2H), 3.37 (d, J=13.0 Hz, 1H), 3.35 (s, 3H), 3.16 (td, J=13.2, 2.9 Hz, 1H), 2.57 (m, 2H), 2.36 (b d, J=13.7 Hz 1H), 2.24 (m, 1H), 2.06 (m, 1H), 1.79-1.58 (m, 6H), 1.51-1.30 (m, 2H), 1.23 (s, 3H), 1.21 (s, 3H), 0.89 (t, J=7.6 Hz, 3H); HRMS (TOF-ES$^+$) calc. for $C_{35}H_{48}N_2O_9Na$(M+Na)$^+$, 663.3258, obs. 663.3229.

secondary OH (reaction with trans-4-amino-cyclohexanol hydrochloride); $^1$H NMR (500 MHz, $CDCl_3$) δ7.29 (m, 1H), 6.99-666 (m, 6H), 6.41 (d, J=8.3 Hz, 1H, NH), 5.76 (M, 1H), 5.30 (d, J=5.4 Hz, 1H), 4.46 (m, 2H), 3.85 (s, 3H), 3.84 (s, 3H), 3.61 (m, 1H), 3.36 (b d, J=12.2 Hz, 1 H), 3.20 TD, J=13.2, 2.9 Hz, 1H), 2.56 (m, 2H), 2.36 (b d, J=13.7 Hz, 1H), 2.24 (m, 1H), 2.00 (m, 4H), 1.78-1.61 (m, 6H), 1.50-1.23 (m, 4H), 1.21 (s, 3H), 1.20 (s, 3H), 0.88 (t, J=7.3 Hz, 3H); HRMS (TOF-ES$^+$) calc. for $C_{38}H_{53}N_2O_9$(M+H)$^+$, 681.3751, obs. 681.3778.

phenolic OH (reaction with tyramine hydrochloride); $^1$H NMR (500 MHz, $CDCl_3$) δ7.31 (m, 1 H), 7.01-66 (m, 10H), 6.51 (m, 1H, NH), 5.81 (m, 1H), 5.33 (b d, J=5.1 Hz, 1H), 4.60 (m, 2 H), 3.86 (s, 6H), 3.55 (m, 2H), 3.40 (b d, J=13.0 Hz 1H), 3.27 (td, J=13.2, 2.9 Hz, 1H), 2.72 (t, J=6.4 Hz, 2H), 2.56 (m, 2H), 2.40 (b d, J=13.2 Hz, 1H), 2.24 (m, 1H), 2.06 (m, 1H), 1.87-1.64 (m, 6H), 1.54 (m, 1H), 1.40 (m, 1H), 1.24 (s, 3H), 1.21 (s, 3H), 0.88 (t, J=7.5 Hz, 3H); HRMS (TOF-ES$^+$) calc. for $C_{40}H_{50}N_2O_9Na$(M+Na)$^+$, 725.3414, obs. 725.3384.

Procedure for the digoxigenin derivative.

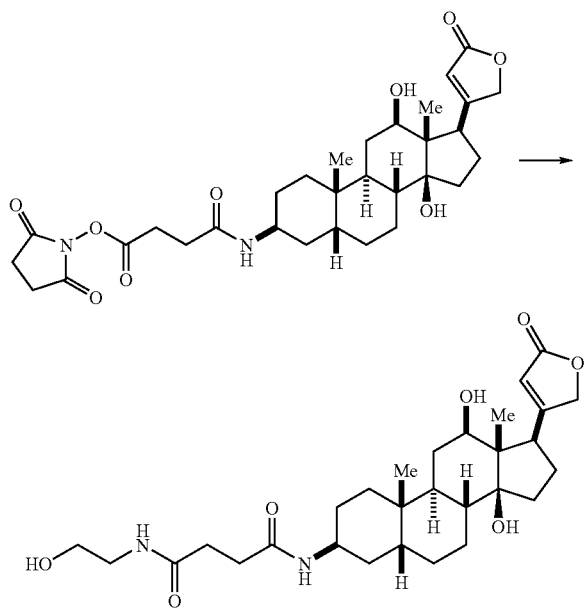

To a solution of the NHS ester of the digoxigenin derivative (5.0 mg, 0.0085 mmol) in DMF (0.3 mL) was added ethanolamine (0.0008 mL, 0.013 mmol) and 4-methylmorpholine (0.0011 mL, 0.010 mmol). The reaction was stirred at ambient temperature for three days, concentrated under high vacuum at room temperature, and chromatographed on silica gel (0 to 20% MeOH in CHCl$_3$); $^1$H NMR (400 MHz, 5/1 CDCl$_3$/CD$_3$OD) δ5.84 (s, 1H), 4.81 (AB d, 2H), 4.00 (b s, 1 H) 3.55 (m, 2H) 3.24 (m, 3H), 2.39 (m, 4H), 2.04 (m, 1H), 1.81 (m, 4H), 1.70-1.38 (m, 9H), 1.16 (m, 6H), 0.88 (s, 3H), 0.67 (s, 3H).

General procedure for loading alcohols via a silicon ether onto polystyrene beads.

After drying under vacuum for 8 h, the large polystyrene beads bearing a 3-(p-anisolyldiisopropylsilyl)-propyl linker (13.3 mg, 0.008 mmol, ca. 0.6 mmol silane/g resin) were added to a Bio-Rad tube, which was capped with a septum and a plastic stopcock and flushed with an inert gas. The tube was then charged via syringe with a 2.5% (v/v) solution of TMS-Cl in CH$_2$Cl$_2$ The beads were suspended for 15 min, and filtered with inert gas pressure. The beads were washed with CH$_2$Cl$_2$ (0.5 mL, 3 times, 2 min/rinse) and then suspended in a 3% (v/v) solution of triflic acid in CH$_2$Cl$_2$ (0.142 mL, 0.049 mmol) for 15 min during which time the tube was shaken periodically. The beads turn a dark brown color. The beads were suspended and rinsed with CH$_2$Cl$_2$ (0.5 mL, 3 times, 2 min/rinse) under an inert gas, and left suspended in the fourth volume of CH$_2$Cl$_2$ Freshly distilled 2,6-lutidene (0.007 mL, 0.064 mmol) was added (the brown color disappears) and the azeotropically dried (from benzene) alcohol (0.020 mmol) was added as a solution in CH$_2$Cl$_2$ via a canula transfer (for α-ketoamide and digoxigenin, 3 volumes, 0.3 mL/transfer) or introduced as a neat solid (e.g., biotinol, when the alcohol is not soluble in CH$_2$Cl$_2$). The tube was capped and tumbled at ambient temperature for 2-4 h. The beads were then filtered, suspended, and rinsed, for α-ketoamide, with CH$_2$Cl$_2$ (10 times, 5 min/rinse) and dried under high vacuum; for digoxigenin and biotin, the beads were rinsed likewise with DMF to remove non-covalently attached ligand.

Activation of slides for microarraying. Slides were activated for covalent attachment of alcohols as follows. Standard microscope slides (VWR) were immersed in 70/30 (v/v) H$_2$SO$_4$/30% H$_2$O$_2$ (piranha) for 16 h at ambient temperature. After removal from the piranha bath, the slides were washed extensively in ddH$_2$O, and then kept under water until use. To convert to the silyl chloride, the slides were first removed from the water and dried by centrifugation. At this point, the slides were immersed in a solution of THF containing 1% SOCl$_2$ and 0.1% DMF. The slides were incubated in this solution for 4 h at ambient temperature. The slides were then removed from the chlorination solution, washed briefly with THF, and placed on the microarrayer.

Release of alcohols from their solid supports. To liberate alcohols from the polystyrene beads, single beads were treated with 10 μL of 90/5/5 (v/v) THF/HF pyridine/pyridine at ambient temperature for 1 h. 10 μL of TMSOMe was then added, and allowed to stand at ambient temperature for an additional 0.5 h. The solvent was then removed in vacuo, and the liberated compound from a single bead was dissolved in 5 μL of DMF. These solutions were then robotically arrayed onto activated glass slides.

We confirmed the coupling of the α-ketoamide and biotin to the secondary alcohol of the library by LC/LRMS (TOF-ES$^+$) analysis of material released from a single bead of each type. The observed ions (M+H)$^+$ of 1064 and 725 matched the theoretical masses expected for C$_{59}$H$_{75}$N$_4$O$_{14}$ (α-ketoamide) and C$_{37}$H$_{50}$N$_5$O$_8$S (biotin), respectively.

Robotic printing. Compounds were arrayed onto glass slides using a DNA microarrayer constructed by Dr. James Hardwick and Jeff Tong following instructions on the web site of Professor Patrick Brown (Standard University; http://cmgm.stanford.edu/pbrown/mguide/index.html; incorporated herein by reference). The microarrayer typically picks up 250 nL from the 96-well plate and delivers 1 nL drops onto the slides. These spots were placed 400 μm apart on the slides.

Detection of protein/ligand interactions. After arraying, the slides were allowed to incubate at ambient temperature for 12 h. The slides were then washed for 2 h with DMF, and 1 h each with THF, isopropanol, and MBST (50 mM MES, 100 mM NaCl, 0.1% Tween-20, pH=6.0). The slides were then blocked for 1 h by incubation with MBST containing 3% BSA. After a brief rinse with MBST, the fluorescently labeled protein was then added at a concentration of 1 μg/mL in MBST supplemented with 1% BSA. The labeled proteins were created as described (Tan et al., *J. Am. Chem. Soc.* 1999, 121, 9073-9087; MacBeath et al., *J. Am. Chem. Soc.* 1999, 121, 7967-7968; each of which is incorporated herein by reference). The slide was incubated with the labeled protein for 0.5 h at ambient temperature. At this point, the slide was washed (10 times 1 mL with MBST, then briefly with H$_2$O) and dried by centrifugation. The slide was then scanned using an ArrayWoRx slide scanner (AppliedPrecision, Issaquah, Wash.) at a resolution of 5 μm per pixel. The following filter sets were employed: Cy5/Cy5 excitation/emission filter set (2 s exposure); Cy3/Cy3 excitation/emission filter set (1 s exposure); FITC/FITC excitation emission filter set (10 s exposure).

Example 9

Covalent Attachment Using Diazobenzylidene Chemistry

Diazobenzylidenes are known to react with heteroatoms that bear an acidic proton. Initial proton transfer from the heteroatom to the methine carbon of the diazobenzylidene is followed by nucleophilic displacement of $N_2$ of the heteroatom. To prepare glass slide derivatized with a diazobenzylidene moiety, the toluenesulfonylhydrazone derived from 4-carboxybenzaldehyde (1) was coupled to γ-aminopropylsilane slides as shown in FIG. 19. Subsequent base-induced elimination yields the putative diazobenzylidene-derived glass slides. Diazobenzylidene slides can be left at room temperature in the dark for at least three weeks with no noticeable deterioration in performance. They are typically stored at −20° C.

Figure 20:
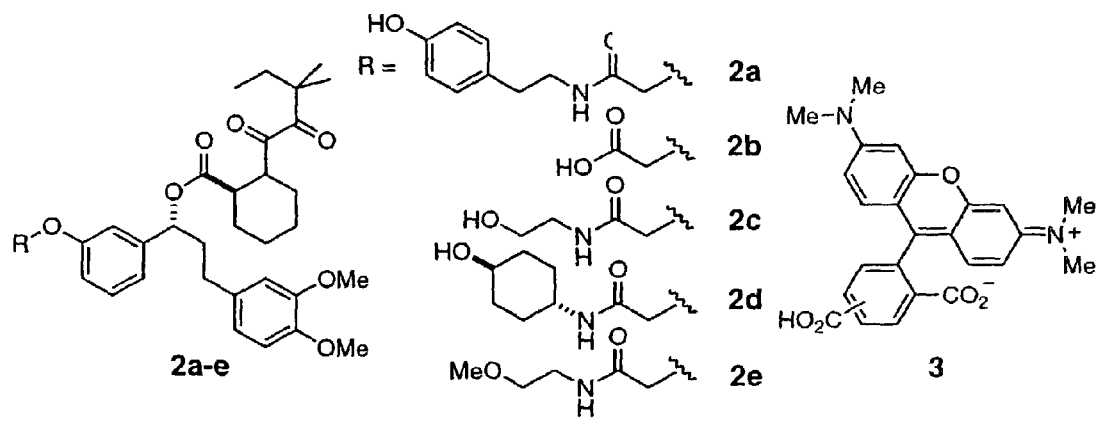
FIG. 20 shows α-ketoamide (2a-e) and tetramethylrhodamine (3) printed on diazobenzylidene derived slides. The DMF solutions of these compounds were spotted in duplicate in serial two-fold dilutions from 2 mM (lower right spot of each panel) to 1 μM (upper left corner of each panel).
Figure 20:
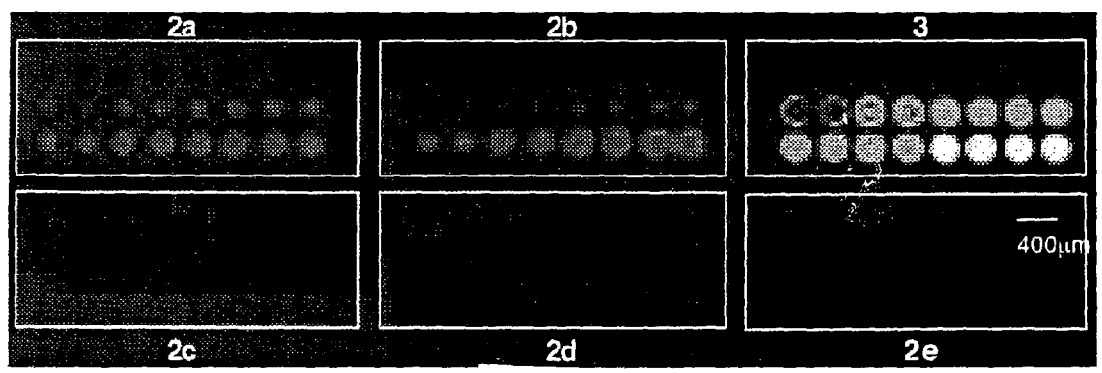

A robotic microarrayer was used to spot a range of concentrations (2 mM to 1 μM) of DMF solutions of tetramethylrhodamine (3) and the synthetic α-ketoamide derivatives (2a-e): phenol (2a), carboxylic acid (2b), primary alcohol (2c), secondary alcohol (2d), and methyl ester (2e). The slides were then quenched with glycolic acid, washed extensively with DMF, THF, methanol, and an aqueous buffer, and probed with Cy5-FKBP12 (1 μg/ml) (Harding et al. *Nature* 341:758-760, 1989; Siekierkea et al. *Nature* 341:755-757, 1989; each of which is incorporated herein by reference), a protein known to bind to derivatives of 2 (Holt et al. *J. Am. Chem. Soc.* 115:9925-9938, 1993; incorporated herein by reference). As expected, tetramethylrhodamine was immobilized, as were the phenol (2a) and carboxylic acid (2b), but not 2c, 2d, or 2e (FIG. 20). 2a and 3 were detectable when printed as low as 15 μM, whereas 2b was detectable when printed at as low as 31 μM.

Figure 21:
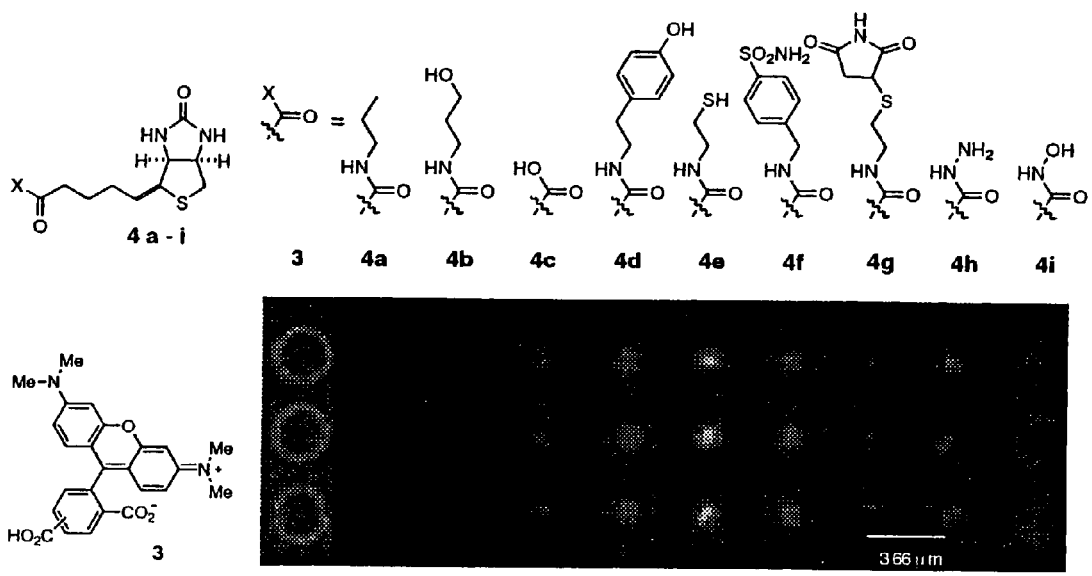
FIG. 21 shows tetramethylrhodamine (3) and biotin derivatives (4a-i) printed in triplicate at 100 μM and probed with 100 ng/mL Cy5-streptavidin.

To test the reactivity of these diazobenzylidene slides, 100 μM DMF solutions (compounds printed from aqueous solutions were capture as well) of biotin derivatives 4a-i were printed in triplicate, with tetramethylrhodamine printed for reference. This slide was probed with 100 nM Cy5-streptavidin, and as expected, compounds 4c-i immobilized, while 4a and 4b were not (FIG. 21). Thus, functional groups that bear a proton with a pKa <11 (pKa in DMSO <19) are covalently attached to these slides, while those that bear a proton with a pKa >16 (pKa in DMSO >28) are not.

Printed slides are typically stored at −20° C. with no noticeable deterioration over at least 2 months.

Experimentals

General. All commercially available materials were used without further purification unless otherwise noted. All solvents were dispensed from a solvent purification system wherein solvents are passed through packed columns (THF, $Et_2O$, $CH_3CN$, and $CH_2Cl_2$: dry neutral alumina; hexane, benzene, and toluene: dry neutral alumina and Q5 reactant; DMF: activated molecular sieves). All reactions were performed under dry $N_2$ unless otherwise indicated Solution phase reactions were monitored by analytical thin-layer chromatography performed using indicated solvent on E. Merck silica gel 60 $F_{254}$ plates (0.25 mm). Compounds were visualized by staining the plates with a cerium sulfate-ammonium molybdate solution followed by heating. Flash column chromatography was performed using the indicated solvent on E. Merck silica gel 60 (40-63 m). Yields refer to chromatographically and spectroscopically pure compounds except as otherwise noted. Infrared spectra were recorded on NaCl plates on a Nicolet 5PC FT-IR spectrometer with internal referencing. Absorption maxima ($v_{max}$) are reported in wavenumbers ($cm^{-1}$). NMR ($^1H$, $^{13}C$) spectra were recorded on Varian Mercury400 (400 MHz for $^1H$), and Varian Unity/Inova500 (500 MHz for $^1H$, $^{13}C$) spectrometers. Chemical shifts ($\delta_H$) are quoted in ppm and referenced to $CDCl_3$ ($^1H$-NMR, 7.26; $^{13}C$-NMR, 77.0, center line) unless otherwise noted. Low resolution mass spectra were obtained with JEOL AX-505H, SX-102A (CI/ELI), Micromass Platform II and LCT (APCI/ES/LCMS) spectrometers. Only molecular ions, fractions from molecular ions and other major peaks are reported. High resolution mass spectra was obtained with Micromass LCT (ES) spectrometer, and reported mass values are within the error limits of ±5 ppm mass unit.

Experimental Procedures:

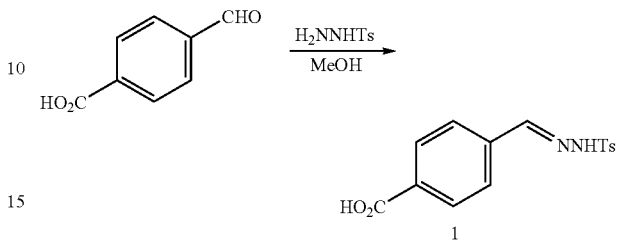

1:4-carboxybenzaldehyde (50.5 g, 336 mmol) and toluenesulfonylhydrazide (62.5 g, 336 mmol) were heated in methanol (1.5 L) at 70° C. The resulting solution was stirred at 23° C. for 16 h, brought to 60° C. and, after addition of water (0.75 L), was slowly cooled to 23° C. The white precipitate (69.7 g) was collected by filtration. Water (2 L) was added to the filtrate, and the resulting precipitate (31.9 g) was collected by filtration to afford 1 (101.6 g, 95%): $^1H$ NMR (400 MHz, $CD_3OD$) δ 7.97 (d, J=8.4 Hz, 2H), 7.85 (s, 1H), 7.82 (d, J=8.0 Hz, 2H), 7.64 (d, J=8.4 Hz, 2H), 7.35 (d, J=8.0 Hz, 2H), 2.37 (s, 3H); $^{13}C$ NMR (100 MHz, $CD_3OD$) δ 169.2, 147.1, 145.5, 139.5, 137.3, 133.0, 131.0, 130.7, 128.7, 127.9, 21.5; FT-IR (thin film) 3216 (br), 1699, 1686, 1673, 1664, 1654, 1555, 1509, 1412, 1366, 1346, 1320, 1289, 1228, 1157, 1121, 1049, 1013, 942, 840, 768, 697 $cm^{-1}$; LRMS (TOF ES) calcd for $C_{15}H_{15}N_2O_4$, 319 m/z $(M+H)^+$; observed 319.

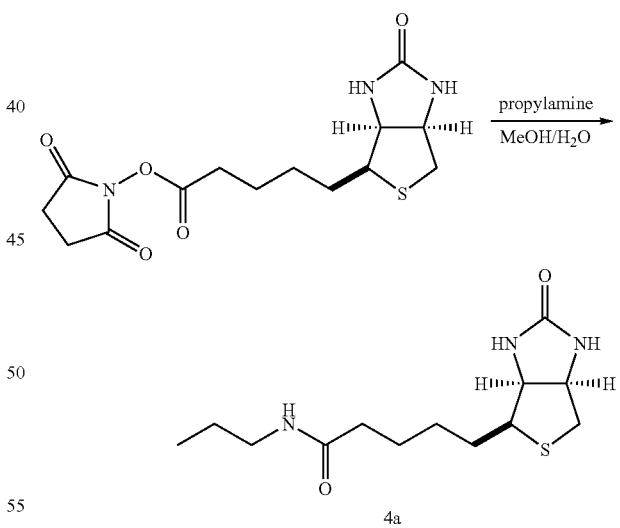

4a: To N-hydroxysuccinimidobiotin (6.2 mg, 18.2 μmol) was added 1-propylamine (100 μL, 1.22 mmol), methanol (200 μL) and water (100 μL). The resulting solution was stirred for 1 h at 23° C., concentrated under a stream of nitrogen, redissolved in 500 μL methanol, and purified by reverse-phase HPLC (dp 5μ, 10 mm×25 cm, 2 mL/min, 0 to 100% acetonitrile/water over 15 min, retention time: 14 min) to afford 4c (4.8 mg, 92%): $^1H$ NMR (400 MHz, $CD_3OD$) δ 4.49 (dd, J=7.6, 5.2 Hz, 1H), 4.30 (dd, J=8.0, 4.4 Hz, 1H), 3.20 (m, 1H), 3.12 (t, J=7.2 Hz, 2H), 2.92 (dd, J=12.8, 5.2 Hz, 1H), 2.70 (d, J=12.8 Hz, 1H), 2.19 (t, J=7.6 Hz, 2H), 1.72 (m, 2H), 1.62 (m, 4H), 1.50 (m, 2H), 1.44 (m, 2H); $^{13}$C NMR (125 MHz, CD$_3$OD) δ 176.0, 166.1, 63.4, 61.6, 57.0, 42.1, 41.0, 36.8, 29.8, 29.5, 26.9, 23.6, 11.7; FT-IR (thin film) 3294, 3976, 2935, 2867, 1701, 1642, 1551, 1465, 1424, 1323, 1264, 1155, 922 cm; HRMS (TOF ES) calcd for C$_{13}$H$_{24}$N$_3$O$_2$S 286.1589 m/z (M+H)$^+$; observed 286.1584 (1.7 ppm error).

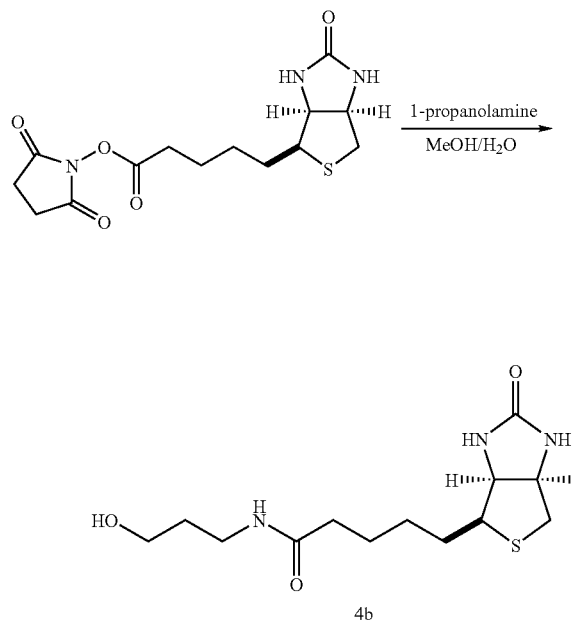

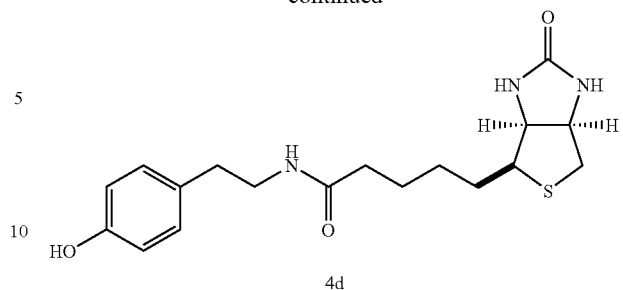

4d

4d: To N-hydroxysuccinimidobiotin (13.3 mg, 39.0 μmol) was added a solution of tyramine (5.9 mg, 43 μmol in 191 μL) in 3:1 methanol:water. Methanol (100 μL) was added, and the resulting solution was stirred at 23° C. for 16 h and purified by reverse-phase HPLC (dp 5μ, 10 mm×25 cm, 2 mL/min, 0 to 100% acetonitrile/water over 25 min, retention time: 16 min) to afford 4d (11.5 mg, 81%): $^1$H NMR (400 MHz, CD$_3$OD) δ 7.02 (d, J=8.8 Hz, 2H), 6.70 (d, J=8.4 Hz, 2H), 4.49 (dd, J=7.2, 4.8 Hz, 1H), 4.28 (dd, J=7.6, 4.4 Hz, 1H), 3.36 (m, 2H), 3.16 (m, 1H), 2.93 (dd, J=12.8, 5.2 Hz, 1H), 2.69 (m, 3H), 2.15 (t, J=7.6 Hz, 2H), 1.68 (m, 2H), 1.59 (m, 2H), 1.36 (m, 2H); $^{13}$C NMR (125 MHz, CD3OD) 176.0, 166.1, 156.8, 131.3, 130.8, 116.2, 63.3, 61.6, 56.9, 42.1, 41.0, 36.8, 35.6, 29.6, 29.4, 26.9; FT-IR (thin film) 3249, 2926, 2857, 1692, 1679, 1639, 1631, 1610, 1564, 1548, 1532, 1515, 1461, 1451, 1432, 1330, 1265, 1242, 1171, 1104, 925, 832 cm$^{-1}$; HRMS (TOF ES) calcd for C$_{18}$H$_{26}$N$_3$O$_3$S 364.1695 m/z (M+H)$^+$; observed 364.1693 (0.5 ppm error).

4b: To a suspension of N-hydroxysuccinimidobiotin (6.2 mg, 18.2, μmol) in 500 μL methanol was added 1-propanolamine (1.39 μL, 20.0 μmol). After stirring at 37° C. for 24 h, the resulting solution was purified by reverse-phase HPLC (dp 5μ, 10 mm×25 cm, 2 mL/min, 0 to 75% acetonitrile/water over 15 min, retention time: 12.1 min) to afford 4c (4.8 mg, 88%): $^1$H NMR (500 MHz, CD$_3$OD) δ 4.49 (dd, J=8.0, 5.0 Hz, 1H), 4.30 (dd J=8.0, 5.0 Hz, 1H), 3.57 (t, J=6.5 Hz, 2H), 3.35 (t, J=7.0 Hz, 2H), 3.31 (m, 1H), 3.02 (dd, J=13.0, 5.0 Hz, 1H), 2.79 (d, J=12.5 Hz, 1H), 2.30 (t, J=7.5 Hz, 2H), 1.70 (m, 4H), 1.63 (m, 2H) 1.43 (m, 2H); $^{13}$C NMR (125 MHz, CD$_3$OD) δ 176.3, 63.4, 61.6, 60.4, 57.0, 41.0, 37.4, 36.8, 33.2, 29.8, 29.5, 26.9; FT-IR (thin film) 3287, 3083, 2920, 2863, 1701, 1685, 1632, 1620, 1543, 1509, 1478, 1458, 1323, 1265, 1240, 1205, 1142, 1073, 1051 cm$^{-1}$; HRMS (TOF ES) calcd for C$_{13}$H$_{24}$N$_3$O$_3$S 302.1538 m/z (M+H)$^+$; observed 302.1528 (3.3 ppm error).

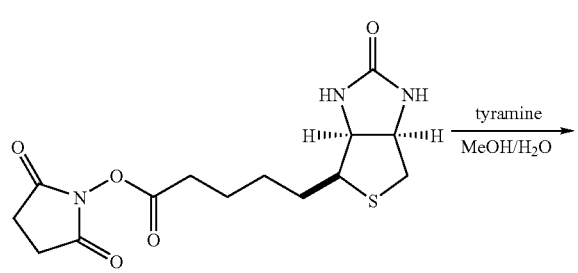

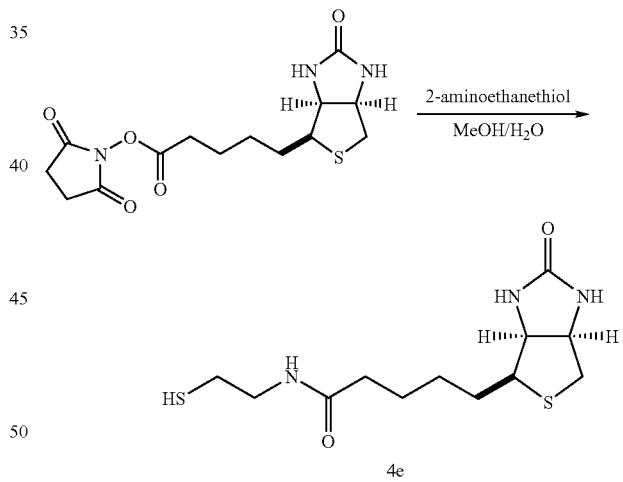

4e

4e: To 2-aminoethanethiol hydrochloride (13.7 mg, 0.121 mmol) was added 120.6 μL of 1N NaOH (0.121 mmol). 62.5 μL (62.5 μmol) of the resulting solution was added to N-hydroxysuccinimidobiotin (19.4 mg, 56.8 μmol), and 2:1 methanol:water was added to a total volume of 3 mL. After stirring 12 h at 37° C., the volume was reduced to 1 mL under nitrogen and the reaction mixture was purified by reverse-phase HPLC (dp 5μ, 10 mm×25 cm, 2 mL/min, 0 to 60% acetonitrile/water over 30 min, retention time: 15 min) to afford 4e (13.3 mg, 77%): $^1$H NMR (500 MHz, CD$_3$OD) δ 4.49 (dd, J=8.5, 5.5 Hz, 1H), 4.30 (dd, J=7.5, 4.5 Hz, 1H), 3.48 (t, J=7.0 Hz, 2H), 3.20 (m, 1H), 2.94 (dd, J=13.0, 5.0 Hz, 1H), 2.83 (t, J=6.5 Hz, 2H), 2.69 (d, J=12.5 Hz, 1H), 2.22 (t, J=7.5 Hz, 2H), 1.71 (m, 2H), 1.60 (m, 2H), 1.44 (m, 2H); 13C NMR (125 MHz, CD₃SOCD₃) δ172.1, 162.8, 61.1, 59.2, 55.5, 42.1, 41.9, 35.1, 28.2, 28.1, 25.3, 23.5; FT-IR (thin film) 3288, 3077, 2921, 2858, 1698, 1643, 1547, 1461, 1425, 1324, 1266, 1204, 1025, 1025 cm$^{-1}$; HRMS (TOF ES) calcd for C$_{12}$H$_{22}$N$_3$O$_2$S$_2$ 304.1153 m/z (M+H)$^+$; observed 304.1148 (1.6 ppm error).

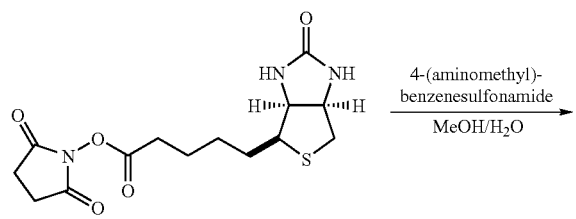

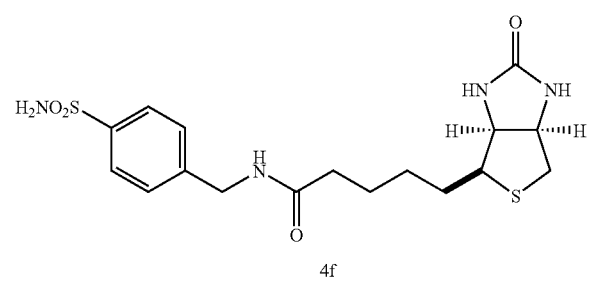

4f: To 4-(aminomethyl)-benzenesulfonamide hydrochloride (31.8 mg, 0.143 mmol) was added 143 µL of 1N NaOH and 143 µL of methanol. 199 µL (99.3 µmol) of the resulting solution was added to N-hydroxysuccinimidobiotin (22.6 mg, 66.2 µmol), and 2:1 methanol:water was added to a total volume of 3 mL. The solution was concentrated under a stream of nitrogen, redissolved in 1 mL 2:1 methanol:water, and purified by reverse-phase HPLC (dp 5µ, 10 mm×25 cm, 2 mL/min, 20 to 30% acetonitrile/water over 30 min, retention time: 11.5 min) to afford 4f (23.5 mg, 86%): (d, J=8 Hz, 2H), 6.34 (s, br, 1H), 6.27 (s, br, 1H), 4.37 (dd, J=7.5, 5.5 Hz, 1H), 4.72 (s, 2H), 4.16 (dd, J=7.5, 4.5 Hz, 1H), 3.06 (m, 1H), 2.83 (br s, 1H), 2.78 (dd, J=13.0, 5.5 Hz, 2H), 2.67 (br s, 1H), 2.57 (d, J=13.5 Hz, 1H), 2.14 (t, J=6.5 Hz, 2H), 1.56-1.47 (m, 4H), 1.38 (m, 2H); $^{13}$C NMR (125 MHz, CD₃SOCD₃) δ 172.2, 162.7, 143.9, 142.5, 127.5, 125.7, 61.0, 59.1, 55.5, 55.4, 41.5, 35.1, 28.3, 28.1, 25.3; FT-IR (thin film) 3284, 3095, 2925, 2859, 1685, 1647, 1558, 1538, 1458, 1326, 1264, 1160, 1099, 1027 cm$^{-1}$; HRMS (TOF ES) calcd for C$_{17}$H$_{25}$N$_3$O$_2$S$_2$ 413.1317 m/z (M+H)$^+$; observed 413.1324 (1.7 ppm error).

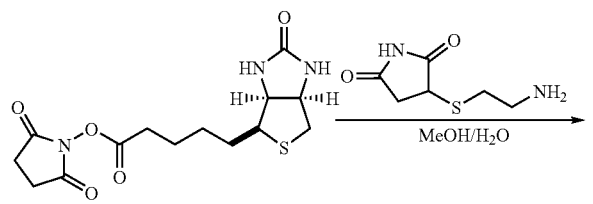

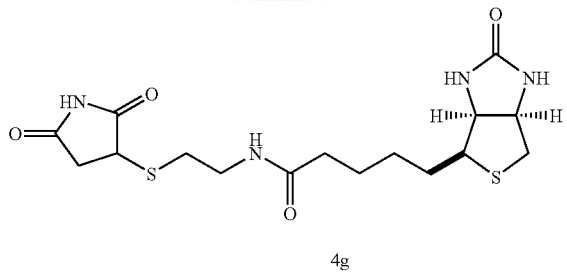

4g: Maleimide (45.5 mg, 0.469 mmol) and 2-aminoethanthiol (55.0 mg, 0.484 mmol) were brought to a total volume of 150 µL in water and stirred for 12 h at 37° C. 37.4 µL (0.117 mmol) of the resulting solution was combined with 1N NaOH (93.5 µL, 93.5 µmol), added to N-hydroxysuccinimidobiotin (26.6 mg, 77.9 µmol), brought to a total volume of 3 mL in 2:1 methanol:water, and stirred for 27 h at 37° C. The solution was concentrated under a stream of nitrogen, redissolved in 1 mL 2:1 methanol:water, and purified by reverse-phase HPLC (dp 5µ, 10 mm×25 cm, 2 µL/min, 0 to 60% acetonitrile/water over 25 min, retention time: 16.8 min) to afford 4 g (13.1 mg, 42%): $^1$H NMR (400 MHz, CD₃OD) δ4.49 (dd, J=8.0, 5.2 Hz, 1H), 4.30 (dd, J=10.0, 5.5 Hz, 1H), 3.94 (dd, J=9.2, 4.0 Hz, 1H), 3.47 (m, 1H), 3.42 (m, 1H), 3.21 (m, 1H), 3.19 (m, 1H), 3.02 (m, 1H), 2.92 (dd, J=12.8, 5.2 Hz, 1H), 2.82 (m, 1H), 2.70 (d, J=12.8, 1H), 2.74 (d, J=18.4 Hz, 1H), 2.22 (t, J=7.6 Hz, 2H), 1.75-1.55 (m, 4H), 1.45 (m, 2H); $^{13}$C NMR (100 MHz, CD₃OD) δ180.3, 178.5, 176.3, 166.1, 63.3, 61.6, 57.0, 41.8, 41.0, 39.5, 38.4, 36.7, 32.3, 29.7, 29.4, 26.8; FT-IR (thin film) 3285, 2976, 2853, 2744, 2475, 1779, 1710, 1690, 1678, 1666, 1658, 1631, 1465, 1451, 1432, 1415, 1346, 1265, 1232, 1196 cm$^{-1}$; HRMS (TOF ES) calcd for C$_{16}$H$_{25}$N$_4$O$_4$S$_2$ 401.1317 m/z (M+H)$^+$; observed 401.1309 (2.0 ppm error).

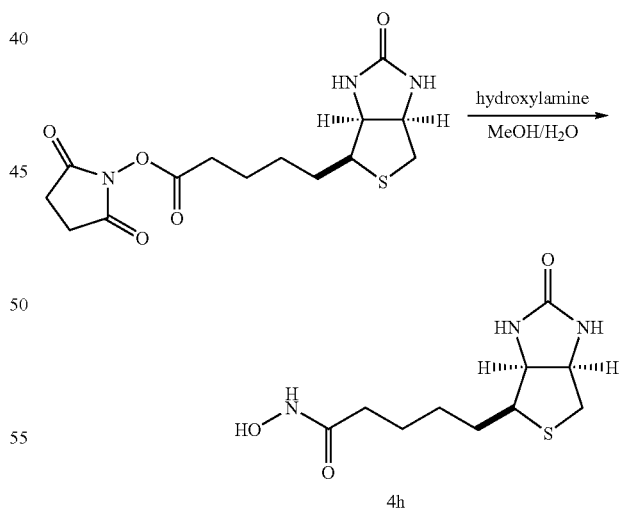

4h: To N-hydroxysuccinimidobiotin (6.6 mg, 19.3 µmol) was added hydroxylamine (50 µL of 50 wt % in water, 0.757 mmol) and methanol (50 µL). The resulting solution was stirred for 1 h at 23° C., concentrated to dryness under a stream of nitrogen and redissolved in 200 µL of 1:1 methanol: water. The reaction mixture was purified by reverse-phase HPLC (dp 5µ, 10 mm×25 cm, 2 mL/min, 0 to 60% acetonitrile/water over 30 min, retention time: 11.5 min) to afford 4h (4.5 mg, 90%): $^1$H NMR (500 MHz, CD$_3$SOCD$_3$) δ 7.78 (s, br, 1H), 6.34 (s, br, 1H), 6.27 (s, br, 1H), 4.82 (s, br, 1H), 4.37 (dd, J=8.0, 5.0 Hz, 1H), 4.19 (dd, J=7.5, 4.0 Hz, 1H), 3.10 (m, 1H), 2.78 (dd, J=13.0, 5.0 Hz, 1H), 2.57 (d, J=15 Hz, 1H), 1.96 (d, J=7.5 Hz, 2H), 1.55 (m, 2H), 1.46 (m, 2H), 1.39 (m, 2H); $^{13}$C NMR (125 MHz, CD$_3$OD) δ 173.2, 165.7, 63.0, 61.1, 56.7, 41.1, 33.4, 29.3, 29.1, 26.2; FT-IR (thin film) 3214, 2918, 2852, 1688, 1643, 1611, 1321, 976, 829 cm$^{-1}$; HRMS (TOF ES) calcd for C$_{10}$H$_{18}$N$_3$O$_3$S 260.1069 m/z (M+H)$^+$; observed 260.1077 (3.1 ppm error).

Slide Preparation for Small Molecule Microarraying. Diazobenzylidene slides were prepared as follows. CMT-GAPS™ Coated slides (Gamma Amino Propyl Silane coated slide, Corning®) were immersed in a solution of 1 (10 mM), PyBOP (10 mM) and iPr$_2$NEt (10 mM) in anhydrous DMF for 2-16 hours (2 h is sufficient, 16 h is typical). The slides are then washed extensively with DMF and methanol. To convert the tosylhydrazone-derived slides to the diazobenzylidene-derived slides, the slides are immersed in a solution of 100 mM sodium methoxide in ethylene glycol, and heated at 90° C. for 2 hours. The slides are then washed extensively with methanol. Slides can be stored at this point for at least 3 weeks in the dark at room temperature with no noticeable deterioration in performance, but are typically stored at −20° C.

Robotic Small Molecule Printing. Compounds were arrayed onto diazobenzylidene-derived glass slides using an Omni-Grid™ 2000 microarrayer (GeneMachines, San Carlos, Calif.). The OmniGrid™ microarrayer was loaded with 48 ArrayIt™ stealth micro spotting pins (catalog# SMP4, TeleChem International, Inc., Sunnyvale, Calif.). These pins each typically pick up 250 nL of the DMF stock solution from the 384 microtiter well plate. To ensure uniform spot diameters, the arrayer was instructed to place ca. 20 spots onto a blot slide before arraying onto the diazobenzylidene-derived slides. The arrayer then delivered 1 nL drops placed 375 μm apart: onto the slides. For the printing of the DOS-derived phenol-containing fused bicyclic and tetracyclic compounds, 18×384 microtiter well plates were used. The last two rows of each plate do not contain compounds and were control wells for use in cell-based phenotypic assays. Therefore, a total of 6912 features, 6336 of which contain DOS-derived phenols, were printed onto each slide, and a total of 80 diazobenzylidene slides were typically printed at a time. After compounds were printed onto the slides, the slides were typically left on the platform for 12-16 h, but could also be removed from the platform and stored in the dark at room temperature. Subsequently, the slides were immersed in a 1M aqueous glycolic acid1 solution for 30 min to quench remaining diazobenzylidene moieties. The slides were then subjected to 30 min washes with DMF, THF, methanol, and PBST (50 mM phosphate, 150 mM NaCl, 0.1% Tween-20, pH 7.4). The slides are either rinsed with ddH$_2$O and dried by centrifugation, or rinsed with ddH$_2$O, then methanol, and dried under a stream of nitrogen, and stored at −20° C. prior to screening. In the case of printing tetramethylrhodamine and compounds 4a-h (FIG. 3), compounds were arrayed using a DNA microarrayer constructed by Dr. James Hardwick and Dr. Jeff Tong following the instructions on the web site of Professor Patrick Brown (Stanford University). The distance between spot-centers was set at 366 μm.1 Compounds 2a-e and tetramethylrhodamine (FIG. 20) were arrayed.

Example 10

Figure 22:
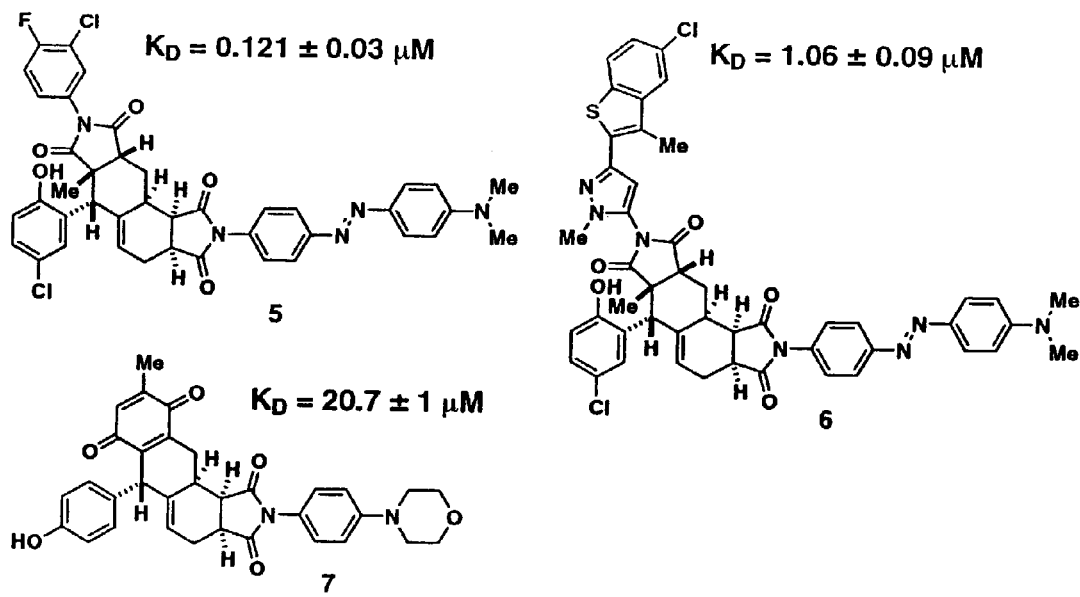
FIG. 22 shows the structures of calmodulin binders and their respective $K_D$s as determined by surface plasmon resonance spectroscopy.

Discovery of Novel Calmodulin Ligands from Microarrays of Diversity-Oriented Synthesis-Derived Phenols To demonstrate the ability of this covalent slide-capture method to identify new binding interactions between a protein and diversity-oriented synthesis-derived small molecules, 6336 phenol-containing fused bicycles and tetracycles (Kwon et al. J. Am. Chem. Soc. accepted; incorporated herein by reference), prepared in an encoded (Blackwell et al. Angew. Chem. Int. Ed. Engl. 40:3421-3425, 2001; incorporated herein by reference), one-bead-one-stock solution (12) format, were printed and probed with Cy5-calmodulin. Cy5 detection was chosen to avoid conflict with compound autofluorescence in the Cy3 channel. Positive hits from the microarray were retested for their ability to bind to the immobilized protein using surface plasmon resonance (SPR) spectroscopy (BIAcore). This process enables a rapid initial prioritization of positives prior to resynthesis, The initial secondary SPR screening was performed using compound (2 μL of a 1 mM DMF stock) directly from the original stock solutions used for microarray production. Of the 16 compounds on the microarray deemed positives, 13 showed qualitative binding to immobilized calmodulin based on the initial surface plasmon resonance spectroscopic analysis. Negative controls showed no effect. For this set, compound 5, 6, and 7 were resynthesized, purified, and their K$_D$s with calmodulin determined by SPR using steady state affinity analysis. 5 has a K$_D$ of 0.121±0.03 μM, 6 had a K$_D$ of 1.06±0.09 μM, and 7 had a K$_D$ of 20.7±1 μM (FIG. 22).

Non-biased (i.e., not designed to interact with a given protein or class of proteins using structural motifs known to favor such binding) phenol-containing fused bicycles and tetracycles were immobilized as microarrays on diazobenzylidene slides. When they were probed with a protein, the observed positives corresponded well to binding interactions observed by SPR, where the protein is immobilized and the compound is free in solution.

Experimentals

Preparation of Tetracycles (5-7) and α-Ketoamide Derivatives (2a-e). Tetracyclic compounds were synthesized based on the previously reported method in the library synthesis paper (O. Kwon, S. B. Park, S. L. Schreiber, J. Am. Chem. Soc. 2002, 124 13402-13405). α-ketoamide derivatives 2a-e were synthesized as previously reported (ref 2b).

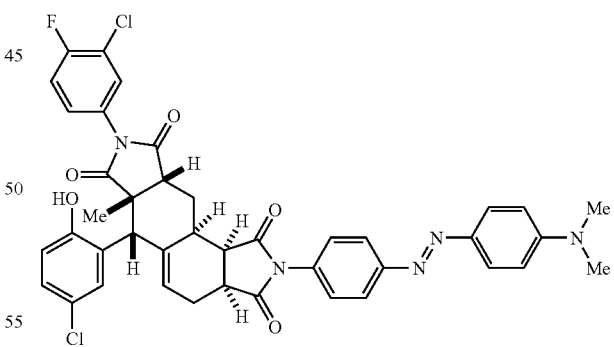

5

Tetracycle 5: $^1$H NMR (500 MHz, CDCl$_3$) δ 7.85 (d, J=8.5 Hz, 2H), 7.84 (d, J=8.5 Hz, 2H), 7.48 (m, 1H), 7.33 (dd, J=7.0, 2.5 Hz, 1H) 7.13 (m, 1H), 7.12 (dd, J=9.0, 2.5 Hz, 1H), 6.96 (br s, 1H), 6.74 (d, J=9.5 Hz, 2H), 6.71 (d, J=8.5 Hz, 2H), 5.57, (m, 1H), 5.28 (s, 1H), 3.47 (s, 1H), 3.33 (m, 2H), 3.21-3.18 (m, 2H), 3.09 (s, 6H), 2.84 (dd, J=15.0, 7.0 Hz, 1H), 2.61-2.52 (m, 2H), 1.41 (s, 3H); $^{13}$C NMR (125 MHz, CDCl$_3$) δ 180.9, 180.9, 178.9, 154.5, 154.4, 152.7, 145.6, 143.5, 141.1, 135.8, 132.7, 128.8, 128.2, 127.0, 125.5, 125.3, 122.8, 122.6, 117.0, 111.5, 49.4, 46.5, 43.3, 40.3, 40.1, 34.2, 30.3, 29.7, 20.5, 14.1; FT-IR (thin film) 3446, 3332, 2953, 2925, 2849, 1709, 1596, 1562, 1501, 1444, 1425, 1378, 1368, 1269, 1155, 1136, 1070, 1046, 1027 cm$^{-1}$; HRMS (TOF ES) calcd for $C_{41}H_{35}Cl_2FN_5O_5$, 766.1999 m/z (M+H)$^+$; observed 766.1995 (0.5 ppm error).

6

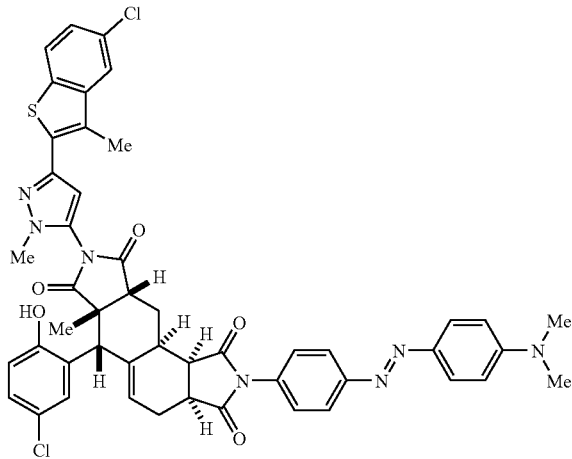

Tetracycle 6: $^1$H NMR (500 MHz, CDCl$_3$) δ 7.85 (d, J=8.5 Hz, 2H), 7.84 (d, J=8.5 Hz, 2H), 7.69 (d, H, J=8.5 Hz, 1H), 7.66 (d, J=1.5 Hz, 1H), 7.27 (dd, J=8.5, 2.0 Hz, 1H), 7.20 (d, J=9.0 Hz, 2H), 7.11 (dd, J=8.5, 2.5 Hz, 1H), 6.95 (br s, 1H), 6.73 (d, J=9.0 Hz, 2H), 6.73 (d, J=7.5 Hz, 1H), 6.52 (s, 1H), 5.63 (br s, 1H), 4.99 (s, 1H), 4.20 (s, 1H), 3.70 (s, 3H), 3.44 (s, 1H), 3.33 (m, 2H), 3.20 (m, 2H), 3.08 (s, 3H), 2.89 (m, 1H), 2.63 (m, 2H), 2.53 (s, 3H), 2.12 (m, 1H), 1.41 (d, J=6.0 Hz, 3H); $^{13}$C NMR (125 MHz, CD$_3$COCD$_3$) δ 179.0, 178.7, 155.4, 153.9, 153.1, 149.2, 144.1, 143.5, 142.9, 134.3, 133.4, 131.0, 129.6, 128.8, 128.5, 126.0, 125.8, 125.6, 124.5, 123.4, 122.9, 122.4, 117.1, 112.4, 104.5, 50.8, 49.0, 44.3, 40.3, 36.7, 26.0, 23.4, 12.9; FT-IR (thin film) 3446, 3171, 2955, 2915, 2849, 1724, 1709, 1693, 1600, 1444, 1425, 1378, 1366, 1273, 1136, 1074, 942, 819 cm$^{-1}$; HRMS (TOF ES) calcd for $C_{48}H_{42}Cl_2N_7O_5S$, 898.2345 m/z (M+H)$^+$; observed 898.2358 (1.4 ppm error).

7

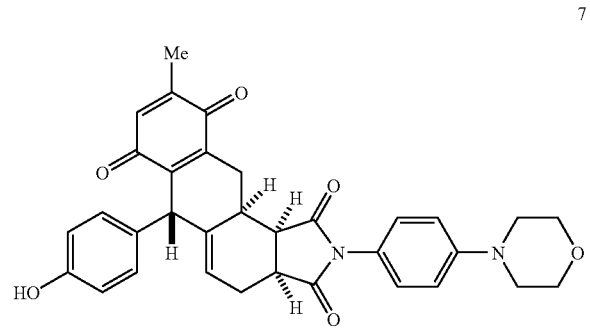

Tetracycle 7: $^1$H NMR (500 MHz, CDCl$_3$) δ 6.95 (d, J=8.5 Hz, 2H), 6.87 (m, 4H), 6.71 (d, J=8.0 Hz, 2H), 6.55 (q, J=1.5 Hz, 1H), 6.04 (m, 1H), 4.93 (s, 1H), 4.68 (s, 1H), 3.84 (t, J=5.0 Hz, 4H), 3.34 (dd, J=17.0, 2.5 Hz, 1H), 3.28 (m, 2H), 3.16 (t, J=5.0 Hz, 4H), 3.02 (m, 1H), 2.94 (dd, J=15.0, 7.0 Hz, 1H), 2.54 (dd, J=17.5, 8.5 Hz, 1H), 2.36 (ddd J=15.5, 6.5, 3.5 Hz, 1H), 2.05 (d, J=1.5 Hz, 3H); $^{13}$C NMR (125 MHz, CDCl$_3$) δ 186.4, 186.1, 178.8, 177.1, 154.4, 151.2, 146.0, 143.4, 140.8, 139.5, 132.6, 132.5, 128.2, 127.1, 123.1, 122.7, 115.6, 115.5, 66.7, 48.7, 43.9, 42.6, 39.1, 32.4, 24.5, 24.1, 16.1; FT-IR (thin film) 3411, 2961, 2907, 2852, 1699, 1690, 1649, 1611, 1513, 1441, 1381, 1261, 1234, 1173, 1113, 922, 818, 730 cm$^{-1}$; HRMS (TOF ES) calcd for $C_{33}H_{31}N_2O_6$, 551.2182 m/z (M+H)$^+$; observed 551.2186 (0.8 ppm error).

BIAcore Experiments

Immobilization. In all experiments, calmodulin (CaM) was immobilized on a carboxymethylated dextran-coated sensor chip (CM5, Biacore AB, Uppsala, Sweden) at 25° C. For protein immobilization, 'specific flow rate' was selected and the protein of interest was immobilized in flow cells 2 and 4. On Biacore 3000, the sensor chip was activated (7 min in flow cells 2 and 4) by addition of 0.2 M N-ethyl-N'-(3-dimethylaminopropyl) carbodiimide hydrochloride (EDC) and 0.05 M N-hydroxysuccinimide (NHS) at 20 µL/min. The native calmodulin was dissolved in 10 mM acetate buffer (pH 4.0) at 0.05 mg/mL and immobilized in flow cells 2 and 4 at 10 µL/min for 25 min. 1 Flow cells 1 and 3 were used as a control with no calmodulin bound. After the coupling step the remaining NHS-esters on the surface were quenched by addition of 1M ethanolamine for 7 min at 20 µL/min. The average immobilization and equilibration, there was an ~800 Response Unit (RU) increase. Assuming a conversion factor of 1000 RU=1 ng/mm$^2$ of material bound to the surface, the protein was immobilized at 47.9 fmol/mm$^2$. After immobilization, the system was primed (2×) and equilibrated (20 µL/min, 2 hr) with the buffer that was used in the binding analysis. Typically the buffer was PBST (50 mM phosphate, 150 mM NaCl, 0.005% Tween 20, pH 7.4) containing 2-5% DMF or DMSO. In this study, PBST containing 4% DMF was used as the binding analysis buffer. In order to insure consistency between the running buffer and sample buffer, the following buffer preparation protocol was used. IL of PBST was prepared, filtered and degassed under reduced pressure. 40 mL of the prepared buffer was then withdrawn and set aside for sample preparation, and 40 mL of DMF was added to the remaining 960 mL of PBST.

Sample preparation. Prior to resynthesis of positives from the small molecule microarrays probes with Cy5-calmodulin, the positives were prioritized by an initial secondary SPR screening. This was done using samples taken directly from the DMF stock solutions used for small molecule microarray preparation. The samples for initial secondary SPR screening were prepared as follows. A 2 µL aliquot of the DMF stock solution was withdrawn from printing plate, and diluted with 2 µL of DMF. This sample solution in DMF (4 µL) was slowly added into 96 µL of warm PBST (~70° C., 1 min). These samples are then centrifuged (2000 rpm, 1 min), and any that then contain a pellet or are turbid are judged to have precipitated compound and discarded. These samples were injected under the application of "direct binding" analysis. The flow rate was 20 µL/min, single injection. The injection time can vary widely depending on the kinetics of the binding, but for typical small molecules (rapid binding and dissociation) a 2-3 minute injection time is sufficient. The 3 min injection times were followed by 2.5 min wait times, and the flow cells were regenerated by dissociation in buffer (30 µL/min, 7 min). Samples were injected in alternation with blanks (injection of 4% DMF/PBST). "Flow cell 2 with 1 as a reference" was selected and each sample was analyzed in duplicate.

After the prioritization step, compounds 5, 6 and 7 were resynthesized, purified and subjected to $K_D$ determination. Samples were injected over a range of concentrations (e.g. 0.1-125 µM). The compound was prepared as a 10 mM stock solution in DMF. Serial dilutions of this stock were made and then added to the heated PBST (~70° C., 1 min). In this analysis, a 200 μL final volume was prepared by addition of 8 μL of small molecule DMF solution into 192 μL of a heated PBST. The final concentration ranged between 0.015 μM and 125 μM. 5 and 6 precipitated at 125 μM in 4% DMF/PBST. Samples were injected in the alternation with blanks. "Flow cell 2 with 1 as a reference" was selected and each sample was analyzed in triplicate. For each experiment, a calibration for bulk differences between flow cells due to the high refractive index of DMF was performed by injecting blank samples containing a range of DMF concentrations (1, 2, 3, 3.5, 4, 4.5, 5%) in PBST under conditions otherwise identical to those used for samples of compounds 5, 6 and 7.

Data analysis. A change in response units was recorded for both the control and active flow cells during injections (including blanks). These values were saved as 'report point tables' and opened in Microsoft Excel. To construct the % co-solvent calibration curve, $RU_{active}$-$RU_{control}$ (y-axis) was plotted against $RU_{control}$ (x-axis) and a linear fit was performed. The equation was used to correct sample values, corresponding to small molecule injections, for bulk co-solvent effect by entering $RU_{control}$ value for x. The equation was solved for y (correction factor). The correction factor was then subtracted from $RU_{active}$-$RU_{control}$ for each sample to give the correct RU value. For all tested samples, this value falls between 0 (blank injection with 4% DMF) and the theoretical $RU_{max}$. The $K_D$ determination was performed by using "BIAevaluation" software. The raw data of the initial secondary SPR analysis are shown in following figures. LC/MS traces (diode array; 200-450 nm) of corresponding compounds are shown thereafter. These compounds were injected directly from the 384 microtiter plate wells used for small molecule printing. The kinetic data for $K_D$ determination are shown immediately thereafter.

Example 11

Synthesis of Diazobenzylidene Precursors

The diazobenzylidene precursors shown below were synthesized as shown and tested in as described above in Example 9. All three of the precursors prepared showed no significant difference in immobilization efficiency. Precursor 1 was studied further as described in Example 10. Precursor 2 and 3 may be useful in assay where a longer spacer between the solid support and the arrayed compound is needed. Precursor 3 demonstrates that other derivatives with substitution on the phenyl may provide the same immobilization efficiency as the unsubstituted precursor.

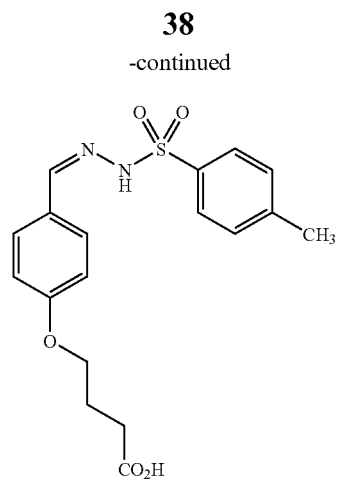

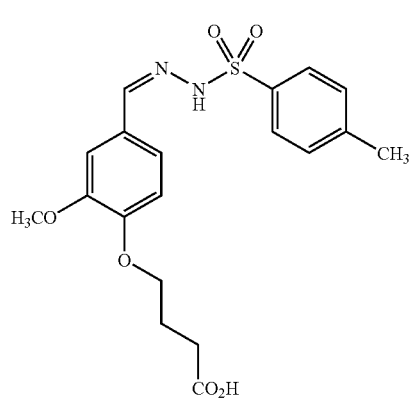

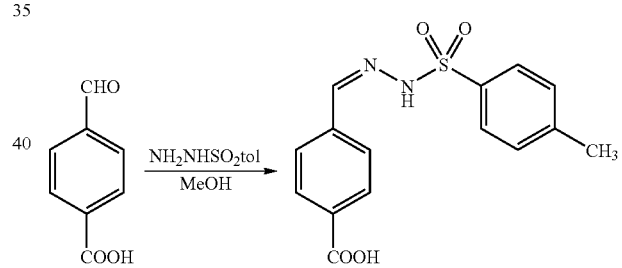

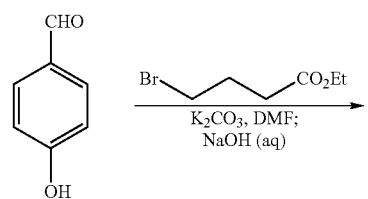

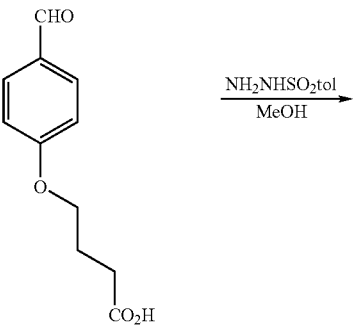

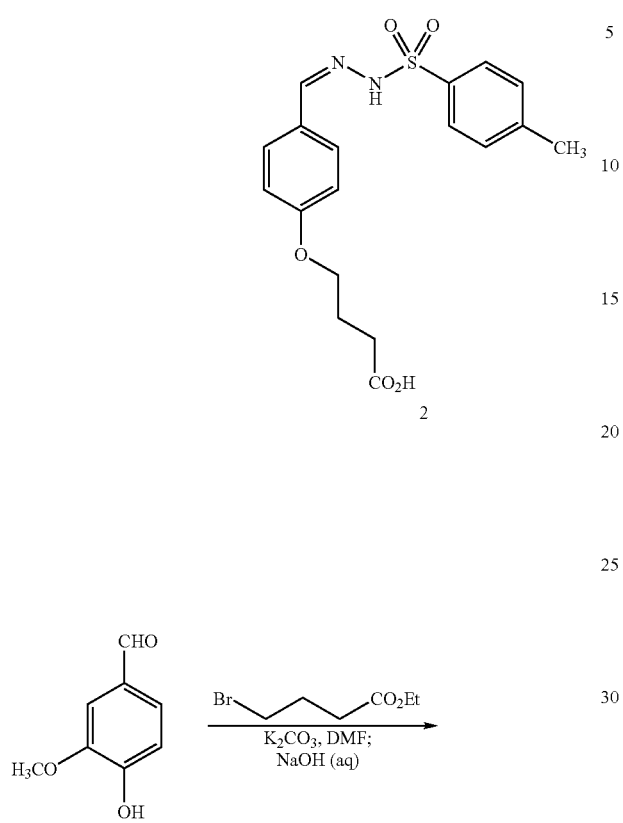

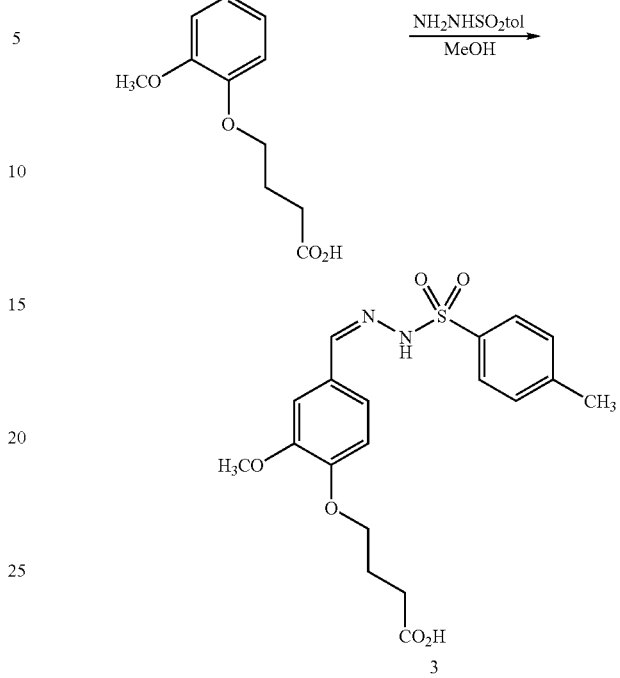

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. An array comprising:
a plurality of more than one type of organic small molecule, having a molecular weight of less than 1500 g/mol, attached to a solid support through a benzylidene linker, wherein said solid support is a substantially flat surface derivatized with diazobenzylidene moieties, whereby said organic small molecules become attached to said support through reaction with said diazobenzylidene moieties, wherein attachment of said organic small molecules to said support is robust enough so that the small molecules are not inadvertently cleaved during subsequent assaying steps, wherein the density of said array of organic small molecules comprises at least 1000 spots per cm$^2$, and wherein said organic small molecules attached to said benzylidine linker attached to said solid support is as shown below:

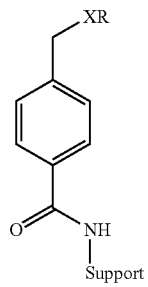

wherein X is a heteroatom selected from the group consisting of O, S, and N, of the attached organic small molecule R.

2. The array of claim 1, wherein said array of organic small molecules comprises an array of non-oligomeric organic small molecules.

3. The array of claim 1, wherein said array of organic small molecules comprises an array of non-peptidic and non-oligomeric organic small molecules.

4. The array of claim 1, wherein the solid support is glass.

5. The array of claim 1, wherein the solid support is derivatized glass.

6. The array of claim 1, wherein the solid support is sylated glass.

7. The array of claim 1, wherein the solid support is γ-aminopropylsilylated glass.

8. The array of claim 1, wherein the solid support is a polymer.

9. The array of claim 1, wherein the solid support is metal.

10. The array of claim 1, wherein the solid support is a metal-coated surface.

11. The array of claim 1, wherein the solid support is a gold-coated surface.

12. A solid support comprising a substantially flat glass surface, wherein said glass surface is derivatized with diazobenzylidene moieties, and wherein the solid support has the structure:

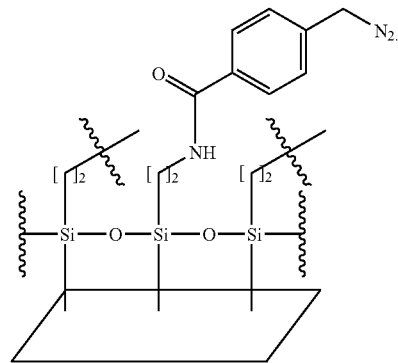

13. A method for forming the array of claim 1, the method comprising:
providing a solid support, wherein said solid support is a substantially flat surface derivatized with diazobenzylidene moieties capable of interacting with more than one type of organic small molecule, having a molecular weight of less than 1500 g/mol, to form a covalent linkage;
providing one or more solutions of more than one type of said organic small molecule to be attached to said solid support; and
delivering said one or more solutions of said more than one type of organic small molecule to said solid support, whereby each of said organic small molecules is attached to said solid support through a covalent interaction, wherein attachment of said organic small molecules to said support is robust enough so that the small molecules are not inadvertently cleaved during subsequent assaying steps, and whereby said array of organic small molecules has a density of at least 1000 spots per cm$^2$, and wherein the array comprises organic small molecules attached to said benzylidene linker attached to said solid support as shown below:

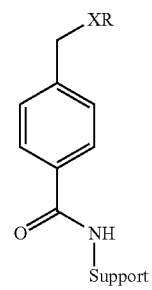

wherein X is a heteroatom selected from the group consisting of O, S, and N, of the attached organic small molecule R.

14. The method of claim 13, wherein said solid support comprises a glass slide.

15. The method of claim 13, wherein providing a solution of one or more types of organic small molecules to be attached to the solid support comprises providing one or more solutions generated from a library of organic small molecules, wherein each member of said library is initially attached to a bead, placed in an individual well, then cleaved from the bead to provide the solution.

16. A method of identifying organic small molecule partners for biological macromolecules of interest comprising:

provEXT the array of claim 8, wherein said array comprises an array of organic small molecules, having a molecular weight of less than 1500 g/mol, attached to a substantially flat solid support through a benzylidene linker, wherein attachment of said organic small molecules to said support is robust enough so that the small molecules are not inadvertently cleaved during subsequent assaying steps, and wherein said array of organic small molecules has a density of at least 1000 spots per cm$^2$;

contacting said array with one of more types of biological macromolecules of interest; and determining the binding of specific organic small molecule-biological macromolecule partners; wherein the array comprises organic small molecules attached to said benzylidine linker attached to said solid support as shown below:

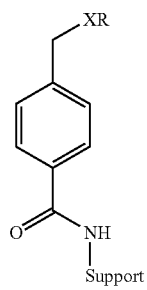

wherein X is a heteroatom selected from the group consisting of O, S, and N, of the attached organic small molecule R.

17. A method for identifying organic small molecule partners for a gene product comprising:

providing the array of claim 8, wherein said array comprises an array of organic small molecules, having a molecular weight of less than 1500 g/mol, attached to a substantially flat solid support through a benzylidene linker, wherein attachment of said organic small molecules to said support is robust enough so that the small molecules are not inadvertently cleaved during subsequent assaying steps, and wherein said array of organic small molecules has a density of at least 1000 spots per cm$^2$;

contacting said array with a library of recombinant proteins; and determining the binding of specific recombinant proteins with said organic small molecule partners; wherein the array comprises organic small molecules attached to said benzylidine linker attached to said solid support as shown below:

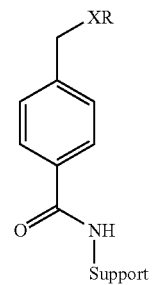

wherein X is a heteroatom selected from the group consisting of O, S, and N, of the attached organic small molecule R.

* * * * *

UNITED STATES PATENT AND TRADEMARK OFFICE
CERTIFICATE OF CORRECTION

| | |
|---|---|
| PATENT NO. | : 7,932,213 B2 |
| APPLICATION NO. | : 10/370885 |
| DATED | : April 26, 2011 |
| INVENTOR(S) | : Seung Bum Park et al. |

It is certified that error appears in the above-identified patent and that said Letters Patent is hereby corrected as shown below:

At column 1, lines 13-19, please remove the "Government Support" section.

In claim 12 at column 42, lines 1-27, please replace the structure:

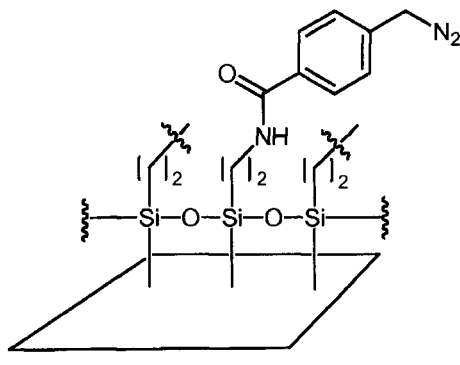

, with the structure:

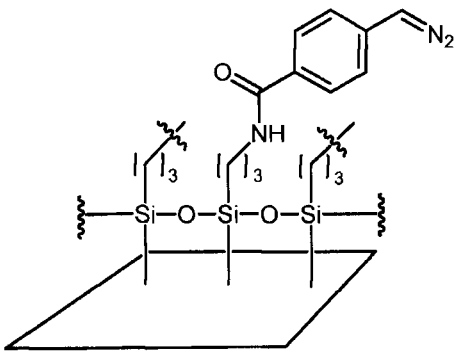

.

In claim 16 at column 43, line 12, please correct the claim dependency as follows:
... providing the array of claim 1 [[8]], wherein said array....

Signed and Sealed this
Thirtieth Day of August, 2011

David J. Kappos
*Director of the United States Patent and Trademark Office*

In claim 17 at column 44, line 6, please correct the claim dependency as follows:
... providing the array of claim <u>1</u> [[8]], wherein said array....

SEQUENCE LISTING

```
<160> NUMBER OF SEQ ID NOS: 3

<210> SEQ ID NO 1
<211> LENGTH: 36
<212> TYPE: DNA
<213> ORGANISM: Artificial Sequence
<220> FEATURE:
<223> OTHER INFORMATION: PCR primers for fragment of human FKBP12

<400> SEQUENCE: 1
acgtacgtgg atccatggga gtgcaggtgg aaacca                            36

<210> SEQ ID NO 2
<211> LENGTH: 43
<212> TYPE: DNA
<213> ORGANISM: Artificial Sequence
<220> FEATURE:
<223> OTHER INFORMATION: PCR primers for fragment of human FKBP12

<400> SEQUENCE: 2
acgtacgtgt cgacttattc cagttttaga agctccacat cga                    43

<210> SEQ ID NO 3
<211> LENGTH: 6
```

```
<212>  TYPE:  PRT
<213>  ORGANISM:  Artificial Sequence
<220>  FEATURE:
<223>  OTHER INFORMATION:  Histidine tag for purification

<400>  SEQUENCE:  3

His His His His His His
1               5
```